(12) United States Patent
Matsumoto et al.

(10) Patent No.: US 7,426,026 B2
(45) Date of Patent: Sep. 16, 2008

(54) METHOD AND SYSTEM FOR MEASURING THE CONCENTRATIONS OF FLUORESCENT DYES

(75) Inventors: Kazuji Matsumoto, Hamamatsu (JP); Masahiko Hirano, Hamamatsu (JP); Masahiro Hara, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 83 days.

(21) Appl. No.: 10/574,943

(22) PCT Filed: Oct. 8, 2004

(86) PCT No.: PCT/JP2004/014968

§ 371 (c)(1), (2), (4) Date: Dec. 19, 2006

(87) PCT Pub. No.: WO2005/036143

PCT Pub. Date: Apr. 21, 2005

(65) Prior Publication Data

US 2007/0121099 A1 May 31, 2007

(30) Foreign Application Priority Data

Oct. 10, 2003 (JP) ............... 2003-352790

(51) Int. Cl.
*G01J 3/30* (2006.01)

(52) U.S. Cl. .................... 356/317; 250/459.1

(58) Field of Classification Search ............... 356/317; 250/459.1
See application file for complete search history.

(56) References Cited

U.S. PATENT DOCUMENTS 6,091,843 A * 7/2000 Horesh et al. ............ 250/461.1

(Continued)

FOREIGN PATENT DOCUMENTS

JP 3280035 2/2002

(Continued)

OTHER PUBLICATIONS

Gary R. Bright, "Multiparameter Imaging of Cellular Function," Biological Techniques, Fluorescent and Luminescent Probes for Biological Activity, A Practical Guide to Technology for Quantitative Real-TIme Analysis, 1993, pp. 204-215.

(Continued)

*Primary Examiner*—Kara E Geisel
(74) *Attorney, Agent, or Firm*—Drinker Biddle & Reath LLP

(57) ABSTRACT

By using an imaging device (30), it is possible to determine the concentration of flourescent pigments contained in a target sample (1). The imaging device has a plurality of detection wavelength bands. There are prepared a plurality of reference samples, each containing each of the flourescent pigments in a predetermined unit concentration, so as to obtain measurement intensity of flourescent light emitted from each reference sample at each detection wavelength band. The flourescent image of the target sample is imaged at each detection wavelength band by using the imaging device. By using the flourescent intensities obtained from the reference sample and the target sample, calculation is executed so as to obtain the concentration of each of the flourescent pigments in the target sample.

16 Claims, 26 Drawing Sheets

U.S. PATENT DOCUMENTS

2001/0033364 A1* 10/2001 Cabib et al. ............... 351/221
2002/0158211 A1* 10/2002 Gillispie ............... 250/458.1
2004/0021861 A1* 2/2004 Lewis et al. ............... 356/326

FOREIGN PATENT DOCUMENTS

| JP | 2002-168868 | 6/2002 |
|----|-------------|--------|
| JP | 2003-270129 | 9/2003 |
| JP | 2004-163312 | 6/2004 |
| WO | WO 01/09592 | 2/2001 |

OTHER PUBLICATIONS

Atsushi Miyawaki et al., "Fluorescent indicators for $Ca^{2+}$ based on green fluorescent proteins and calmodulin," Nature, vol. 388, Aug. 28, 1997, pp. 882-887.

Gerald W. Gordon et al., "Quantitative Fluorescence Resonance Energy Transfer Measurements Using Fluorescence Microscopy," Biophysical Journal, vol. 74, May 1998, pp. 2702-2713.

M. E. Dickinson et al., "Multi-Spectral Imaging and Linear Unmixing Add a Whole New Dimension to Laser Scanning Fluorescence Microscopy," BioTechniques, vol. 31, No. 6 (2001), pp. 1272-1279.

Timo Zimmerman et al., "Spectral imaging and its applications in live cell microscopy," FEBS Letters 546 (2003), pp. 87-92.

Mary E. Dickinson et al., "Multiphoton excitation spectra in biological samples," Journal of Biomedical Optics, 8(3), Jul. 2003, pp. 329-338.

Satoshi Kawada, "Imaging Spectroscopy ni yoru Pattern Bunseki," Japanese Journal of Optics, Jan. 10, 1989, vol. 18, No. 1, pp. 8-14, including English-language translation.

* cited by examiner

Fig.24
(a)
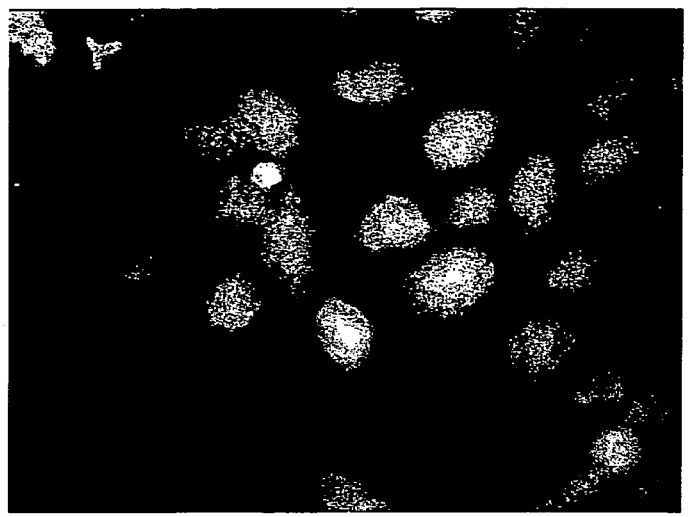
(b)
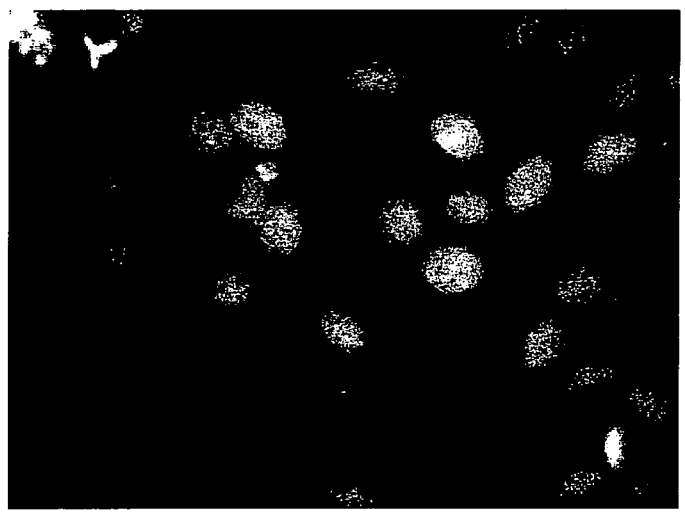
(c)
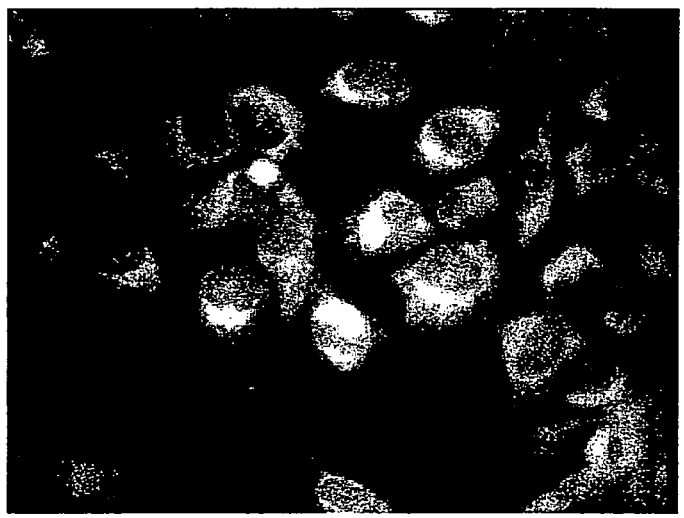

Fig.25
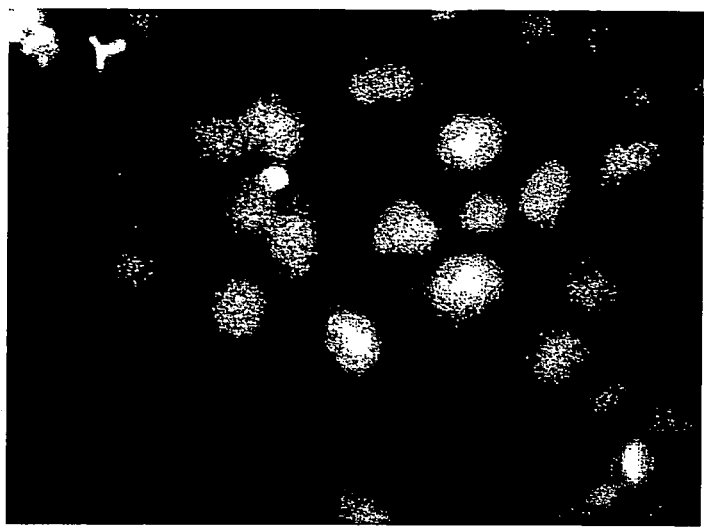
(a)
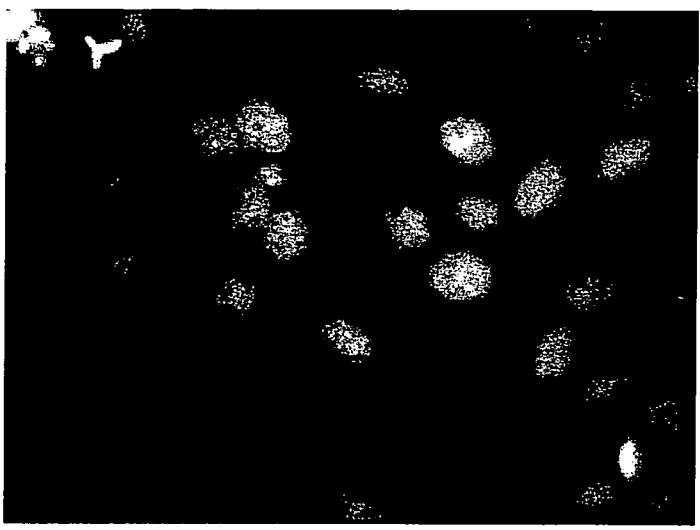
(b)
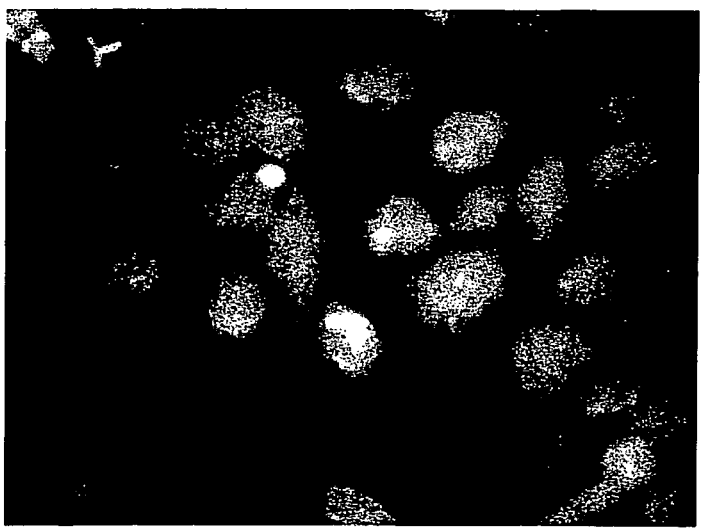
(c)

METHOD AND SYSTEM FOR MEASURING THE CONCENTRATIONS OF FLUORESCENT DYES

TECHNICAL FIELD

The present invention relates to measurement of the concentrations of fluorescent dyes contained in a sample.

BACKGROUND ART

A method of measuring the concentration of a fluorescent dye contained in a sample is described in Gary R. Bright, "Multiparameter Imaging of Cellular Function" on pp 204-215 in "Fluorescent and Luminescent Probes for Biological Activity" edited by W. T. Mason, 1993, Academic Press, USA. This method is to extract a wavelength component necessary for excitation of a fluorescent dye, from white light by means of a dichroic filter and to illuminate a sample with the wavelength component to produce fluorescence. This fluorescence is detected through a band-pass filter and with a monochrome (black-and-white) camera, and the intensity thereof is measured. The band-pass filter is used for receiving only the wavelength component corresponding to the fluorescent dye in the sample, with the camera. Since the intensity of the fluorescence emitted from the fluorescent dye in the sample is proportional to a concentration of the fluorescent dye, the intensity of the fluorescence measured in this manner is handled as the concentration of the fluorescent dye.

This method is implemented using a filter set consisting of the dichroic filter and the band-pass filter according to the fluorescent dye. As long as the sample contains only one kind of fluorescent dye, one filter set can be fixedly used. However, if the sample contains two or more kinds of fluorescent dyes, a plurality of filter sets must be used as replaced one from another during measurement of the sample. The replacement of filter set will cause a slight change in an optical system and thus affect the accuracy of the measurement. In addition, the replacement of filter set will produce a difference between measurement times of different fluorescent dyes. This is undesirable for measurement of a living sample.

The above-described method also has a point to be improved in terms of the measurement accuracy. In a case where peak wavelengths of fluorescent dyes in a sample are located close to each other, wings of fluorescence spectra overlap with each other. In this case, it is infeasible to extract only a wavelength component corresponding to a single fluorescent dye from the fluorescence spectra even with the use of the band-pass filter, and a wavelength component of another fluorescent dye shall be mixed in the fluorescence having passed through the filter. This degrades the accuracy of the measurement of the fluorescent dye.

DISCLOSURE OF THE INVENTION

An object of the present invention is to accurately measure the concentrations of a plurality of fluorescent dyes.

In one aspect, the present invention relates to a method of measuring the concentrations of fluorescent dyes in a sample. This method measures the concentrations of first to mth (where m is an integer of 2 or more) fluorescent dyes contained in a target sample, using an imaging device having first to kth (where k is an integer of 2 or more) different detection wavelength bands. Portions of the detection wavelength bands overlap any adjacent bands. In this method, first to mth reference samples are prepared, each of which contains only one of the first to mth fluorescent dyes respectively at predetermined unit concentrations, and a measured intensity of fluorescence emitted from each reference sample is acquired in each detection wavelength band. A fluorescence image of the target sample is taken in each detection wavelength band using the imaging device. Then an operation represented by a formula below is executed to calculate concentrations $c_1$-$c_m$ of the first to mth fluorescent dyes at a site in the target sample.

[Formula 1]

$$\begin{bmatrix} c_1 \\ c_2 \\ \vdots \\ c_m \end{bmatrix} = (J^T \cdot J)^{-1} \cdot J^T \cdot \begin{bmatrix} O_1 \\ O_2 \\ \vdots \\ O_k \end{bmatrix},$$

$$J = \begin{bmatrix} J_{11} & J_{12} & \cdots & J_{1m} \\ J_{21} & J_{22} & \cdots & J_{2m} \\ \vdots & \vdots & & \vdots \\ J_{k1} & J_{k2} & \cdots & J_{km} \end{bmatrix}$$

In this formula, $O_1$-$O_k$ represent the values of pixels in the fluorescence images of the target sample taken in the first to kth detection wavelength bands, and the pixels correspond to the site. J represents a k×m matrix, and a component $J_{ij}$ in the ith row and jth column (where i is any integer from 1 to k, and j any integer from 1 to m) in J represents the measured intensity in the ith detection wavelength band of the fluorescence emitted from the jth reference sample.

The above calculation formula is not affected by overlap between the fluorescence spectra of the fluorescent dyes contained in the target sample. Thus, by this measurement method, it is possible to accurately determine the concentrations of the fluorescent dyes having the overlapping fluorescence spectra.

The imaging device may include a multiband camera having the first to kth detection wavelength bands. The acquisition of the measured intensity of the fluorescence emitted from each reference sample in each detection wavelength band may include taking a fluorescence image of each reference sample in each detection wavelength band using the multiband camera and acquiring the value of a pixel representing a site emitting fluorescence in each reference sample, from each fluorescence image. The calculation of the concentrations $c_1$-$c_m$ of the first to mth fluorescent dyes may use the value of the pixel acquired from the fluorescence image of the jth reference sample taken in the ith detection wavelength band as the component $J_{ij}$ in the matrix J. In this case, the fluorescence intensities of the reference samples and the target sample both can be measured using the same multiband camera. Consequently, the concentrations of the fluorescent dyes can be readily measured.

The imaging device may include a multiband camera having the first to kth detection wavelength bands. The acquisition of the measured intensity of the fluorescence emitted from each reference sample in each detection wavelength band may include measuring the spectral intensities of the fluorescence emitted from each reference sample using a spectrometer, and calculating a measured intensity in each detection wavelength band of the fluorescence emitted from each reference sample using the spectral intensities and the sensitivity characteristic of the multiband camera for each detection wavelength band. In this manner, the measured intensity of the fluorescence emitted from each reference sample in each detection wavelength band can also be acquired using the spectrometer, instead of the direct acquisition using the imaging device.

In another aspect, the present invention relates to a method of measuring the concentrations of first to mth (where m is an integer of 2 or more) fluorescent dyes contained in a target sample, using an imaging device. The imaging device has first to kth (where k is an integer of 2 or more) different detection wavelength bands, and first to qth (where q is an integer of 2 or more) sensitivity modes for setting different sensitivity characteristics of the imaging device. Portions of the detection wavelength bands overlap any adjacent bands. In this method, first to mth reference samples are prepared, each of which contains only one of the first to mth fluorescent dyes respectively at predetermined unit concentrations, and a measured intensity of fluorescence emitted from each reference sample is acquired in each detection wavelength band and in each sensitivity mode. A fluorescence image of the target sample is taken in each detection wavelength band and in each sensitivity mode using the imaging device. Then, an operation represented by a formula below is executed to calculate concentrations $c_1$-$c_m$ of the first to mth fluorescent dyes at a site in the target sample.

[Formula 2]

$$\begin{bmatrix} c_1 \\ c_2 \\ \vdots \\ c_m \end{bmatrix} = (J_1^T \cdot J_1)^{-1} \cdot J_1^T \cdot \begin{bmatrix} P_1 \\ P_2 \\ \vdots \\ P_q \end{bmatrix},$$

$$P_v = \begin{bmatrix} P_{1v} \\ P_{2v} \\ \vdots \\ P_{kv} \end{bmatrix}$$

$$J_1 = \begin{bmatrix} L_{11} & L_{12} & \cdots & L_{1m} \\ L_{21} & L_{22} & \cdots & L_{2m} \\ \vdots & \vdots & & \vdots \\ L_{q1} & L_{q2} & \cdots & L_{qm} \end{bmatrix},$$

$$L_{vj} = \begin{bmatrix} L_{1vj} \\ L_{2vj} \\ \vdots \\ L_{kvj} \end{bmatrix}$$

In this formula, $P_v$ (where v is any integer from 1 to q) represents a k×1 matrix, and a component $P_{iv}$ (where i is any integer from 1 to k) in the ith row in $P_v$ represents the value of a pixel in the fluorescence image of the target sample taken in the ith detection wavelength band and in the vth sensitivity mode using the imaging device, and the pixel corresponds to the site. $J_1$ represents a (k·q)×m matrix, and a component $L_{ivj}$ in the ith row in a component matrix $L_{vj}$ (where j is any integer from 1 to m) in $J_1$ represents the measured intensity of the fluorescence emitted from the jth reference sample in the ith detection wavelength band and in the vth sensitivity mode.

The above calculation formula is not affected by overlap between the fluorescence spectra of the plurality of fluorescent dyes contained in the target sample. Thus, by this measurement method, it is possible to accurately determine the concentrations of the fluorescent dyes having the overlapping fluorescence spectra. The number of fluorescent dyes that can be measured by this method is equal to (the number of detection wavelength bands)×(the number of sensitivity modes). Therefore, it is possible to increase the number of fluorescent dyes that can be measured, according to the number of sensitivity modes.

In still another aspect, the present invention relates to a method of measuring the concentrations of first to mth (where m is an integer of 2 or more) fluorescent dyes contained in a target sample, using an imaging device having first to kth (where k is an integer of 2 or more) different detection wavelength bands. Portions of the detection wavelength bands overlap any adjacent bands. In this method, first to mth reference samples are prepared, each of which contains only one of the first to mth fluorescent dyes respectively at predetermined unit concentrations, the first to mth reference samples are illuminated with each of first to rth (where r is an integer of 2 or more) excitation beams having different wavelength spectra for exciting all the first to mth fluorescent dyes, and a measured intensity of fluorescence emitted from each reference sample is acquired in each detection wavelength band. The target sample is illuminated with each excitation beam and a fluorescence image of the target sample is taken in each detection wavelength band using the imaging device. Then, an operation represented by a formula below is executed to calculate the concentrations $c_1$-$c_m$ of the first to mth fluorescent dyes at a site in the target sample.

[Formula 3]

$$\begin{bmatrix} c_1 \\ c_2 \\ \vdots \\ c_m \end{bmatrix} = (J_2^T \cdot J_2)^{-1} \cdot J_2^T \cdot \begin{bmatrix} Q_1 \\ Q_2 \\ \vdots \\ Q_r \end{bmatrix},$$

$$Q_u = \begin{bmatrix} Q_{1u} \\ Q_{2u} \\ \vdots \\ Q_{ku} \end{bmatrix}$$

$$J_2 = \begin{bmatrix} T_{11} & T_{12} & \cdots & T_{1m} \\ T_{21} & T_{22} & \cdots & T_{2m} \\ \vdots & \vdots & & \vdots \\ T_{r1} & T_{r2} & \cdots & T_{rm} \end{bmatrix},$$

$$T_{uj} = \begin{bmatrix} T_{1uj} \\ T_{2uj} \\ \vdots \\ T_{kuj} \end{bmatrix}$$

In this formula, $Q_u$ (where u is any integer from 1 to r) represents a k×1 matrix, and a component $Q_{iu}$ in the ith row (where i is any integer from 1 to k) in $Q_u$ represents the value of a pixel in the fluorescence image of the target sample taken in the ith detection wavelength band upon illuminating the target sample with the uth excitation beam, and the pixel corresponds to the site. $J_2$ represents a (k·r)×m matrix, and a component $T_{iuj}$ in the ith row of a component matrix $T_{uj}$ (where j is any integer from 1 to m) in $J_2$ represents the measured intensity of the fluorescence emitted from the jth reference sample in the ith detection wavelength band upon illuminating the jth reference sample with the uth excitation beam.

The above-described calculation formula is not affected by overlap between the fluorescence spectra of the plurality of fluorescent dyes contained in the target sample. Thus, by this measurement method, it is possible to accurately determine the concentration of the fluorescent dyes having the overlapping fluorescence spectra. The number of fluorescent dyes that can be measured by this method is equal to (the number of detection wavelength band)×(the number of types of excitation beams). Therefore, it is possible to increase the number of fluorescent dyes that can be measured, according to the number of types of excitation beams.

In these measurement methods of the present invention, the imaging device may include one or more imaging devices for taking fluorescent images of the target sample in the first to kth detecting wavelength bands to generate first to kth image signals, and an arithmetic circuit to which the first to kth image signals are fed. The calculation of the concentrations $c_1$-$c_m$ of the first to mth fluorescent dyes may include a process in which the arithmetic circuit executes the operation using the first to kth image signals. These measurement methods may further include causing the arithmetic circuit to calculate the concentrations $c_1$-$c_m$ at a plurality of sites in the target sample, and to generate first to mth image signals indicating the concentration distributions of the first to mth fluorescent dyes. In these measurement methods, the imaging device calculates the concentrations of the fluorescent dyes, using the fluorescence image signals of the target sample acquired by itself, and generates the image signals indicating the concentration distributions. Therefore, these measurement methods are able to quickly present the measurement results.

In another aspect, the present invention relates to a system for measuring the concentrations of first to mth (where m is an integer of 2 or more) fluorescent dyes contained in a target sample. This system comprises a photodetector, an imaging device, and an arithmetic device. The photodetector detects fluorescence emitted from each of first to mth reference samples each containing only one of the first to mth fluorescent dyes respectively in predetermined unit concentrations, and measures the intensity of the fluorescence. The imaging device has first to kth (where k is an integer of 2 or more) different detection wavelength bands, and takes a fluorescence image of the target sample in each detection wavelength band. Portions of the detection wavelength bands overlap any adjacent bands. The arithmetic device executes an operation represented by a formula below, to calculate the concentrations $c_1$-$c_m$ of the first to mth fluorescent dyes at a site in the target sample.

[Formula 4]

$$\begin{bmatrix} c_1 \\ c_2 \\ \vdots \\ c_m \end{bmatrix} = (J^T \cdot J)^{-1} \cdot J^T \cdot \begin{bmatrix} O_1 \\ O_2 \\ \vdots \\ O_k \end{bmatrix},$$

$$J = \begin{bmatrix} J_{11} & J_{12} & \cdots & J_{1m} \\ J_{21} & J_{22} & \cdots & J_{2m} \\ \vdots & \vdots & & \vdots \\ J_{k1} & J_{k2} & \cdots & J_{km} \end{bmatrix}$$

In this formula, $O_1$-$O_k$ represent the values of pixels in the fluorescence images of the target sample taken in the first to kth detection wavelength bands, and these pixels correspond to the site. J represents a k×m matrix, and a component $J_{ij}$ in the ith row and jth column (where i is any integer from 1 to k, and j any integer from 1 to m) in J represents the intensity of the fluorescence emitted from the jth reference sample in the ith detection wavelength band, measured by the photodetector.

The above-described calculation formula is not effected by overlap between the fluorescence spectra of the plurality of fluorescent dyes contained in the target sample. Thus, this measurement system is able to accurately determine the concentrations of the fluorescent dyes having the overlapping fluorescence spectra.

A multiband camera having the first to kth (where k is an integer of 2 or more) detection wavelength bands may be used as the photodetector and the imaging device. The photodetector may be configured to caste a fluorescence image of each reference sample in each detection wavelength band and to acquire the value of a pixel representing a site emitting fluorecence in each reference sample, from each fluorescence image. The arithmetic device may use the value of the pixel acquired from the fluorescence image of the jth reference sample taken in the ith detection wavelength band as the component $J_{ij}$ in the matrix J. In this case, the fluorescence intensities of both the reference samples and the target sample can be measured with using same multiband camera. Therefore, the concentrations of the fluorescent dyes can be readily measured.

The photodetector may include a spectrometer for measuring spectral intensities of the fluorescence emitted from each reference sample. The imaging device may include a multiband camera having the first to kth detection wavelength bands. The arithmetic device may be configured to calculate the intensity of the fluorescence emitted from each reference sample in each detection wavelength band, using the spectral intensities measured by the spectrometer and a sensitivity characteristic of the multiband camera for each detection wavelength band, and to use the calculated intensities as components of the matrix J. Thus, the measured intensity in each detection wavelength band of the fluorescence emitted from each reference sample can also be acquired using the spectrometer, instead of the direct acquisition using the imaging device.

In still another aspect, the present invention relates to a system for measuring the concentrations of first to mth (where m is an integer of 2 or more) fluorescent dyes contained in a target sample. This system comprises a photodector, an imaging device, and an arithmetic device. The photodetector detects fluorescence emitted from each of first to mth reference samples each containing only one of the first to mth fluorescent dyes respectively at predetermined unit concentrations, and measures the intensity of the fluorescence. The imaging device has first to kth (where k is an integer of 2 or more) different detection wavelength bands, and first to qth (q is an integer of 2 or more) sensitivity modes for setting different sensitivity characteristics of the imaging device. Portions of the detection wavelength bands overlap any adjacent bands. This imaging device takes a fluorescence image of the target sample in each detection wavelength band and in each sensitivity characteristic. The arithmetic device executes an operation represented by a formula below, to calculate concentrations $c_1$-$c_m$ of the first to mth fluorescent dyes at a site in the target sample.

[Formula 5]

$$\begin{bmatrix} c_1 \\ c_2 \\ \vdots \\ c_m \end{bmatrix} = (J_1^T \cdot J_1)^{-1} \cdot J_1^T \cdot \begin{bmatrix} P_1 \\ P_2 \\ \vdots \\ P_q \end{bmatrix},$$

$$P_v = \begin{bmatrix} P_{1v} \\ P_{2v} \\ \vdots \\ P_{kv} \end{bmatrix}$$

$$J_1 = \begin{bmatrix} L_{11} & L_{12} & \cdots & L_{1m} \\ L_{21} & L_{22} & \cdots & L_{2m} \\ \vdots & \vdots & & \vdots \\ L_{q1} & L_{q2} & \cdots & L_{qm} \end{bmatrix},$$

$$L_{vj} = \begin{bmatrix} L_{1vj} \\ L_{2vj} \\ \vdots \\ L_{kvj} \end{bmatrix}$$

In this formula, $P_v$ (where v is any integer from 1 to q) represents a k×1 matrix, and a component $P_{iv}$ in the ith row (where i is any integer from 1 to k) in $P_v$ represents the value of a pixel in the fluorescence image of the target sample taken in the ith detection wavelength band and in the vth sensitivity mode, and the pixel corresponds to the site. $J_1$ represents a (k·q)×m matrix, and a component $L_{ivj}$ in the ith row in a component matrix $L_{vj}$ (where j is any integer from 1 to m) in $J_1$ represents the measured intensity in the ith detection wavelength band and in the vth sensitivity mode of the fluorescence emitted from the jth reference sample.

The above-described calculation formula is not affected by overlap between the fluorescence spectra of the plurality of fluorescent dyes contained in the target sample. Thus, this measurement system is able to accurately determine the concentrations of the fluorescent dyes having the overlapping fluorescence spectra. The number of fluorescent dyes that can be measured by this system is equal to (the number of detection wavelength bands)×(the number of sensitivity modes). Therefore, it is possible to increase the number of fluorescent dyes that can be measured, according to the number of sensitivity modes.

In still another aspect, the present invention relates to a system for measuring the concentrations of first to mth (where m is an integer of 2 or more) fluorescent dyes contained in a target sample. This system comprises a light source, a photodetector, an imaging device, and an arithmetic device. The light source generates first to rth (where r is an integer of 2 or more) excitation beams having different wavelength spectra for exciting all the first to mth fluorescent dyes. The photodetector measures the intensity of fluorescence emitted from each of first to mth reference samples upon illuminating each reference sample with each excitation beam, each reference sample containing only one of the first to mth fluorescent dyes respectively at predetermined unit concentrations. The imaging device has first to kth (where k is an integer of 2 or more) different detection wavelength bands. Portions of the detection wavelength bands overlap any adjacent bands. The imaging device takes a fluorescence image of the target sample in each detection wavelength band upon illuminating the target sample with each excitation beam. The arithmetic device executes an operation represented by a formula below, to calculate concentrations $c_1$-$c_m$ of the first to mth fluorescent dyes at a site in the target sample.

[Formula 6]

$$\begin{bmatrix} c_1 \\ c_2 \\ \vdots \\ c_m \end{bmatrix} = (J_2^T \cdot J_2)^{-1} \cdot J_2^T \cdot \begin{bmatrix} Q_1 \\ Q_2 \\ \vdots \\ Q_r \end{bmatrix},$$

$$Q_u = \begin{bmatrix} Q_{1u} \\ Q_{2u} \\ \vdots \\ Q_{ku} \end{bmatrix}$$

$$J_2 = \begin{bmatrix} T_{11} & T_{12} & \cdots & T_{1m} \\ T_{21} & T_{22} & \cdots & T_{2m} \\ \vdots & \vdots & & \vdots \\ T_{r1} & T_{r2} & \cdots & T_{rm} \end{bmatrix},$$

$$T_{uj} = \begin{bmatrix} T_{1uj} \\ T_{2uj} \\ \vdots \\ T_{kuj} \end{bmatrix}$$

In this formula, $Q_u$ (where u is any integer from 1 to r) represents a k×1 matrix, and a component $Q_{iu}$ in the ith row (where i is any integer from 1 to k) in $Q_u$ represents the value of a pixel in the fluorescence image of the target sample taken in the ith detection wavelength band upon illuminating the target sample with the uth excitation beam, and the pixel corresponds to the site. $J_2$ represents a (k·r)×m matrix, and a component $T_{iuj}$ in the ith row in a component matrix $T_{uj}$ (where j is any integer from 1 to m) in $J_2$ represents the measured intensity of the fluorescence in the ith detection wavelength band upon illuminating the jth reference sample with the uth excitation beam.

The above-described calculation formula is not affected by overlap between the fluorescence spectra of the plurality of fluorescent dyes contained in the target sample. Thus, this measurement system is able to accurately determine the concentrations of the fluorescent dyes having the overlapping fluorescence spectra. The number of fluorescent dyes that can be measured by this system is equal to (the number of detection wavelength bands)×(the number of types of excitation beams). Therefore, it is possible to increase the number of fluorescent dyes that can be measured, according to the number of types of excitation beams.

In the measurement system of the present invention, the imaging device may include one or more imaging devices for taking the fluorescence images of the target sample in the first to kth detection wavelength bands to generate first to kth image signals, and an arithmetic circuit as the aforementioned arithmetic device. The first to kth image signals are fed to this arithmetic circuit. The arithmetic circuit may be configured to execute the operation using the first to kth image signals, to calculate the concentrations $c_1$-$c_m$ at a plurality of sites of the target sample, and to generate first to mth image signals indicating the concentration distributions of the first to mth fluorescent dyes. In this measurement system, the imagine device calculates the concentrations of the fluorescent dyes, using the fluorescence image signals of the target sample acquired by itself, and generates the image signals indicating the concentration distributions. Consequently, this measurement system is able to quickly present the measurement results.

BRIEF DESCRIPTION OF THE DRAWINGS

FIG. 24 is photographs showing images acquired in the eighth embodiment.

FIG. 25 is photographs showing images acquired in a comparative example.

BEST MODE FOR CARRYING OUT THE INVENTION

Embodiments of the present invention will be described below in detail with reference to the accompanying drawings. In the description of the drawings the same elements will be denoted by the same reference symbols, without redundant description.

First Embodiment

Figure 1:
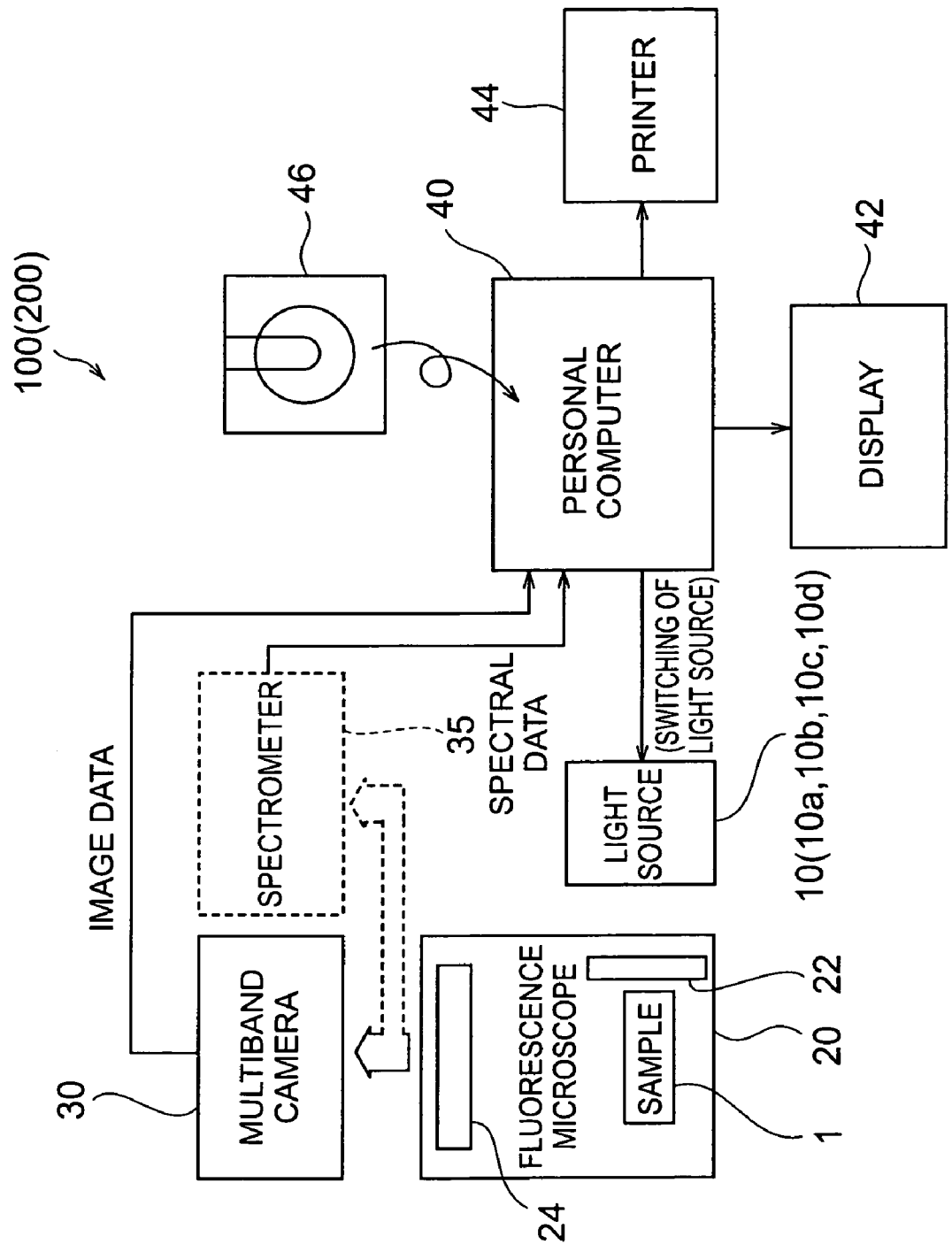
FIG. 1 is a block diagram showing a configuration of an example of a fluorescent dye measurement system.

FIG. 1 is a block diagram showing a configuration of a fluorescent dye measurement system of the present embodiment. The measurement system 100 has a light source 10, a fluorescence microscope 20, a multiband camera 30, and a personal computer 40. A display device 42 and a printer 44 are connected to the computer 40. The measurement system 100 measures the concentrations of fluorescent dyes contained in a target sample. The measurement system 100 can measure the concentrations of three or less types of fluorescent dyes. It is assumed in the present embodiment that types of fluorescent dyes contained in the target sample are preliminarily known.

The light source 10 generates light for exciting a sample 1 and illuminates the sample 1 with the light. The light source 10 has a Xe lamp 10a and a multicolor emission type LED 10b one of which is selectively used. The computer 40 controls which is to be used out of the Xe lamp 10a and LED 10b. The Xe lamp 10a is used in the present embodiment.

The fluorescence microscope 20 acquires an optical image of fluorescence emitted from the sample 1 under irradiation with the light from the light source 10, at a predetermined magnification, and feeds the image to the multiband camera 30. The fluorescence microscope 20 has a band-pass filter 22 for receiving the light from the light source 10, and a band-pass filter 24 for receiving the fluorescence emitted from the sample 1. The band-pass filter 22 is used for removing wavelength components unnecessary for excitation of a fluorescent dye contained in the sample 1, from the light of the light source 10. The band-pass filter 24 is used for interrupting light of wavelengths different from the fluorescence emitted from the fluorescent dye contained in the sample 1. The pair of these filters 22 and 24 are sometimes called a filter set.

The multiband camera 30 is an imaging device for receiving the optical image of fluorescence from the fluorescence microscope 20 to generate electric image data thereof. In the present embodiment the multiband camera 30 has three different detection wavelength bands and is sensitive to these detection wavelength bands. These detection wavelength bands normally correspond to R (red), G (green), and B (blue). In the description hereinafter, these detection wavelength bands will be referred to as the R wavelength band, the G wavelength band, and the B wavelength band. Portions of the detection wavelength bands overlap any adjacent bands. Namely, the R wavelength band and the G wavelength band overlap in part, and the G wavelength band and the B wavelength band also overlap in part. The multiband camera 30 includes three imaging devices (e.g., CCDs) corresponding to these detection wavelength bands, and a color separation prism for separating wavelength components of input light into the three detection wavelength bands and for feeding them to the corresponding imaging devices. In addition, the multiband camera 30 may include one imaging device (e.g., CCD) on which a color mosaic filter or the like is printed. The multiband camera 30 detects fluorescence images in the respective R, G, and B wavelength bands and generates R, G, and B outputs corresponding to those wavelength bands. The R, G, and B outputs are image data of the fluorescence images detected in the R, G, and B wavelength bands, respectively. The image data includes values indicating the intensities of fluorescence at respective pixels. Each pixel corresponds to one site in the sample 1.

As will be described later in detail, the multiband camera 30 has two operation modes. The first one is a High Light mode having a standard sensitivity characteristic, and the second a Low Light mode having the total sensitivity a little higher than the standard sensitivity. In the present embodiment the camera 30 operates only in the High Light mode.

The computer 40 is a device for controlling the measurement of fluorescent dyes by the measurement system 100. The computer 40 transmits a light-source switch signal to the light source 10 to control which is to be used out of the Xe lamp 10a and LED 10b. The computer 40 also functions as an arithmetic device for calculating the concentrations or respective fluorescent dyes in a target sample, using fluorescence image data of the target sample acquired by the multiband camera 30. The computer 40 has a storage device for storing software for this control and operation. This software may be read from a storage medium 46 into the storage device. The computer 40 executes the foregoing control and operation according to this software.

Figure 2:
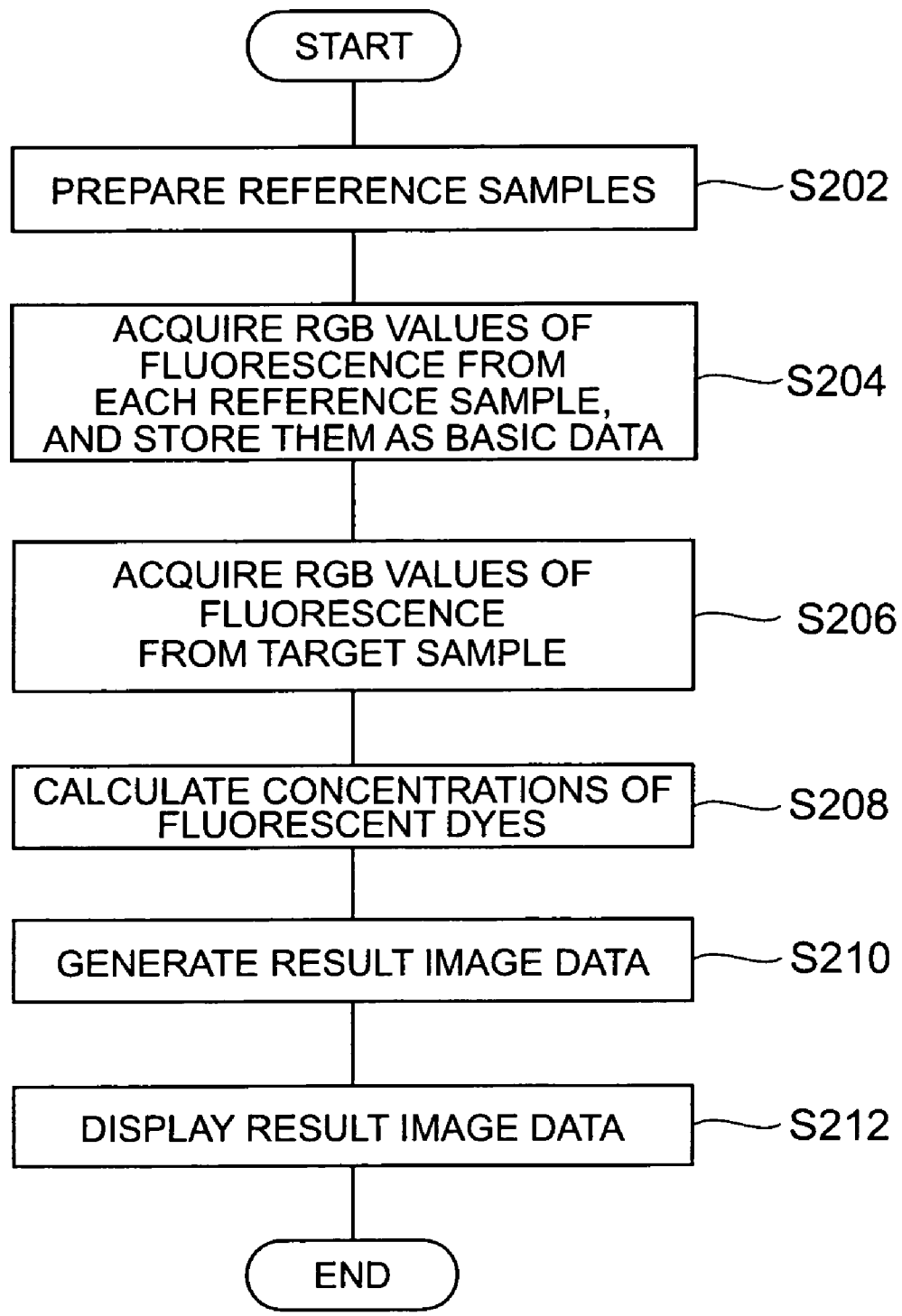
FIG. 2 is a flowchart showing a procedure of measuring the concentrations of fluorescent dyes.

A method of measuring the concentrations of fluorescent dyes in a target sample with the measurement system 100 will be described below with reference to FIG. 2. FIG. 2 is a flowchart showing the procedure of the measurement. This measurement method is roughly divided into two stages. The first stage corresponds to steps S202 and S204, and the second stage to steps S206-S212.

The first stage is to acquire data as a basis for the measurement. First, reference samples are prepared for acquiring this basic data (step S202). Each reference sample contains only one of the fluorescent dyes contained in the target sample respectively. Therefore, the reference samples are prepared as many as the fluorescent dyes in the target sample. Each reference sample contains a fluorescent dye at a predetermined concentration. In the description hereinafter, this concentration will be referred to as a unit concentration. A unit concentration of a fluorescent dye in one reference sample may be different from that in another reference sample.

The next step is to acquire fluorescence image data of each reference sample with the measurement system 100 (step S204). White light is emitted from the Xe lamp 10a and filtered by the band-pass filter 22. and each reference sample is illuminated with the filtered light through the band-pass filter 22. This excites the fluorescent dye in the reference sample to generate fluorescence. The light having passed the band-pass filter 22 has a wavelength spectrum that can excite all the reference samples.

The multiband camera 30 receives the fluorescence image of each reference sample through the fluorescence microscope 20 and converts it into image data. The fluorescence image is detected in each of the R, G, and B wavelength bands of the multiband camera 30. Therefore, the multiband camera 30 generates three image data acquired in the three detection wavelength bands, for one reference sample. The image data is fed to the computer 40 to be stored in the storage device in the computer 40. This is basic data acquired for one reference sample. The same measurement is carried out for all the reference samples and the basic data is stored. The first stage of the measurement is completed in this manner.

Each pixel in each basic data has a value indicating a fluorescence intensity measured using the multiband camera 30. Pixel values acquired in the R, G, and B wavelength bands are sometimes called R values, G values, and B values, respectively.

Figure 3:
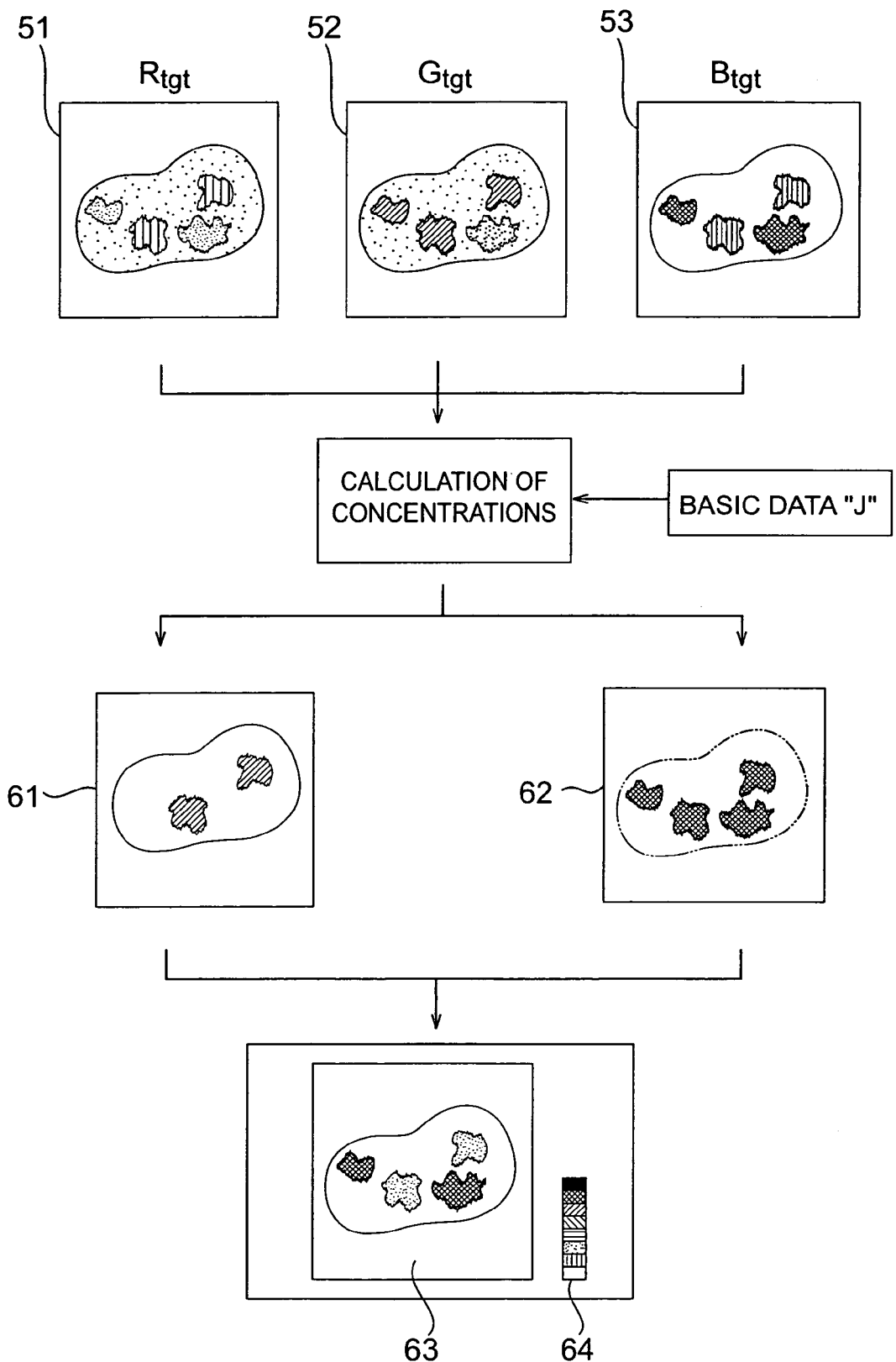
FIG. 3 is an illustration for explaining the second stage of measurement.

The second stage of the measurement will be described below wit reference to FIG. 3. The second stage is to calculate the concentrations of the respective fluorescent dyes in the target sample, using the basic data. First, the target sample is illuminated with the light from the Xe lamp 10a through the band-pass filter 22 to excite all the fluorescent dyes in the target sample, and to acquire a fluorescence image of the target sample (step S206). This step may be carried out continuously multiple times for measuring a change in cases where the concentration of the fluorescent dyes vary with time according to an active state of the target sample, e.g., a case where the target sample is a living cell. The intensity of the light emitted from the Xe lamp 10a is the same as that upon excitation of the reference samples for acquisition of the basic data. The multiband camera 30 receives the fluorescence image emitted from the sample 1, through the fluorescence microscope 20 and converts it into image data. The fluorescence image is detected in each of the R, G, and B wavelength bands of the multiband camera 30. Therefore, as shown in FIG. 3, the multiband camera 30 generates three image data 51-53 acquired in the three detection wavelength bands, for the target sample. The image data is fed to the computer 40. These image data will be sometimes called target data hereinafter.

Next, the computer 40 calculates the concentrations of the fluorescent dyes pixel by pixel, using the target data acquired at step S206 and the basic data acquired at step S204 (step S208). The following will describe measurement of the concentrations of the fluorescent dyes at a site in the target sample, for easier understanding of this measurement calculation. One site in the target sample corresponds to one pixel in the fluorescence image. It is assumed that the target sample contains two types of fluorescent dyes. In this case, two types of reference samples are prepared as well at step S202.

The computer 40 determines concentrations $c_1$ and $c_2$ of the first and second fluorescent dyes at a site in the target sample by an operation represented by a formula below. Units of the concentrations $c_1$ and $c_2$ are the aforementioned unit concentrations, i.e., the concentrations of the first and second fluorescent dyes in the first and second reference samples. Therefore, an actual concentration of the first fluorescent dye is a value obtained by multiplying the unit concentration of the first fluorescent dye by $c_1$, and an actual concentration of the second fluorescent dye a value obtained by multiplying the unit concentration of the second fluorescent dye by $c_2$. The same also applies to the other embodiments described hereinafter.

[Formula 7]

$$\begin{bmatrix} c_1 \\ c_2 \end{bmatrix} = (J^T \cdot J)^{-1} \cdot J^T \cdot \begin{bmatrix} R_{tgt} \\ G_{tgt} \\ B_{tgt} \end{bmatrix}, \quad (1)$$

$$J = \begin{bmatrix} Rf_1 & Rf_2 \\ Gf_1 & Gf_2 \\ Bf_1 & Bf_2 \end{bmatrix} \quad (2)$$

In this formula, matrix J represents the basic data acquired at step S204. $Rf_1$, $Gf_1$, and $Bf_1$ in the first column of the matrix J represent the R, G, and B values acquired at step S204 with the first reference sample containing only the first fluorescent dye. $Rf_2$, $Gf_2$, and $Bf_2$ in the second column of the matrix J represent the R, G, and B values acquired at step S204 with the second reference sample containing only the second fluorescent dye. $R_{tgt}$, $G_{tgt}$, and $B_{tgt}$ represent the R, G, and B values acquired at step S206 with the target sample. $J^T$ in Eq (1) represents a transpose of the matrix J. The above formula will be detailed later.

The computer 40 executes the operation of Eq (1) for all the pixels to determine the concentrations of the first and second fluorescent dyes pixel by pixel. This obtains concentration distribution data 61 and 62 of the two fluorescent dyes, as shown in FIG. 3.

Then the computer 40 generates image data for display of the measurement results using these concentration distribution data 61 and 62 (step S210). This image data indicates concentration distributions of the two fluorescent dyes on the target sample. This image data is fed to the display device 42. Through this, as shown in FIG. 3, an image 63 indicating the concentration distributions of the fluorescent dyes on the target sample is displayed along with a color bar 64 on the display device 42 (step S212). The computer 40 can also print out this 10 concentration distribution image 63 and color bar 64 by means of printer 44.

The foregoing Eqs (1) and (2) will be described below in detail. The intensity of fluorescence emitted from each fluorescent dye in the target sample increases in proportion to a concentration of the fluorescent dye. The addition theorem holds as to fluorescence emitted from multiple dyes. Therefore, R, G, and B values acquired at a certain pixel by the multiband camera 30 are expressed by the following equations.

$$R_{tgt} = \int_\lambda (f_{1\lambda} \cdot c_1 + f_{2\lambda} \cdot c_2) \cdot r_\lambda \, d\lambda \quad (3.1)$$

$$G_{tgt} = \int_\lambda (f_{1\lambda} \cdot c_1 + f_{2\lambda} \cdot c_2) \cdot g_\lambda \, d\lambda \quad (3.2)$$

$$B_{tgt} = \int_\lambda (f_{1\lambda} \cdot c_1 + f_{2\lambda} \cdot c_2) \cdot b_\lambda \, d\lambda \quad (3.3) \text{ [Formula 8]}$$

In these equations, $f_1$ and $f_2$ represent intensities of fluorescence emitted from the first and second fluorescent dyes in their unit concentration and $c_1$ and $c_2$ concentrations of the first and second fluorescent dyes in the target sample. $R_{tgt}$, $G_{tgt}$, and $B_{tgt}$ represent the R, G, and B values of the multiband camera 30 at a site in the target sample. Parameters r, g, and b represent the sensitivity characteristics of the multiband camera 30 in the R, G, and B wavelength bands. Subscript λ attached to the parameters $f_1$ and $f_2$ and r, g, and b indicates that these parameters are functions of wavelength.

Figure 9:
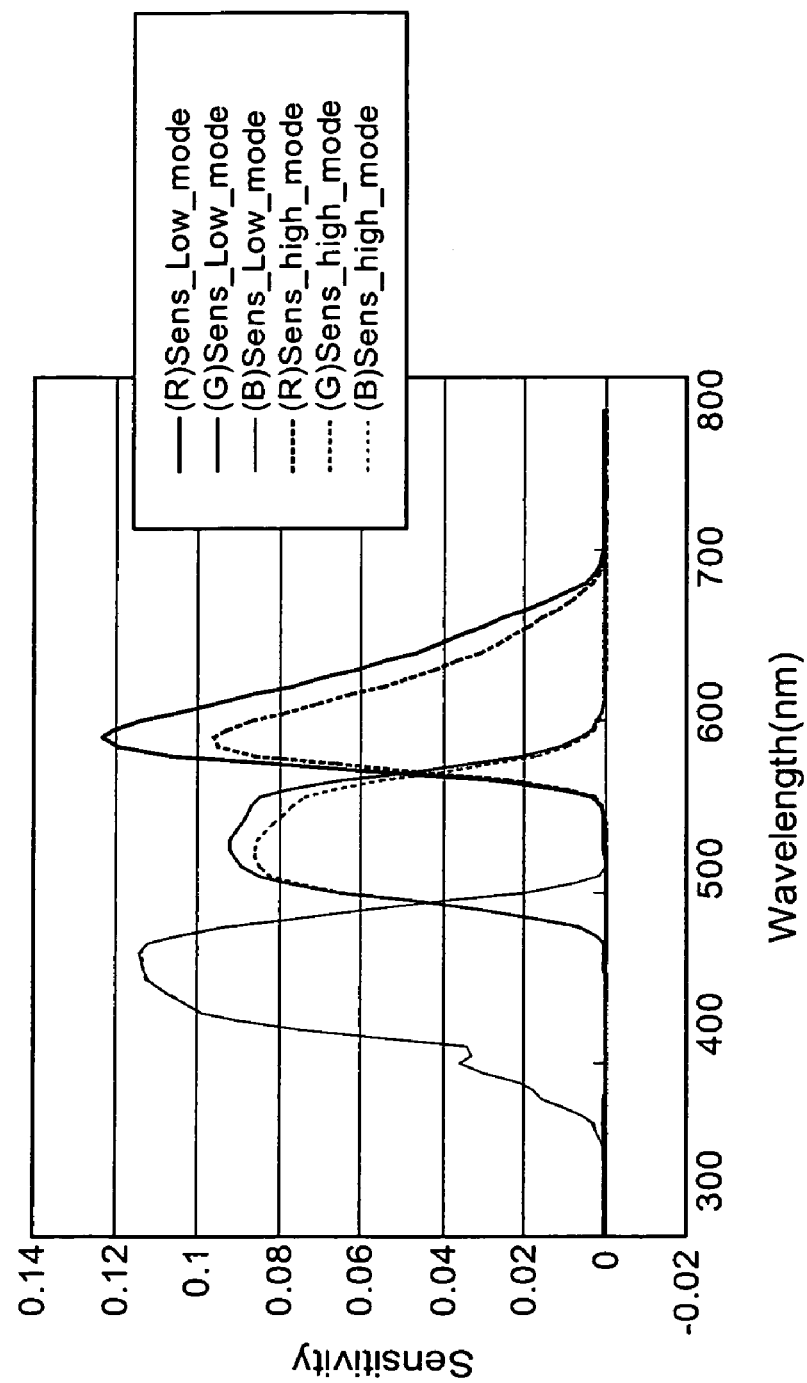
FIG. 9 is a diagram showing sensitivity characteristics of a 3-band camera.

$f_{1\lambda} \cdot c_{1\lambda}$ is the intensity of fluorescence with a certain wavelength emitted from the first fluorescent dye in the target sample. Similarly, $f_{2\lambda} \cdot c_{2\lambda}$ is the intensity of fluorescence with a certain wavelength emitted from the second fluorescent dye in the target sample. Since the addition theorem holds, the total intensity of fluorescence with a certain wavelength is $(f_{1\lambda} \cdot c_{1\lambda} + f_{2\lambda} \cdot c_{2\lambda})$. The multiband camera 30 detects this fluorescence intensity in each of the R, G, and B wavelength bands. As represented by Eq (3.1), the R value acquired from the target sample is a value obtained by multiplying the total fluorescence intensity at each wavelength $(f_{1\lambda} \cdot c_{1\lambda} + f_{2\lambda} \cdot c_{2\lambda})$ by a sensitivity characteristic $r_\lambda$ to the R wavelength band and integrating the product over the entire wavelength domain. Similarly, the G value or B value acquired from the target sample is a value obtained by multiplying the total fluorescence intensity $(f_{1\lambda} \cdot c_{1\lambda} + f_{2\lambda} \cdot c_{2\lambda})$ by a sensitivity characteristic $g_\lambda$ or $b_\lambda$ to the G wavelength band or B wavelength band and integrating the product over the entire wavelength domain. A described above, the R, G, and B values of the fluorescence from the target sample are values obtained by multiplying the fluorescence intensity at each wavelength by the sensitivity of the camera 30 corresponding to the wavelength and integrating the product over the entire wavelength domain. An example of the sensitivity characteristics of the multiband camera 30 is as shown in FIG. 9. This figure will be described later.

Eqs. (3.1)-(3.3) are rewritten into one matrix expression as follows.

[Formula 9]

$$\begin{bmatrix} R_{tgt} \\ G_{tgt} \\ B_{tgt} \end{bmatrix} = \begin{bmatrix} \left(\int_\lambda f_{1\lambda} \cdot r_\lambda \cdot d\lambda\right) \cdot c_1 + \left(\int_\lambda f_{2\lambda} \cdot r_\lambda \cdot d\lambda\right) \cdot c_2 \\ \left(\int_\lambda f_{1\lambda} \cdot g_\lambda \cdot d\lambda\right) \cdot c_1 + \left(\int_\lambda f_{2\lambda} \cdot g_\lambda \cdot d\lambda\right) \cdot c_2 \\ \left(\int_\lambda f_{1\lambda} \cdot b_\lambda \cdot d\lambda\right) \cdot c_1 + \left(\int_\lambda f_{2\lambda} \cdot b_\lambda \cdot d\lambda\right) \cdot c_2 \end{bmatrix} \quad (4)$$

Eq (4) is further rewritten as follows.

[Formula 10]

$$\begin{bmatrix} R_{tgt} \\ G_{tgt} \\ B_{tgt} \end{bmatrix} = \begin{bmatrix} \int_\lambda f_{1\lambda} \cdot r_\lambda \cdot d\lambda & \int_\lambda f_{2\lambda} \cdot r_\lambda \cdot d\lambda \\ \int_\lambda f_{1\lambda} \cdot g_\lambda \cdot d\lambda & \int_\lambda f_{2\lambda} \cdot g_\lambda \cdot d\lambda \\ \int_\lambda f_{1\lambda} \cdot b_\lambda \cdot d\lambda & \int_\lambda f_{2\lambda} \cdot b_\lambda \cdot d\lambda \end{bmatrix} \cdot \begin{bmatrix} c_1 \\ c_2 \end{bmatrix} \quad (5)$$

As represented by Eq (5), the R, G, and B values of fluorescence from the target sample are calculated by multiplying the matrix J below by a concentration matrix of the fluorescent dyes.

[Formula 11]

$$J = \begin{bmatrix} \int_\lambda f_{1\lambda} \cdot r_\lambda \cdot d\lambda & \int_\lambda f_{2\lambda} \cdot r_\lambda \cdot d\lambda \\ \int_\lambda f_{1\lambda} \cdot g_\lambda \cdot d\lambda & \int_\lambda f_{2\lambda} \cdot g_\lambda \cdot d\lambda \\ \int_\lambda f_{1\lambda} \cdot b_\lambda \cdot d\lambda & \int_\lambda f_{2\lambda} \cdot b_\lambda \cdot d\lambda \end{bmatrix} \quad (6)$$

The three components in the first column in the matrix J are the R, G, and B values obtained by measuring the fluorescense intensities in the unit concentration of the first fluorescent dye using the multiband camera 30. These are equivalent to the aforementioned $Rf_1$, $Gf_1$, and $Bf_1$ obtained by the measurement of the first reference sample. Similarly, the three components in the second column in the matrix J are the R, G, and B values obtained by measuring the fluorescence intensities in the unit concentration of the second fluorescent dye using the multiband camera 30, and these are equivalent to the aforementioned $Rf_2$, $Gf_2$, and $Bf_2$ obtained by the measurement of the second reference sample. Therefore, all the components in the matrix J can be determined by measuring the fluorescence emitted from these reference samples, using the multiband camera 30. Namely, the matrix J is equivalent to the basic data acquired at step S204.

By modifying Eq (5), we obtain the aforementioned Eq (1). The computer 40 executes the aforementioned operation of Eq (1) using the basic data J, to calculate the concentrations $c_1$ and $c_2$ of the fluorescent dyes at each pixel. The concentrations of the fluorescent dyes contained at one site in the target sample are measured in this manner.

The above Eqs (1) and (2) are rewritten into more general forms as follows.

[Formula 12]

$$\begin{bmatrix} c_1 \\ c_2 \\ \vdots \\ c_m \end{bmatrix} = (J^T \cdot J)^{-1} \cdot J^T \cdot \begin{bmatrix} O_1 \\ O_2 \\ \vdots \\ O_k \end{bmatrix}, \quad (7)$$

$$J = \begin{bmatrix} J_{11} & J_{12} & \cdots & J_{1m} \\ J_{21} & J_{22} & \cdots & J_{2m} \\ \vdots & \vdots & & \vdots \\ J_{k1} & J_{k2} & \cdots & J_{km} \end{bmatrix} \quad (8)$$

It is assumed herein that the target sample contains the first to mth (where m is an integer of 2 or more) fluorescent dyes and the multiband camera has the first to kth (where k is an integer of 2 or more) different detection wavelength bands. Each of $O_1$-$O_k$ is the value of a pixel in the fluorescence image of the target sample taken in each of the first to kth detection wavelength bands using the multiband camera. J represents a k×m matrix, and component $J_{ij}$ in the ith row and jth column (where i is any integer from 1 to k, and j any integer from 1 to m) in J represents a measured intensity in the jth detection wavelength band of the flourescence emitted from the jth reference sample.

In the present embodiment, $J_{ij}$ represents the value of the same pixel in the fluorescence image of the jth reference sample taken in the ith detection, wavelength band using the multiband camera as those for $O_1$-$O_k$. However, $J_{ij}$ does not always have to be the value of the same pixel as those for $O_1$-$O_k$. For example, if a reference sample emits fluorescence at a certain site only, it is possible to adopt a method of defining the value of an arbitrary pixel corresponding to the site as $J_{ij}$ and to use this $J_{ij}$ commonly in the measurement operation for all the pixels. In this case, the pixel of $J_{ij}$ does not always agree with the pixels for $O_1$-$O_k$.

Figure 4:
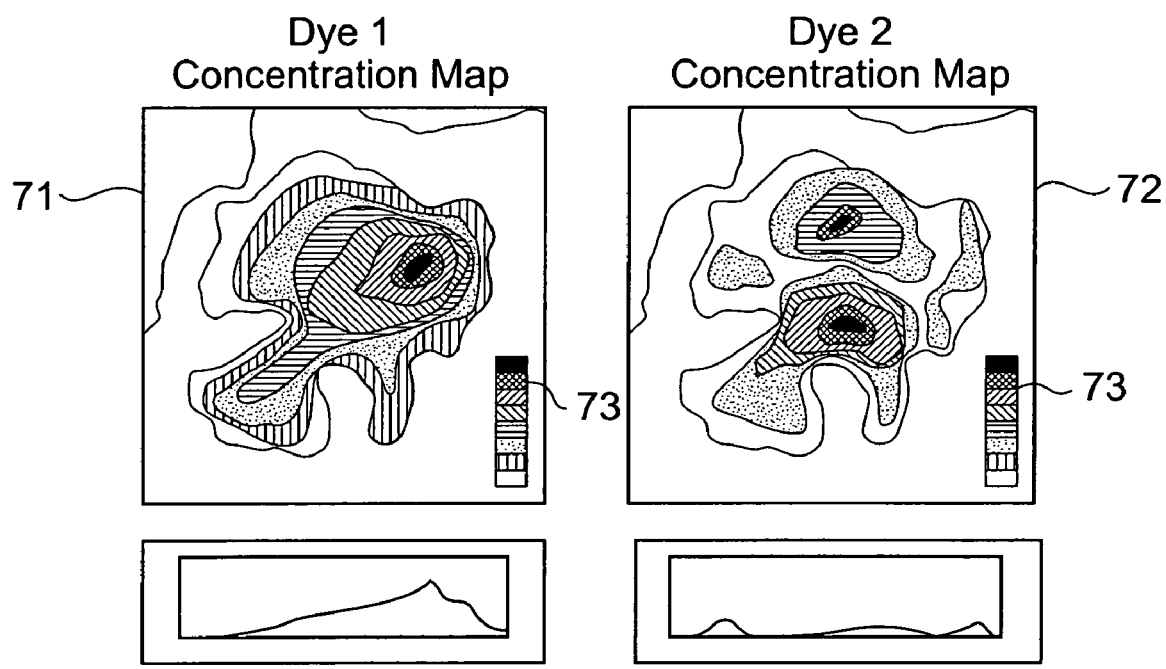
FIG. 4 is an illustration to illustrate an example of an expression method of measurement results.
Figure 5:
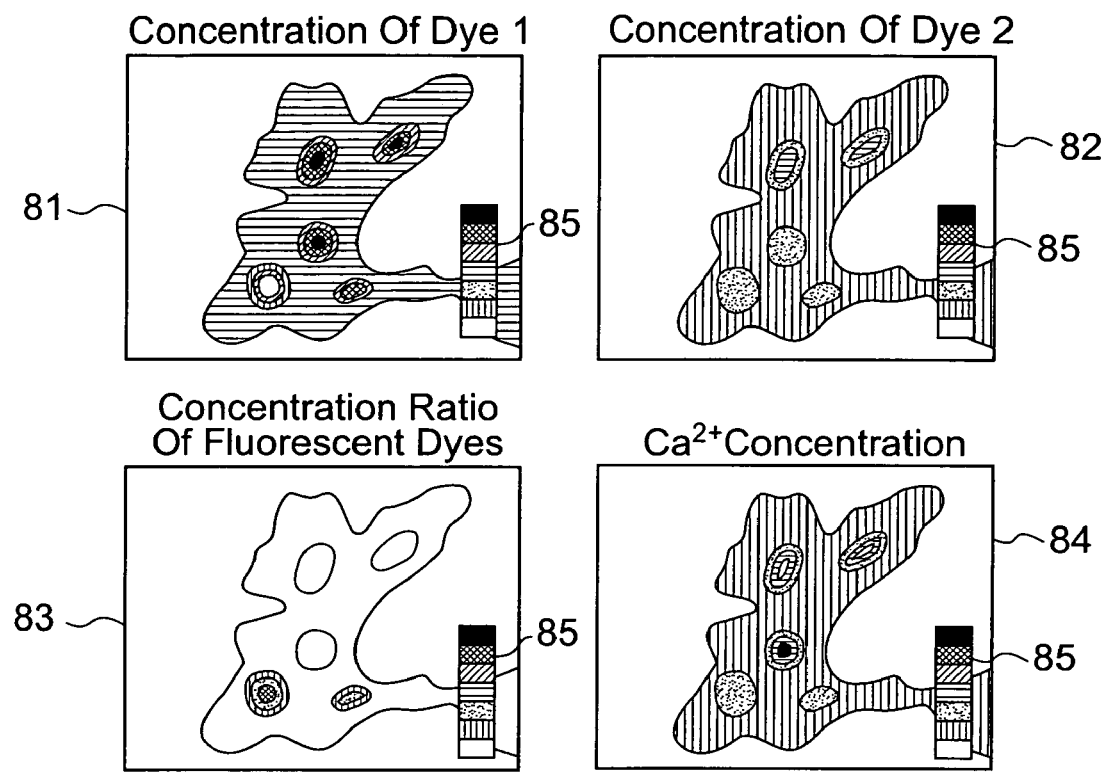
FIG. 5 is an illustration to illustrate an example of an expression method of measurement results.

Next, how to express the measurement results will be described. There are a variety of expression methods of the measurement results, and the following will describe some specific examples. FIG. 4 shows an example of an expression method. This method is to express concentration distributions of two fluorescent dyes in a target sample, as monochrome images 71 and 72. In the images 71 and 72, the concentrations of the fluorescent dyes are expressed by luminances. A monochrome bar 73 is also displayed along with the concentration distribution in each image. As shown in FIG. 5, the concentration distribution of each fluorescent dye may be displayed using pseudocolors. FIG. 5 will be described later in more detail. For clarifying the difference between the distributions of the hero fluorescent dyes, it is also possible to adopt a method of calculating a ratio of the concentration of these fluorescent dyes and displaying a concentration ratio distribution as a monochrome image or as an image using the pseudocolors.

Figure 6:
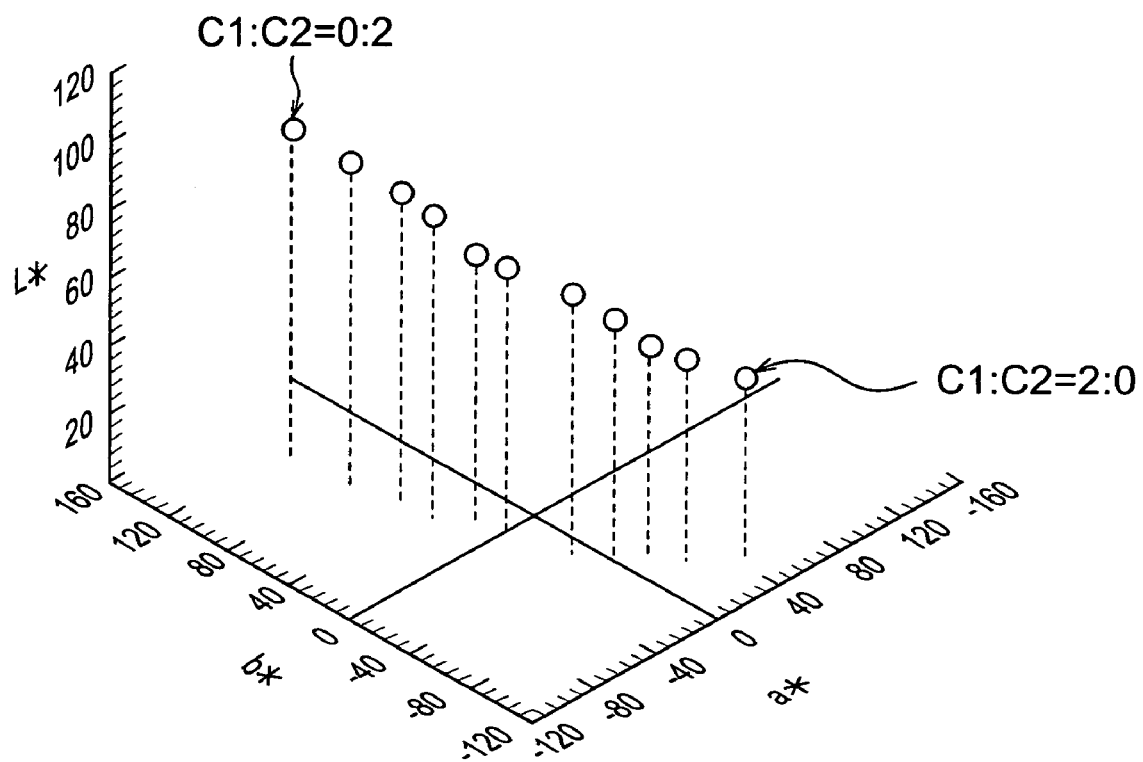
FIG. 6 is an illustration to illustrate an example of an expression method of measurement results.

Another method of expressing the measurement results is to plot the concentrations of the fluorescent dyes at all the pixels in a color 3D space. FIG. 6 shows an example of an expression method using the color 3D space. In this example, the concentrations of the fluorescent dyes are plotted in the L*a*b* being a uniform color space. In FIG. 6 the a* axis represents a color corresponding to the first fluorescent dye, and the b* axis a color corresponding to the second fluorescent dye. In addition, the L* axis represents brightness. A two-dimensional location in FIG. 6 represents a concentration ratio of the two fluorescent dyes.

The following will describe the advantages of the present embodiment in comparison with the conventional technology. The conventional technology uses a combination of a filter for extracting a wavelength component used in excitation of one fluorescent dye from output light of a light source with a filter for extracting a wavelength component corresponding to the fluorescent dye from fluorescence emitted from a sample, i.e., a filter set. This filter set is prepared for each fluorescent dye and is set in a fluorescence microscope. For example, filter sets to be prepared include a filter set for mainly observing blue fluorescence by ultraviolet excitation, a filter set for mainly observing green fluorescence by blue excitation, and a filter set for mainly observing red fluorescence by green excitation. While appropriately switching among these filter sets, fluorescence images from the respective fluorescent dyes are taken with a monochrome camera. Values of respective pixels are handled as data indicating the concentrations of the fluorescent dyes.

However, if fluorescence spectra of a plurality of fluorescent dyes overlap, fluorescence from these dyes cannot be perfectly separated by the band-pass filter. Therefore, the accuracy of the measurement is low where the overlap of the fluorescence spectra is large. In addition, the fluorescence images need to be acquired while repeatedly switching among the filter sets. For this reason, it is impossible to simultaneously measure the concentrations of a plurality of fluorescent dyes. This is a problem in cases where the target is a living sample. Furthermore, a slight change can occur in the optical system on the occasion of switching among the filter sets, and it could cause a difference in the accuracy of the measurement among the plurality of fluorescent dyes.

In contrast, the present embodiment involves calculating the concentrations of the fluorescent dyes through the use of the calculation expression not affected by the overlap between the fluorescence spectra of the fluorescent dyes. Thus, the concentrations of the fluorescent dyes can be accurately determined, regardless of the presence/absence of the overlap between the fluorescence spectra. This will become clearer with reference to the examples described later.

The present embodiment is arranged to perform the measurement by acquiring the fluorescence image of the target sample using the multiband camera 30 without switching among the filter sets. For this reason, the method of the present embodiment is able to simultaneously determine the concentrations of the multiple fluorescent dyes and, therefore, is also suitably applicable to cases where the target is a living sample. Furthermore, the present embodiment requires no change of the optical system during the measurement and is thus able to determine the concentrations of the multiple fluorescent dyes with uniform accuracy. Therefore, the method of the present embodiment obtains the concentrations of the fluorescent dyes with high reliability.

Second Embodiment

As shown in FIG. 1, a fluorescent dye measurement system 200 of the present embodiment has a spectrometer 35 in addition to the configuration of the above-described measurement system 100. The spectrometer 35 is arranged to be able to receive a fluorescence image acquired with the fluorescence microscope 20. The fluorescence microscope 20 may have an optical element for feeding the fluorescence image to both of camera 30 and spectrometer 35, e.g., a half mirror. In another configuration, the spectrometer 35 may be set so as to be replaced with the camera 30.

The present embodiment is different in the acquisition method of basic data at the aforementioned step S204 from the first embodiment. Namely, the present embodiment is arranged to acquire the basic data with the spectrometer 35, instead of the multiband camera 30. In this case, the same advantages as in the first embodiment can be enjoyed. The other measurement procedure in the present embodiment is much the same as in the first embodiment.

The basic data J acquired using the multiband camera 30 is the pixel values acquired by measuring the fluorescence from the reference samples in each of the R, G, and B wavelength bands of the multiband camera 30, as represented by the aforementioned Eq (2). As represented by the aforementioned Eq (6), these pixel values are the values obtained by multiplying the fluorescent intensity at each wavelength of the fluorescent dye in the unit concentration by the sensitivity characteristic of the camera corresponding to the wavelength and integrating the product over the entire wavelength domain. This integration can be approximately rewritten as follows.

[Formula 13]

$$J \approx \begin{bmatrix} r_{\lambda 1} & r_{\lambda 2} & r_{\lambda 3} & \cdots & r_{\lambda n} \\ g_{\lambda 1} & g_{\lambda 2} & g_{\lambda 3} & \cdots & g_{\lambda n} \\ b_{\lambda 1} & b_{\lambda 2} & b_{\lambda 3} & \cdots & b_{\lambda n} \end{bmatrix} \cdot \begin{bmatrix} f_{1\lambda 1} & f_{2\lambda 1} \\ f_{1\lambda 2} & f_{2\lambda 2} \\ f_{1\lambda 3} & f_{2\lambda 3} \\ \vdots & \vdots \\ f_{1\lambda n} & f_{2\lambda n} \end{bmatrix} = Js \quad (9)$$

In this expression, $\lambda 1, \lambda 2, \ldots \lambda n$ represents spectral wavelength bands obtained by dividing the entire wavelength domain by an arbitrary width. n is an integer of 2 or more and represents the number of spectral wavelength bands. $r_{\lambda,t}$, $g_{\lambda,t}$, and $b_{\lambda,t}$ (t is an integer of 1-n) represent the R, G, and B sensitivity characteristics of the multiband camera 30 in the spectral wavelength band $\lambda t$. $f_{1\lambda,t}$ and $f_{2\lambda,t}$ represent the intensities in the spectral wavelength band $\lambda t$ of the fluorescence emitted from the first and second fluorescent dyes in their unit concentration. It is assumed in Eq (9) that the R, G, and B sensitivity characteristics and the fluorescence intensities in the unit concentrations of the first and second fluorescent dyes have constant values in each spectral wavelength band.

The fluorescence intensities in the unit concentrations of the first and second fluorescent dyes in these spectral wavelength bands can be measured using the spectrometer 35. Namely, by detecting the fluorescence emitted from the first and second reference samples with the spectrometer 35, the fluorescence intensities $f_{1\lambda 1}, f_{1\lambda 2} \ldots f_{1\lambda n}$ and $f_{2\lambda 1}, f_{2\lambda 2}, \ldots f_{2\lambda n}$ in the unit concentrations of the first and second fluorescent dyes in the spectral wavelength bands $\lambda 1, \lambda 2, \ldots \lambda n$ are acquired. These are spectral data represented by the second term on the right-hand side of Eq (9).

In the present embodiment the computer 40 stores the spectral sensitivity characteristics of the multiband camera 30 corresponding to the first term on the right-hand side of Eq (9) in the storage device. When the computer 40 acquires the spectral data from each reference sample with the spectrometer 35, it executes the aforementioned operation of Eq (9) to calculate the matrix Js represented by Eq (9).

This matrix Js and the matrix J being the basic data ideally agree with each other. In practice, however, coefficients for calibration and coefficients for reduction of error in correlation are necessary for correlating the multiband camera 30 with the spectrometer 35. For this reason, an expression of a coefficient is necessary between the matrices J and Js. Therefore, the relation between J and Js is expressed as follows.

$$J = a \cdot Js \quad (10) \text{ [Formula 14]}$$

In this equation a represents a constant for correction. The constant a is determined by detecting the white light from the Xe lamp 10a with each of the multiband camera 30 and spectrometer 35 through an ND filter and calculating a ratio of light intensities measured.

As described above, the computer 40 executes the operations represented by Eqs (9) and (10) using the spectral data acquired with the spectrometer 35 and the spectral sensitivity characteristic of the multiband camera 30 to calculate the basic data J. This basic data J is used commonly in calculation of the fluorescent dye concentrations at all the pixels. In this case the concentrations of the fluorescent dyes can also be measured with good accuracy.

As represented by Eq (9) and Eq (10), the R, G, and B values of the multiband camera 30 can be calculated using the spectral data acquired with the spectrometer 35 and the sensitivity characteristic of the multiband camera 30. In more general description, the R, G, and B values of the multiband camera 30 and the R, G, and B values calculated using the spectral data of the spectrometer 35 can be mutually transformed using the constant a. Therefore, the concentrations of the fluorescent dyes can also be determined without the use of the camera 30 by measuring the fluorescence from the target sample as well as those from the reference samples with the spectrometer 35 to acquire spectral data, calculating the R, G, and B values from the spectral data, and performing the aforementioned calculation of Eq (1). It is, however, noted that the spectrometer 35 acquires the spectral data at only one site in a sample at a time. For this reason, a distribution of the concentrations of the fluorescent dyes can be more efficiently determined by taking the fluorescence image of the target sample using the imaging device such as the multiband camera 30.

It is assumed in the above description that the types of the fluorescent dyes in the target sample are preliminarily known. However, even in cases where the fluorescent dyes in the target sample are unknown, it is also possible to specify the types of the fluorescent dyes and then to measure the concentrations thereof. In this case, the basic data is preliminarily acquired by measuring spectra of various known fluorescent dyes in advance or by acquiring publicly known spectra in advance. The basic data is stored in the storage device in the computer 40. The computer 40 performs the aforementioned calculation of Eq (1), using the spectral data acquired from a site in the target sample with the spectrometer and the basic data of one or more arbitrary fluorescent dye. Then the computer 40 calculates a spectrum on the assumption that the target sample contains the fluorescent dye corresponding to the used basic data, using the calculated concentration values. The computer 40 compares this simulated spectrum with the spectrum of the target sample actually measured with the spectrometer, and determines whether a degree of Fitting between them is not less than a predetermined threshold. The computer 40 searches for a fluorescent dye to provide a simulated spectrum adequately close to the actually measured spectrum in accordance with such a determination algorithm, to specify the fluorescent dye contained in the target sample. Once the fluorescent dye is specified, the concentrations of the fluorescent dye on all the pixels can be calculated by the method of the first embodiment.

Even in the case where the known spectra are not prepared as the basic data, the concentration calculation can also be performed by analyzing the principal components in a measurement system of a target sample group and performing the calculation using the principal component spectra of the results of the analysis as reference spectra. Namely, without the basic dye prepared in advance for the purpose of estimation as described above, it is also possible to form an ideal reference spectrum considered to a principal component on a component basis out of a sample group and to perform the measurement calculation based thereon. For this reason, for example, it is also possible to quantify a component of fluorescence emitting substance that a sample itself has. In addition, it is also possible to perform a combinational calculation of this with the aforementioned one.

Third Embodiment

The present embodiment concerns the measurement where the target sample contains four or more types of fluorescent dyes. In cases where four or more types of fluorescent dyes are contained, the concentrations of the fluorescent dyes can be measured up to the same number as the number of detection wavelength bands if the number of detection wavelength bands of the multiband camera is increased according to the number of fluorescent dyes. In practice, a 4-band multicamera can be obtained by using the optical system described in "NHK STRL R&D" (No. 52, pp. 53-60, 1998). It is, however, difficult to devise an optical system for implementing a 5-band or 6-band camera.

In the present embodiment, therefore, four or more types of fluorescent dyes are measured with a 3-band camera 30 as in the first and second embodiments. As described previously, the multiband camera 30 has the two sensitivity modes, the Low Light mode and the High Light mode. High Light mode is a mode in which the standard sensitivity characteristic is set in each detection wavelength band, and the Low Light mode a mode in which a sensitivity characteristic a little higher over all sensitivities than that in the High Light mode is set in each detection wavelength band. In both of the Low Light mode and the High Light mode, portions of the detection wavelength bands overlap any adjacent bands. This multiband camera 30 has two analog circuits having different gains in all the detection wavelength bands. A circuit with a low gain in the entire detection wavelength band is used in the High Light mode, and a circuit with a high gain in the entire detection wavelength band is used in the Low Light mode.

Let $R_{tgt-l}$, $G_{tgt-l}$, and $B_{tgt-l}$ be R, G, and B values in the Low Light mode of the multiband camera 30, and $R_{tgt-h}$, $G_{tgt-h}$, and $B_{tgt-h}$ be R, G, and B values in the High Light mode, and then the following equation holds.

[Formula 15]

$$\begin{bmatrix} R_{tgt-l} \\ G_{tgt-l} \\ B_{tgt-l} \\ R_{tgt-h} \\ G_{tgt-h} \\ B_{tgt-h} \end{bmatrix} = \begin{bmatrix} \int_\lambda f_1 \cdot r_l \cdot d\lambda & \int_\lambda f_2 \cdot r_l \cdot d\lambda & \dots & \int_\lambda f_6 \cdot r_l \cdot d\lambda \\ \int_\lambda f_1 \cdot g_l \cdot d\lambda & \int_\lambda f_2 \cdot g_l \cdot d\lambda & \dots & \int_\lambda f_6 \cdot g_l \cdot d\lambda \\ \int_\lambda f_1 \cdot b_l \cdot d\lambda & \int_\lambda f_2 \cdot b_l \cdot d\lambda & \dots & \int_\lambda f_6 \cdot b_l \cdot d\lambda \\ \int_\lambda f_1 \cdot r_h \cdot d\lambda & \int_\lambda f_2 \cdot r_h \cdot d\lambda & \dots & \int_\lambda f_6 \cdot r_h \cdot d\lambda \\ \int_\lambda f_1 \cdot g_h \cdot d\lambda & \int_\lambda f_2 \cdot g_h \cdot d\lambda & \dots & \int_\lambda f_6 \cdot g_h \cdot d\lambda \\ \int_\lambda f_1 \cdot b_h \cdot d\lambda & \int_\lambda f_2 \cdot b_h \cdot d\lambda & \dots & \int_\lambda f_6 \cdot b_h \cdot d\lambda \end{bmatrix} \cdot \begin{bmatrix} c_1 \\ c_2 \\ c_3 \\ c_4 \\ c_5 \\ c_6 \end{bmatrix} \quad (11)$$

In this equation, $r_l$, $g_l$, and $b_l$ represent sensitivity characteristics of the R, G, and B wavelength bands in the Low Light mode of the multiband camera 30, and $r_h$, $g_h$, and $b_h$ sensitivity characteristics of the R, G, and B wavelength bands in the High Light mode of the multiband camera 30.

The 6×6 matrix of the first term on the right-hand side in Eq (11) is the basic data $J_1$ in the present embodiment. Namely, the following equation holds.

[Formula 16]

$$J_1 = \begin{bmatrix} \int_\lambda f_1 \cdot r_l \cdot d\lambda & \int_\lambda f_2 \cdot r_l \cdot d\lambda & \dots & \int_\lambda f_6 \cdot r_l \cdot d\lambda \\ \int_\lambda f_1 \cdot g_l \cdot d\lambda & \int_\lambda f_2 \cdot g_l \cdot d\lambda & \dots & \int_\lambda f_6 \cdot g_l \cdot d\lambda \\ \int_\lambda f_1 \cdot b_l \cdot d\lambda & \int_\lambda f_2 \cdot b_l \cdot d\lambda & \dots & \int_\lambda f_6 \cdot b_l \cdot d\lambda \\ \int_\lambda f_1 \cdot r_h \cdot d\lambda & \int_\lambda f_2 \cdot r_h \cdot d\lambda & \dots & \int_\lambda f_6 \cdot r_h \cdot d\lambda \\ \int_\lambda f_1 \cdot g_h \cdot d\lambda & \int_\lambda f_2 \cdot g_h \cdot d\lambda & \dots & \int_\lambda f_6 \cdot g_h \cdot d\lambda \\ \int_\lambda f_1 \cdot b_h \cdot d\lambda & \int_\lambda f_2 \cdot b_h \cdot d\lambda & \dots & \int_\lambda f_6 \cdot b_h \cdot d\lambda \end{bmatrix} \quad (12)$$

The six components in the first column of the matrix $J_1$ represent the R, G, and B values of the multiband camera 30 obtained by measuring intensities of the fluorescence in the unit concentration of the first fluorescent dye in the Low Light mode and in the High Light mode of the multiband camera 30. Similarly, the six components in each of the second to sixth columns of the matrix $J_1$ represent the R, G, and B values of the multiband camera 30 obtained by measuring intensities of fluorescence in the unit concentration of each of the second to sixth fluorescent dyes in the Low Light mode and in the High Light mode of the multiband camera 30. Therefore, all the components in the matrix $J_1$ can be determined by measuring the fluorescence emitted from the first to sixth reference samples in both of the Low Light mode and the High Light mode of the multiband camera 30.

Eq (11) can be rewritten as follows.

[Formula 17]

$$\begin{bmatrix} c_1 \\ c_2 \\ c_3 \\ c_4 \\ c_5 \\ c_6 \end{bmatrix} = (J_1^T \cdot J_1)^{-1} \cdot J_1^T \cdot \begin{bmatrix} R_{tgt-l} \\ G_{tgt-l} \\ B_{tgt-l} \\ R_{tgt-h} \\ G_{tgt-h} \\ B_{tgt-h} \end{bmatrix} \quad (13)$$

Therefore, the concentrations of at most six types of fluorescent dyes can be calculated by measuring fluorescence from the reference samples to acquire the basic data $J_1$, thereafter detecting fluorescence from the target sample in both of the Low Light mode and the High Light mode of the multiband camera 30, and substituting obtained R, G, and B values into Eq (13).

This embodiment is arranged to quantify the fluorescent dyes up to six types with the use of the 3-band camera, and if a 4-band camera is used, the same technique allows us to quantify the fluorescent dyes up to eight types. More generally, it is possible to quantify the fluorescent dyes up to a number resulting from multiplication of the number of detection wavelength bands of the multiband camera by the number of sensitivity characteristics of the multiband camera.

The foregoing Eqs (13) and (12) can be rewritten into more general forms as follows.

[Formula 18]

$$\begin{bmatrix} c_1 \\ c_2 \\ \vdots \\ c_m \end{bmatrix} = (J_1^T, J_1)^{-1} \cdot J_1^T \cdot \begin{bmatrix} P_1 \\ P_2 \\ \vdots \\ P_q \end{bmatrix}, \quad (14)$$

$$P_v = \begin{bmatrix} P_{1v} \\ P_{2v} \\ \vdots \\ P_{kv} \end{bmatrix} \quad (15)$$

$$J_1 = \begin{bmatrix} L_{11} & L_{12} & \cdots & L_{1m} \\ L_{21} & L_{22} & \cdots & L_{2m} \\ \vdots & \vdots & & \vdots \\ L_{q1} & L_{q2} & \cdots & L_{qm} \end{bmatrix}, \quad (16)$$

$$L_{vj} = \begin{bmatrix} L_{1vj} \\ L_{2vj} \\ \vdots \\ L_{kvj} \end{bmatrix} \quad (17)$$

It is assumed herein that the target sample contains the first to mth (where m is an integer of 2 or more) fluorescent dyes and that the multiband camera has the first to kth (where k is an integer of 2 or more) different detection wavelength bands and the first to qth (q is an integer of 2 or more) sensitivity modes for setting different sensitivity characteristics for the first to kth detection wavelength bands. The component matrices $P_1$-$P_k$ represent k×1 matrices. A component $P_{iv}$ in the ith row (v is any integer from 1 to q, and i any integer from 1 to k) in the matrix $P_v$ represents the value of a pixel in the fluorescence image of the target sample taken in the ith detection wavelength band and in the vth sensitivity mode using the multiband camera. $J_1$ is a (k·q)×m matrix, and a component $L_{ivj}$ in the ith row in a component matrix $L_{vj}$ (where j is any integer from 1 to m) in $J_1$ represents the value of the same pixel as that for $P_{iv}$ in the fluorescence image of the jth reference sample taken in the ith detection wavelength band and in the vth sensitivity mode of the multiband camera.

Fourth Embodiment

The present embodiment concerns a measurement where the target sample contains four or more types of fluorescent dyes as the third embodiment did. In the third embodiment, the two types of sensitivity modes of the multiband camera were prepared to enable the measurement of the fluorescent dyes up to twice the number of detection wavelength bands. In contrast to it, the present embodiment is arranged to excite a sample by plural types of excitation beams with different wavelength spectra, thereby enabling the measurement of fluorescent dyes up to (the number of detection wavelength bands)×(the number of types of excitation beams).

More specifically, the present embodiment uses the multicolor emission type LED 10b as a light source for exciting the sample. This LED 10b can emit plural types of output beams with different principal wavelengths. Every type of output beam has a wavelength spectrum that can excite all the fluorescent dyes contained in the target sample. The basic data is acquired based on the fluorescence emitted by illuminating each reference sample with each output beam to excite the fluorescent dye. The basic data may be acquired by taking fluorescence images using the multiband camera as in the first embodiment, or may be calculated using the spectral data of the spectrometer as in the second embodiment.

Similarly, the target data is also acquired by illuminating the target sample with each output beam from the LED 10b to excite the fluorescent dyes and taking the fluorescence images with the camera 30. With different wavelength characteristics of excitation beams, a fluorescent dye also emits its fluorescence with different wavelength characteristics. Therefore, if the basic data and target data is acquired with switching among the principal wavelengths of the output beams from the LED 10b, it becomes feasible to measure the fluorescent dyes up to a number resulting from multiplication of the number of detection wavelength bands of the multiband camera 30 by the number of types of excitation beams. For example, at most six types of fluorescent dyes can be measured with two types of wavelength characteristics of excitation beams, and at most nine types of fluorescent dyes can be measured with three types of wavelength characteristics.

In general, the computer 40 executes an operation represented by the following formula to calculate the concentrations of the respective fluorescent dyes.

[Formula 19]

$$\begin{bmatrix} c_1 \\ c_2 \\ \vdots \\ c_m \end{bmatrix} = (J_2^T \cdot J_2)^{-1} \cdot J_2^T \cdot \begin{bmatrix} Q_1 \\ Q_2 \\ \vdots \\ Q_r \end{bmatrix}, \quad (18)$$

-continued $$Q_u = \begin{bmatrix} Q_{1u} \\ Q_{2u} \\ \vdots \\ Q_{ku} \end{bmatrix} \quad (19)$$

$$J_2 = \begin{bmatrix} T_{11} & T_{12} & \cdots & T_{1m} \\ T_{21} & T_{22} & \cdots & T_{2m} \\ \vdots & \vdots & & \vdots \\ T_{r1} & T_{r2} & \cdots & T_{rm} \end{bmatrix}, \quad (20)$$

$$T_{uj} = \begin{bmatrix} T_{1uj} \\ T_{2uj} \\ \vdots \\ T_{kuj} \end{bmatrix} \quad (21)$$

It is assumed herein that the target sample contains the first to mth (where m is an integer of 2 or more) fluorescent dyes and that the multiband camera has the first to kth (where k is an integer of 2 or more) different detection wavelength bands. The component matrices $Q_1$-$Q_k$ are k×1 matrices. Component $Q_{iu}$ in the ith row (where i is any integer from 1 to k) in the matrix $Q_u$ (where u is any integer from 1 to r) represents the value of a pixel in a fluorescence image of the target sample taken in the ith detection wavelength band upon illuminating the target sample with the uth excitation beam. $J_2$ represents a (k·r)×m matrix, and component $T_{iuj}$ in the ith row in a component matrix $T_{uj}$ (where j is any integer from 1 to m) in $J_2$ represents the value of the same pixel as that for $Q_{iu}$ in a fluorescence image of the jth reference sample taken in the ith detection wavelength band of the multiband camera when the jth reference sample is illuminated with the uth excitation beam.

The present embodiment uses the multicolor emission type LED 10b but it is also possible to use a plurality of light sources (LEDs or the like) for emitting beams of different wavelength spectra, instead thereof. In addition, the LED 10b may be replaced by a light source with variable output wavelengths. For example, it is possible to use a light source 10c for extracting a specific wavelength component from the output light of the Xe lamp by means of a monochrometer and emitting it, or a light source 10d for extracting a specific wavelength component from the output light of the Xe lamp by means of a wavelength filter and emitting it.

Fifth Embodiment

The present embodiment is different in the optical device used in the acquisition of the basic data and target data from the above-described embodiments. The above-described embodiments are arranged to acquire the basic data by means of the multiband camera or the spectrometer, whereas the present embodiment is arranged to acquire the basic data by means of a plurality of band-pass filters and a monochrome camera. The above-described embodiments are arranged to acquire the target data by means of the multiband camera, whereas the present embodiment is arranged to acquire the target data by means of a plurality of band-pass filters and a monochrome camera.

Figure 7:
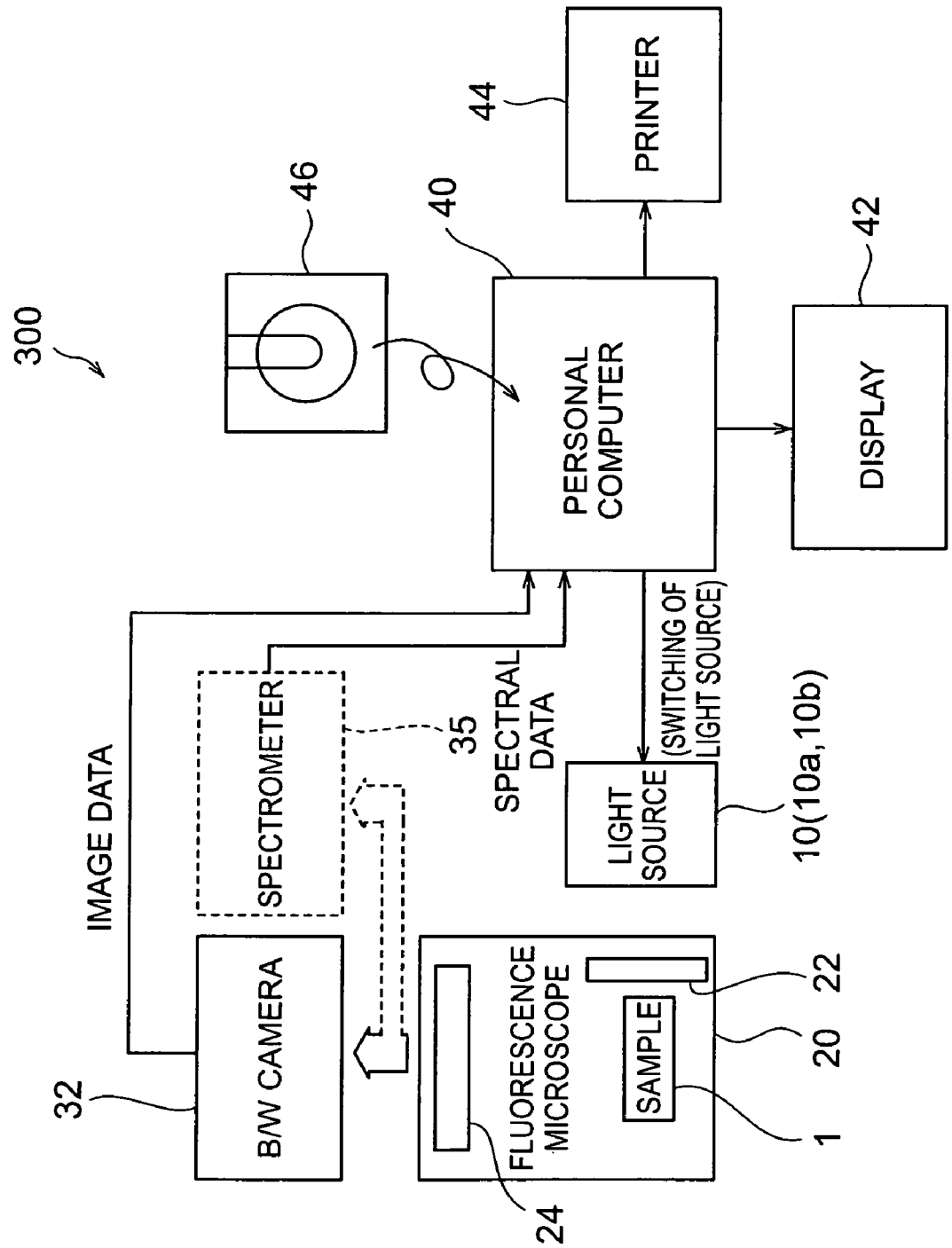
FIG. 7 is a block diagram showing a configuration of another example of a fluorescent dye measurement system.

FIG. 7 is a block diagram showing a configuration of a fluorescent dye measurement system of the present embodiment. This measurement system 300 has the configuration resulting from replacement of the multiband camera 30 in the aforementioned measurement system 100 with a monochrome camera 32. The present embodiment uses a plurality of band-pass filters corresponding to a plurality of fluorescent dyes contained in a target sample, as band-pass filters 24. These band-pass filters have mutually different transmitted wavelength bands. These transmitted wavelength bands are completely separated from each other, without overlap. The band-pass filters 24 can be, for example, interference filters.

The present embodiment is arranged to extract fluorescent components of the respective fluorescent dyes from fluorescence of a target sample by means of the band-pass filters 24 and to detect them with the monochrome camera 32. This results in individually taking fluorescence images of the respective fluorescent dyes. The fluorescence intensities measured with the monochrome camera 32 are used in the same measurement calculation as in the above embodiment, thereby to calculate the concentrations of the respective fluorescence dyes. In the present embodiment the fluorescence from the respective reference samples are also detected through the band-pass filters 24 with the monochrome camera 32 during acquisition of the basic data.

For easier understanding of the measurement calculation, the following will describe the measurement on the assumption that a target sample contains first and second fluorescent dyes and that the concentrations of the fluorescent dyes are measured at a site in the target sample. In this case, just as in the above embodiment, first and second reference samples each of which independently contain one of the first and second fluorescent dyes, respectively, are prepared. The computer 40 executes an operation represented by the formula below to determine the concentrations of the fluorescent dyes at a site in the target sample.

[Formula 20]

$$\begin{bmatrix} c_1 \\ c_2 \end{bmatrix} = J^{-1} \cdot \begin{bmatrix} O_1 \\ O_2 \end{bmatrix}, \quad (22)$$

$$J = \begin{bmatrix} J_{11} & J_{12} \\ J_{21} & J_{22} \end{bmatrix} \quad (23)$$

In the above formula, $O_1$ represents the value of a pixel in a fluorescence image of the target sample taken through the filter 24 for the first fluorescent dye, and $O_2$ the value of the same pixel in a fluorescence image of the target sample taken through the filter 24 for the second fluorescent dye. $J_{11}$ represents the value of the same pixel as those for $O_1$ and $O_2$ in the fluorescence image of the first reference sample taken through the filter 24 for the first fluorescent dye. $J_{12}$ represents the value of the same pixel as those for $O_1$ and $O_2$ in the fluorescence image of the first reference sample taken through the filter 24 for the second fluorescent dye. $J_{21}$ represents the value of the same pixel as those for $O_1$ and $O_2$ in the fluorescence image of the second reference sample taken through the filter 24 for the first fluorescent dye. $J_{22}$ represents the value of the same pixel as those for $O_1$ and $O_2$ in the fluorescence image of the second reference sample taken through the filter 24 for the second fluorescent dye.

The foregoing Eqs (22) and (23) can be generalized as follows.

[Formula 21]

$$\begin{bmatrix} c_1 \\ c_2 \\ \vdots \\ c_m \end{bmatrix} = J^{-1} \cdot \begin{bmatrix} O_1 \\ O_2 \\ \vdots \\ O_m \end{bmatrix}, \quad (24)$$

$$J = \begin{bmatrix} J_{11} & J_{12} & \cdots & J_{1m} \\ J_{21} & J_{22} & \cdots & J_{2m} \\ \vdots & \vdots & & \vdots \\ J_{m1} & J_{m2} & \cdots & J_{mm} \end{bmatrix} \quad (25)$$

It is assumed herein that the target sample contains the first to mth (where m is an integer of 2 or more) fluorescent dyes and that the first to mth band-pass filters are prepared corresponding thereto. $O_j$ (where j is any integer from 1 to m) represents the value of a certain pixel in a fluorescence image of the target sample taken through a filter for the jth fluorescent dye. Component $J_{ij}$ in the ith row and jth column (where i is any integer from 1 to m) in the matrix J represents the value of the same pixel as that for $O_j$ in a fluorescence image of the ith reference sample taken through a filter for the jth fluorescent dye.

In the method of the present embodiment, the fluorescence from the target sample are detected through the band-pass filters. For this reason, where fluorescence spectra of multiple fluorescent dyes largely overlap with each other, the measurement accuracy of the method of the present embodiment is inferior to those in the above embodiments. However, this method has higher measurement accuracy than the conventional technology to handle the fluorescence intensity detected through the band-pass filter, directly as a concentration of a fluorescent dye. This is because the aforementioned calculation formula is not affected by the presence/absence of an overlap between fluorescence spectra. The better measurement accuracy than that of the conventional technology was verified by Inventor's experiment.

Sixth Embodiment

The present embodiment is an application of the present invention to measurement of physiological activity of cell. Namely, the target sample in the present embodiment is a cell. measuring the physiological activity of a cell, functional molecules such as receptors or enzymes in a cell are labeled with a fluorescent dye, and a concentration of the fluorescent dye is measured, thereby measuring an amount or distribution of the functional molecules. For simultaneously measuring multiple types of molecules existing in the same cell, those molecules are labeled with a plurality of fluorescent dyes having different excitation wavelengths and fluorescence wavelengths, and the molecules are discriminated according to their fluorescence colors.

It can be contemplated in this case that the fluorescence from each fluorescent dye is extracted and detected with a band-pass filter to determine the fluorescence intensity. However, where the fluorescence spectra of these dyes largely overlap with each other, it is difficult to discriminate the molecules, because the filter fails to separate the fluorescence emitted from the dyes, from each other.

In contrast to it, the present embodiment is arranged to measure the concentrations of the fluorescent dyes in the cell by use of the measurement system shown in FIG. 1 and in accordance with the procedure shown in FIG. 2. The measurement system 100 of the present embodiment is configured to determine the concentrations of the fluorescent dyes by the calculation using the basic data acquired in advance and the R, G, and B values acquired using the multiband camera 30. The basic data can be acquired by any one of the methods described about the above embodiments. Since there is no need for detecting the fluorescence from the multiple dyes by separating them the discrimination of molecules is easy. Therefore, the measurement system 100 of the present embodiment is useful in measurement of the physiological activity of cell.

The following will describe particulars to be considered where the target sample is a cell.

First, it is sometimes preferable to make a correction for the thickness of the cell. For measuring the concentrations of the fluorescent dyes by the method of the present invention, it is preferable that optical path lengths be equal in the sample during the measurement of fluorescence from the reference samples and the target sample. The reason is that different path lengths provide different fluorescence intensities even in samples of the same concentration. In the case of the target sample being a cell, the thickness of the cell containing the fluorescent dyes, i.e., the optical path length is at most about 10 μm. Where the reference samples are solutions of the fluorescent dyes, it is difficult to accurately prepare the solution samples in the thickness of such order. Even if they can be prepared, there is a distribution of thicknesses according to the shape in one cell, and individual cells have different distributions. In comparison therewith, the optical path lengths are constant over the entire field of view in the solution samples. Therefore, the solution samples cannot be used as reference samples in measurement of a specific cell.

If the microscope used is provided with a confocal optical system, the microscope acquires fluorescence images through a fixed path length and thus the solution samples can be used as reference samples. In the case of tho microscope without the confocal optical system, a potential correction method for the thickness of the cell is as follows. For example, in a case of measuring concentration distributions of fluorescent dyes F1 and F2 contained in a cell, another fluorescent dye F3 to uniformly stain the entire cell (Calcein, CellTracker, or the like) is added to the cell, in addition to these dyes. The cell stained with these three dyes is used as a target sample, dye solutions individually containing these three dyes are used as reference samples, and the measurement is carried out using them to perform the calculation by the method of the present invention, thereby to determine concentration distributions of the respective dyes including the component of thickness of the cell. Since the dye F3 among them is distributed in the uniform concentration over the entire cell, its acquired concentration distribution is proportional to the distribution of thicknesses of the cell. Concentration distributions corrected for the difference in the thickness of the cell can be acquired by using the concentrations at the respective pixels of the dye F3 as coefficients of the thickness of the cell at the respective pixels and dividing the calculated the concentrations of the respective pixels of F1 and F2 by the coefficients.

In this case, it is difficult to accurately determine the optical path lengths of the solution samples as the reference samples, and it is thus impossible to acquire absolute values of the concentrations of the fluorescent dyes. However, this correction is useful in accurately grasping the distributions of the concentrations of the dyes in the cell.

Second, in the case of the reference samples being cells, it is sometimes preferable to make a shading correction. There are fluorescent dyes having a property that a dye alone emits a weak fluorescence but emits a strong fluorescence only when coupled with a specific molecule in a cell. Many dyes for staining nucleic acids e.g., DAPI, are of such a type. Concerning fluorescent proteins such as GFP, it is possible to make a fluorescent dye in a cell by introducing a gene into the cell, but it is difficult to prepare a dye sample outside the cell. For such dyes, solution samples cannot be used as the reference samples. In measurement of a fluorescent dye of this type, the basic data is acquired from a region emitting fluorescence in the cell stained with the fluorescent dye. An image of the cell is acquired, and an average of fluorescence intensities in a region selected from the cell image is used as a fluorescence intensity for a reference concentration. This value is assigned as the fluorescence intensity for the reference concentration to all the pixels.

Illumination of excitation light in the fluorescence microscope is not uniform throughout the entire field of view. For this reason, when fluorescence from a sample in which a dye is uniformly distributed like a solution sample is observed with the fluorescence microscope, strong and weak portions of the fluorescence appear according to intensities of the excitation light in the image. This phenomenon is called shading. The values of the reference concentrations of the respective pixels must be those including information of this shading. When the solution samples are used as the reference samples, data obtained includes the information of shading. Howsoever, in the case where in use of a cell sample the basic data is acquired from a partial region thereof, the information of shading is not available.

In this case, in order to acquire the data of shading, a fluorescence image is acquired from a solution of the fluorescent dye to permit detection of its fluorescence, using the same optical system (filter, dichroic mirror, lens, etc.) as that used in the measurement. Using this as a shading image, the operation is performed pixel by pixel, whereby the information of shading can be given to the image of the reference sample (the image with the same fluorescence intensity given to all the pixels). A conceivable operation method for it is as follows.

$$I_{RC} = I_S \times I_R / I_{S-MAX}$$

$I_{RC}$: luminance of reference sample image with shading information
$I_R$: luminance of original reference sample image
$I_S$: luminance of shading image
$I_{S-MAX}$: maximum luminance of shading image Another conceivable method is to correct the image of the target sample for shading and to directly use the image with the same fluorescence intensity to all the pixels as an image of each reference sample. In this case, a conceivable operation method for correcting the image of the target sample for shading is as follows.

$$I_{TC} = I_T \times I_{S-MAX} / I_S$$

$I_{TC}$: luminance of target sample image corrected for shading
$I_T$: luminance of original target sample image
$I_S$: luminance of shading image
$I_{S-MAX}$: maximum luminance of shading image Concentration distribution images of the fluorescent dyes corrected for influence of shading can be acquired by performing the calculation represented by aforementioned Eq (1) using the reference sample images or the target sample image obtained by the above operation. In this case, since it is difficult to accurately determine the optical path length of the solution sample as each reference sample, it is infeasible to obtain the absolute values of the concentrations of the fluorescent dyes. However, this correction is useful in accurately grasping the distributions of the concentrations of the dyes in the cell.

Seventh Embodiment

The present embodiment is an application of the present invention to measurement of FRET (Fluorescence Resonance Energy Transfer). The FRET is a phenomenon in which an excitation energy given to a certain fluorescent molecule is transferred to another fluorescent molecule. The fluorescent molecule giving the excitation energy is called a donor, and the fluorescent molecule receiving the excitation energy, an acceptor. The donor and acceptor are generated by providing molecules with fluorescent dyes.

With occurrence of the FRET, the fluorescence intensity of the donor decreases, while the fluorescence intensity of the acceptor increases. For this reason, the measurement of the FRET is often carried out as follows. A target sample is illuminated with a light beam of a wavelength to excite the donor, and fluorescence emitted from the target sample is detected. At this time, the fluorescence from the sample is spectroscopically separated into a wavelength region of the fluorescence of the donor and a wavelength region of the fluorescence of the acceptor with a band-pass filter. After this, the fluorescence intensities of the acceptor and donor are separately measured and a ratio of the fluorescence intensities of acceptor/donor is calculated. The FRET can be analyzed using this fluorescence intensity ratio.

In the nature of the phenomenon of the FRET, however, the fluorescence spectra of the donor and acceptor are not so apart from each other, but they often overlap in part. For this reason, the band-pass filter is unable to completely separate the fluorescence from each other, which degrades the accuracy of the FRET measurement.

The present invention can give a solution to this problem in the FRET measurement. The present embodiment is to measure the FRET by use of the measurement system shown in FIG. 1 and in accordance with the procedure shown in FIG. 2. The first step is to prepare a donor reference sample containing only a fluorescent dye for the donor in a predetermined unit concentration and an acceptor reference sample containing only a fluorescent dye for the acceptor in a predetermined unit concentration (step S202). These reference samples are excited, intensities of fluorescence from the respective fluorescent dyes are measured in each of the R, G, and B wavelength bands, and the resultant measured, intensities are stored as basic data (step S204). The fluorescence intensities may be measured using the multiband camera 30 or with the spectrometer 35. After this, the donor in the target sample is excited and a donor fluorescence and an acceptor fluorescence emitted from the target sample are detected using the multiband camera 30 (step S206). In cases where the FRET amount in the target sample varies according to the active state of the target sample with time, e.g., in a case where the target sample is a living cell, this step S206 may be performed continuously multiple times in order to measure the variation. After this, the concentration of the fluorescent dye for the donor and the fluorescent dye for the acceptor are calculated according to the aforementioned Eq (1) (step S208), and an image showing concentration distributions of these dyes is displayed on the display device 42 (steps S210 and S212).

The present embodiment uses a Cameleon solution containing $Ca^{2+}$ (14 μg/ml) as a target sample. Cameleon contains a fluorescent dye CFP as a donor and a fluorescent dye YFP as an acceptor in its molecule. Cameleon also contains sites to bind to $Ca^{2+}$, between these fluorescent dyes. When $Ca^{2+}$ binds to Cameleon, its molecular structure changes to cause significant FRET from CFP to YFP according thereto. As a result, the fluorescence of CFP decreases, while the fluorescence of YFP increases. With increase in the $Ca^{2+}$ concentration, the fluorescence intensity ratio of YFP/CFP also increases according thereto.

The present embodiment is arranged to measure the concentrations of CFP and YFP with stepwise change in the concentration of $Ca^{2+}$ in the target sample, and to multiply the concentrations by fluorescence intensities per unit concentration to calculate the fluorescence intensities of CFP and YFP. Then the fluorescence intensity ratio of YFP/CFP is calculated using these fluorescence intensities.

Figure 8:
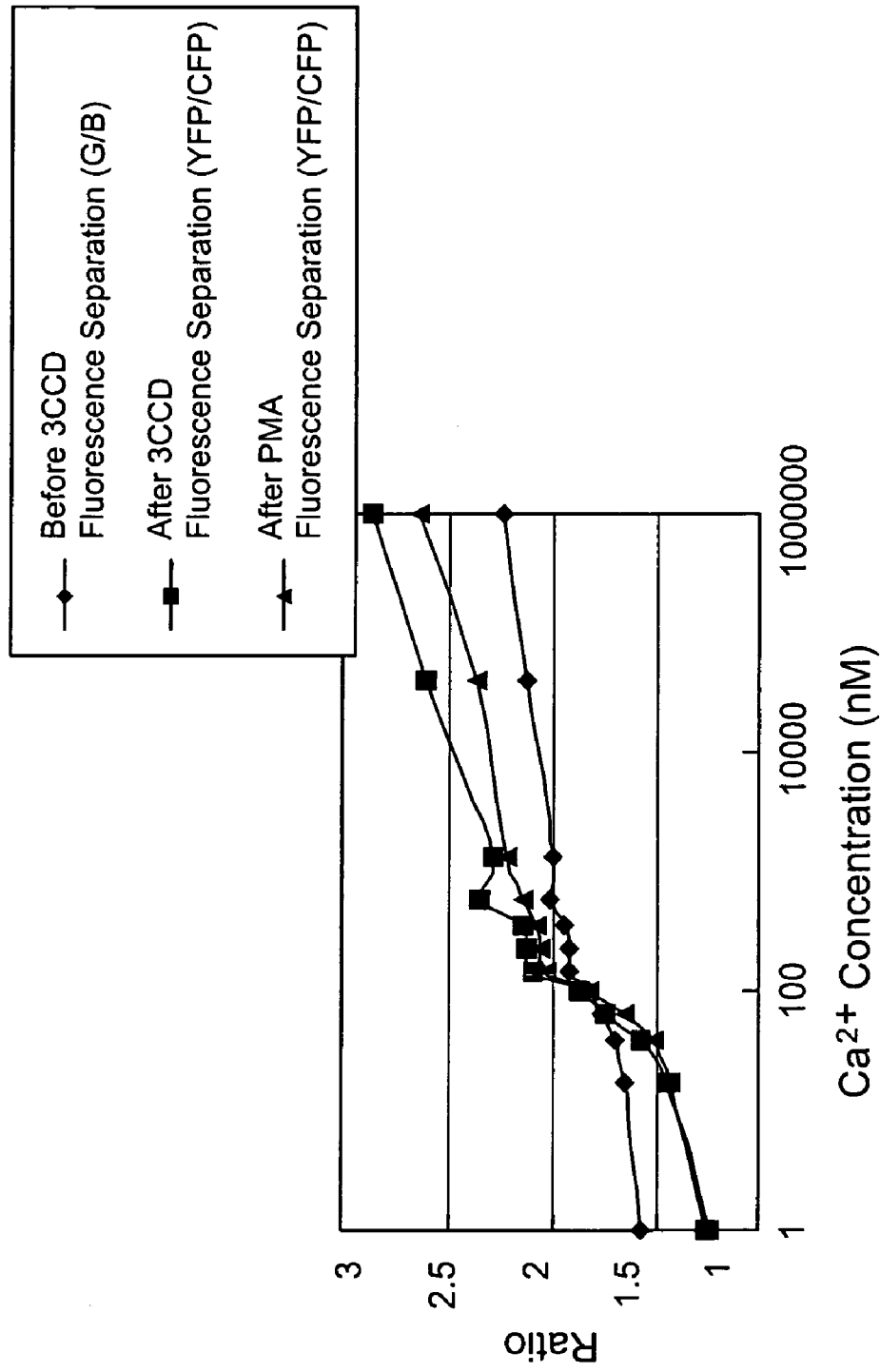
FIG. 8 is a diagram showing a relation between the concentrations of $CA^{2+}$ and fluorescence intensity ratios.

FIG. 8 shows a relation between the concentrations of $Ca^{2+}$ in the target sample and the fluorescence intensity ratios calculated in the present embodiment. For comparison with the present embodiment, FIG. 8 also shows the fluorescence intensity ratios obtained by the conventional method. In this method the fluorescence from the target sample are detected using the multiband camera 30, and the ratio of G/B is calculated on the assumption that the G value of multiband camera 30 is the fluorescence intensity of YFP and that the B value the fluorescence intensity of CFP. In FIG. 8, rhomboids indicate the fluorescence intensity ratios obtained by the conventional method, squares the fluorescence intensity ratios based on the basic data acquired using the multiband camera 30, and triangles the fluorescence intensity ratios based on the basic data acquired with the spectrometer 35.

As shown in FIG. 8, the fluorescence intensity ratios acquired by the method of the present embodiment vary more significantly than the fluorescence intensity ratios acquired by the conventional method, according to the change in the $Ca^{2+}$ concentration. This is advantageous in detecting a fine change in the $Ca^{2+}$ concentration. The fluorescence of CFP is also detected in the G wavelength band of the camera 30 to measure the fluorescence of YFP in the conventional method. In the G wavelength band, therefore, the FRET increases the fluorescence intensity of YFP while decreases the fluorescence of CFP. It is considered that this curbs the increase of the G value of camera 30 and thus curbs the change in the fluorescence intensity ratio according thereto. In contrast to it, since the method of the present embodiment is arranged to calculate the fluorescence intensities, using the calculation formula not affected by mixture of the fluorescence, the fluorescence intensity ratio varies with higher sensitivity according to the change in the $Ca^{2+}$ concentration.

In the present embodiment, the measurement results are displayed by the expression method shown in FIG. 5. In this method the concentration information of the fluorescent dyes is displayed using the pseudocolors. Specifically, the concentration distributions of the first and second fluorescent dyes are displayed as images 81 and 82. In these images 81 and 82, the concentrations of the fluorescent dyes are indicated by luminances. Since in the FRET analysis the amount of FRET is generally evaluated by the intensity ratio of these two fluorescent dyes, i.e., the concentration ratio, a distribution of fluorescence intensity ratios calculated is indicated by pseudocolors in image 83. Furthermore, the fluorescence intensity ratios can be associated with $Ca^{2+}$ concentrations as in the graph of FIG. 8, whereby the values of the fluorescence intensity ratios can also be converted into the values of $Ca^{2+}$ concentrations. In image 84 a distribution of $Ca^{2+}$ concentrations is indicated using pseudocolors. A color bar 85 is also displayed in these images 81-84.

The following will describe the advantage of the present embodiment in comparison with the conventional technology. A known method of determining the fluorescence intensity ratio mainly by operation as in the present embodiment is the one disclosed in the article by Gerald W. Gordon et al. "Quantitative Fluorescence Resonance Energy Transfer Measurements Using Fluorescence Microscopy" (Biophysical Journal, vol 74, pp 2702-2713, May 1998). In this method, three types of samples are prepared as in the present embodiment. This method uses three types of band-pass filters, i.e., a filter for exciting the donor and measuring the fluorescence of the donor, a filter for exciting the acceptor and measuring the fluorescence of the acceptor, and a filter for exciting the donor and measuring the fluorescence of the acceptor. This method is to acquire nine measurements by combination of these samples with the filters and to determine the value of FRET by mathematical operation.

However, the method of the present embodiment is much simpler than the method of Gordon et al. The reason is that the method of Gordon et al. involves nine fluorescence measurements, whereas the method of the present embodiment requires only three fluorescence measurements. When the measurement method of the present invention is applied to the FRET as described above, the fluorescence intensity ratio of acceptor/donor can be readily and quickly acquired.

FIRST EXAMPLE

The present invention will be further described below with some examples. The Inventor conducted the measurement of fluorescent dyes by use of the measurement system 100 shown in FIG. 1 and in accordance with the method of the first embodiment. The multiband camera 30 used was the 3-CCD color camera ORCA-3CCD C7780 available from Hamamatsu Photonics K.K. FIG. 9 shows spectral sensitivity characteristics of the camera 30. As described previously, the camera 30 has the two types of sensitivity modes, the Low Light mode and the High Light mode. In FIG. 9 solid lines indicate the sensitivity characteristics in the Low Light mode, and dashed lines the sensitivity characteristics in the High Light mode. In the present example the R, G, and B values in the Low Light mode were used in the measurement calculation.

The fluorescent dyes used were three types, Alexa Fluor 350, Fura2, and Cascade Yellow. The Inventor mixed two of them in appropriate concentrations to prepare three types of solutions as target samples. These three types of dye solutions all have their absorption wavelengths in the same wavelength band (350-440 nm). When these dye solutions are illuminated with light in this wavelength band to excite the dyes, these solutions emit fluorescence having mutually different spectra. The band-pass filter 22 has a transmitted wavelength band equal to this wavelength band and extracts components in this wavelength band from the white light of Xe lamp 10a to generate excitation light.

A specific measurement procedure will be described below. First, reference samples were prepared. A unit concentration of each fluorescent dye was determined so as to obtain an appropriate fluorescence intensity according to the sensitivity of camera 30, and a solution independently containing each fluorescent dye in the unit concentration was prepared. Three types of solutions were obtained as reference samples in this manner.

Next, the basic data was acquired using these reference samples. Specifically, each reference sample was excited and a fluorescence image generated from each reference sample was taken with the camera 30. This image acquisition was conducted under the conditions of exposure of 30 msec and Gain=Low. The image data acquired in the R, G, and B wavelength bands of the camera 30 was stored in the storage device of the computer 40. The pixel values of the image data are the basic used in the measurement calculation.

Then two types of reference samples were mixed at an appropriate ratio to prepare a target sample, and the target sample is illuminated with the excitation light. A fluorescence image of the target sample was taken with the camera 30 to acquire image data. Pixel values of this image data are target data. The computer 40 executed the operation represented by the aforementioned Eq (1) pixel by pixel, using the basic data and target data, to calculate concentration distributions of the two fluorescent dyes in the target sample.

SECOND EXAMPLE

The Inventor also conducted acquisition of the basic data and target data with the use of the spectrometer 35, instead of the camera 30. The spectrometer 35 used was PMA-11 (c7473, BTCCD 200-950 nm) available from Hamamatsu Photonics K.K. The measurement of fluorescence from reference samples with the spectrometer 35 was conducted in the light source mode and under the conditions of s/n=18, Gain=Middle, and wavelength interval=1 nm. The computer 40 performed a smoothing process of 5 points (5 nm) on the spectral data acquired with the spectrometer 35.

Figure 10:
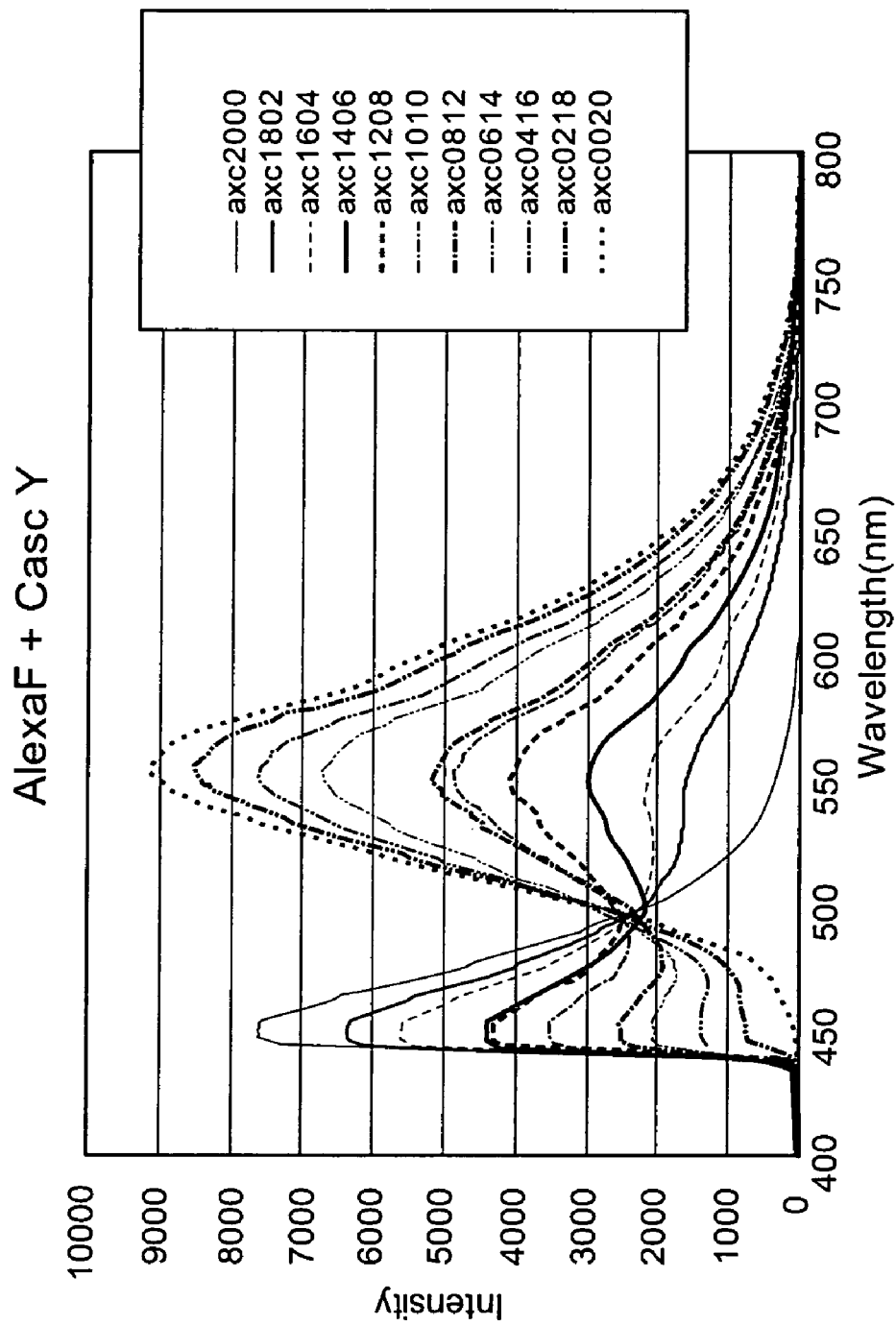
FIG. 10 is a diagram showing spectral data acquired from target samples in which Alexa Fluor and Cascade Yellow are mixed.
Figure 11:
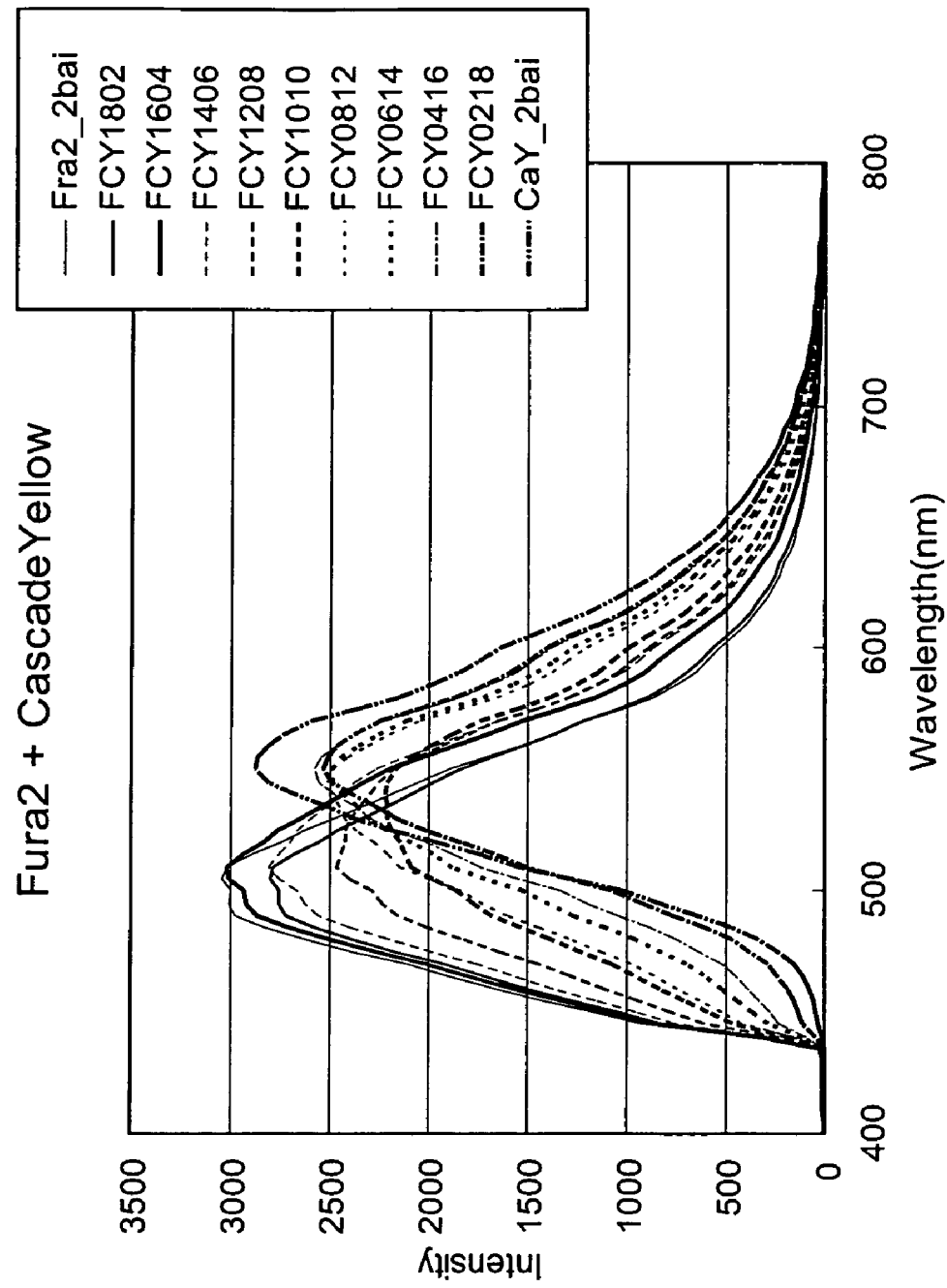
FIG. 11 is a diagram showing spectral data acquired from target samples in which Fura2 and Cascade Yellow are mixed.

For reference, the spectral data acquired from target samples is presented in FIGS. 10 and 11. FIG. 10 shows the spectral data acquired from target samples in which the fluorescent dyes Alexa Fluor and Cascade Yellow are mixed at various ratios. The spacing between peak wavelengths of fluorescence emitted from these dyes is relatively wide, about 110 nm. FIG. 11 shows the spectral data required from target samples in which the fluorescent dyes Fura2 and Cascade Yellow are mixed at various ratios. The spacing between peak wavelengths of fluorescence emitted from these dyes is relatively narrow, about 30 nm. As described above, the spectral data was the data obtained after the smoothing process.

The computer 40 executed the operations represented by the aforementioned Eqs (9), (10), and (1), using the spectral data acquired from the reference samples and target samples, to calculate the concentrations of the dyes. The spectral data in all the spectral wavelength bands acquired from the reference samples were multiplied by the sensitivity characteristics shown in FIG. 9, the products were summed up, and the sum was multiplied by the coefficient a for correction indicated in Eq (10), thereby calculating the basic data J. Similarly, the spectral data in all the spectral wavelength bands acquired from each target sample were multiplied by the sensitivity characteristics shown in FIG. 9, the products were summed up, and the sum was multiplied by the coefficient a for correction, thereby calculating target data $R_{tgt}$, $G_{tgt}$, and $B_{tgt}$. This operation was conducted using the smoothed spectral data with the width of 5 nm in the range of 300-780 nm. The spectrometer 35 can measure only a site in each sample at a time. Numerical values calculated by the computer 40 indicate dye concentrations at the measurement site.

THIRD EXAMPLE

The Inventor also conducted measurement of the concentrations of fluorescent dyes according to the method of the fifth embodiment. In this example, intensities of fluorescence emitted from reference samples and target samples were measured through the band-pass filter. Three band-pass filters were used according to the fluorescence spectra of three types of fluorescent dyes. The first band-pass filter had the center wavelength of 440 nm and the bandwidth of 21 nm. The second band-pass filter had the center wavelength of 510 nm and the bandwidth of 23 nm; The third band-pass filter had the center wavelength of 546 nm and the bandwidth of 10 nm.

Fluorescence through each band-pass filter was detected with a monochrome (B/W) camera. The monochrome camera used was the digital B/W camera ORCA-II available from Hamamatsu Photonics K.K. The acquisition of fluorescence images was conducted under the conditions of exposure of 30 msec, Gain=Low, and binning 4*4.

The computer 40 performed the operation represented by the aforementioned Eqs (22) and (23) using the pixel values of the fluorescence images taken with the monochrome camera. This resulted in calculating the concentrations of two fluorescent dyes in a target sample.

For reference, fluorescence intensities were also measured with the same spectrometer as that used in the second example. Specifically, fluorescence intensities were measured at intervals of 1 nm with the spectrometer and the fluorescence intensities in all the spectral wavelength bands were summed up to calculate the fluorescence intensities.

Figure 12:
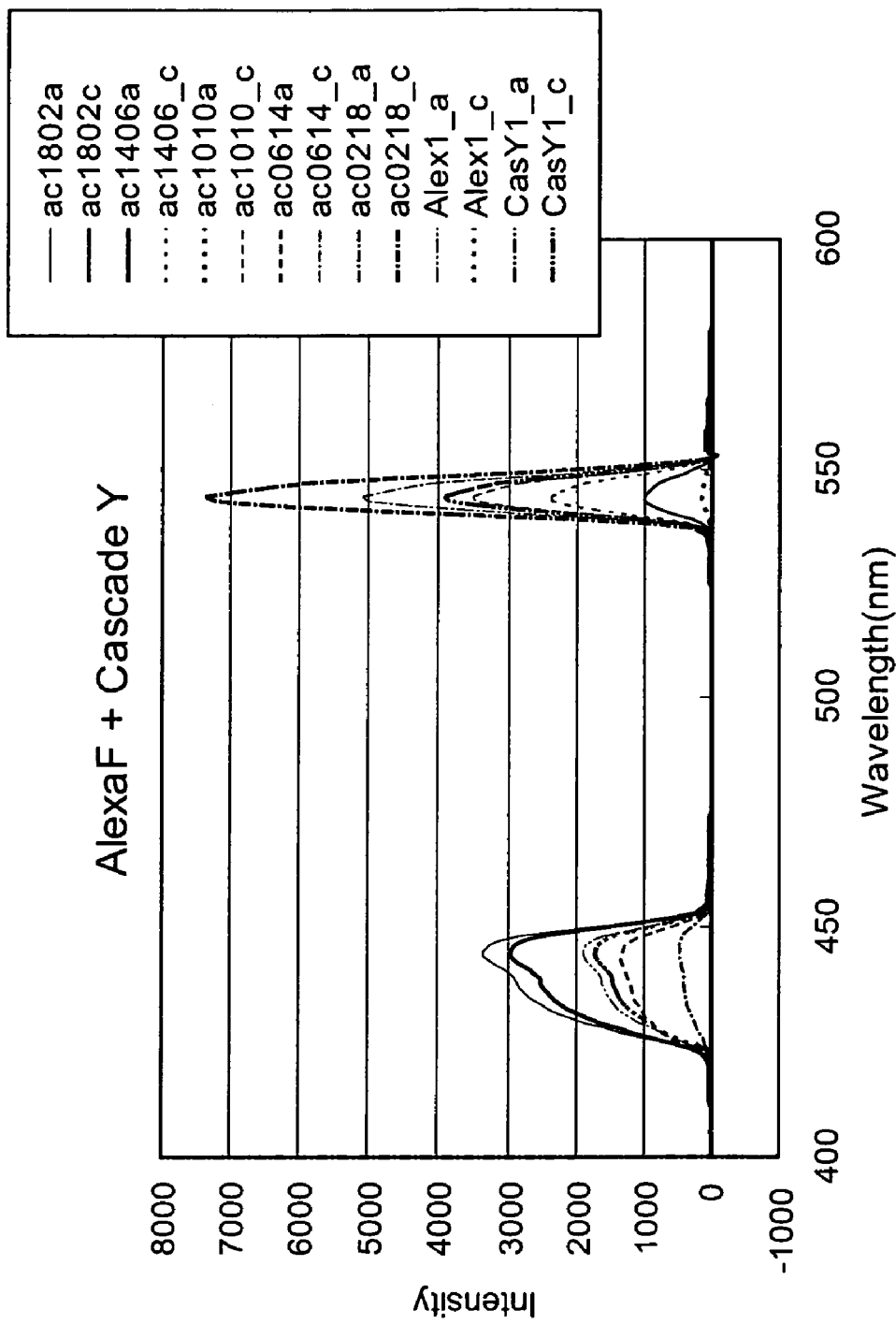
FIG. 12 is a diagram showing spectral data measured through a band-pass filter from target samples in which Alexa Fluor and Cascade Yellow are mixed.
Figure 13:
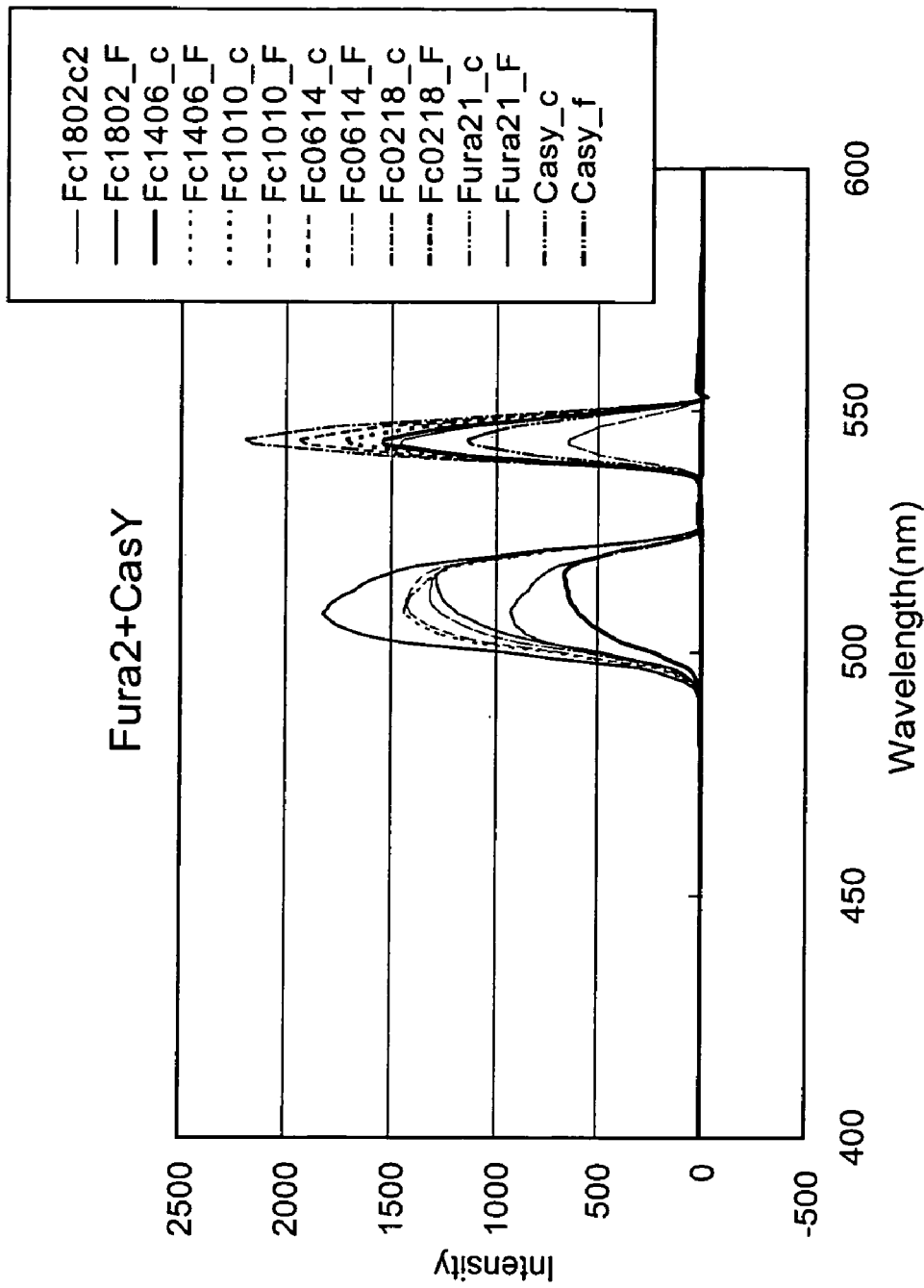
FIG. 13 is a diagram showing spectral data acquired through a band-pass filter from target samples in which Fura2 and Cascade Yellow are mixed.

FIG. 12 shows the spectral data measured through the band-pass filters from target samples in which the fluorescent dyes Alexa Fluor and Cascade Yellow are mixed at various ratios. FIG. 13 shows the spectral data measured through the band-pass filters from target samples in which the fluorescent dyes Fura2 and Cascade Yellow and mixed at various ratios.

COMPARATIVE EXAMPLE

The Inventor also performed the measurement for comparison with the above examples in such a manner that fluorescence of each dye was extracted from fluorescence emitted from a target sample, using the band-pass filters, and the fluorescence was taken with the monochrome camera. The band-pass filters used were the same as in the third example. The monochrome camera used was the digital B/W camera ORCA-II available from Hamamatsu Photonics K.K. The acquisition of fluorescence images was conducted under the conditions of exposure of 30 msec, Gain=Low, and binning 4*4.

In this example, concentrations $c_1$ and $c_2$ of two fluorescent dyes in a target sample were calculated according to the following equations (conventional equations).

$$c_1 = \text{Sample } S1/\text{kijyun } S1 \qquad (26.1)$$

$$c_2 = \text{Sample } S2/\text{kijyun } S2 \qquad (26.2) \text{ [Formula 22]}$$

In these equations, Sample S1 and Sample S2 represent intensities of fluorescence extracted from fluorescence of the target sample with the band-pass filters, and Kijyun S1 and Kijyun S2 intensities of fluorescence emitted from reference samples. As apparent from these equations, the intensities of the fluorescence measured through the band-pass filters are handled as the concentrations of the respective fluorescent dyes in the present example.

Concentration Calculation Results

Figure 14:
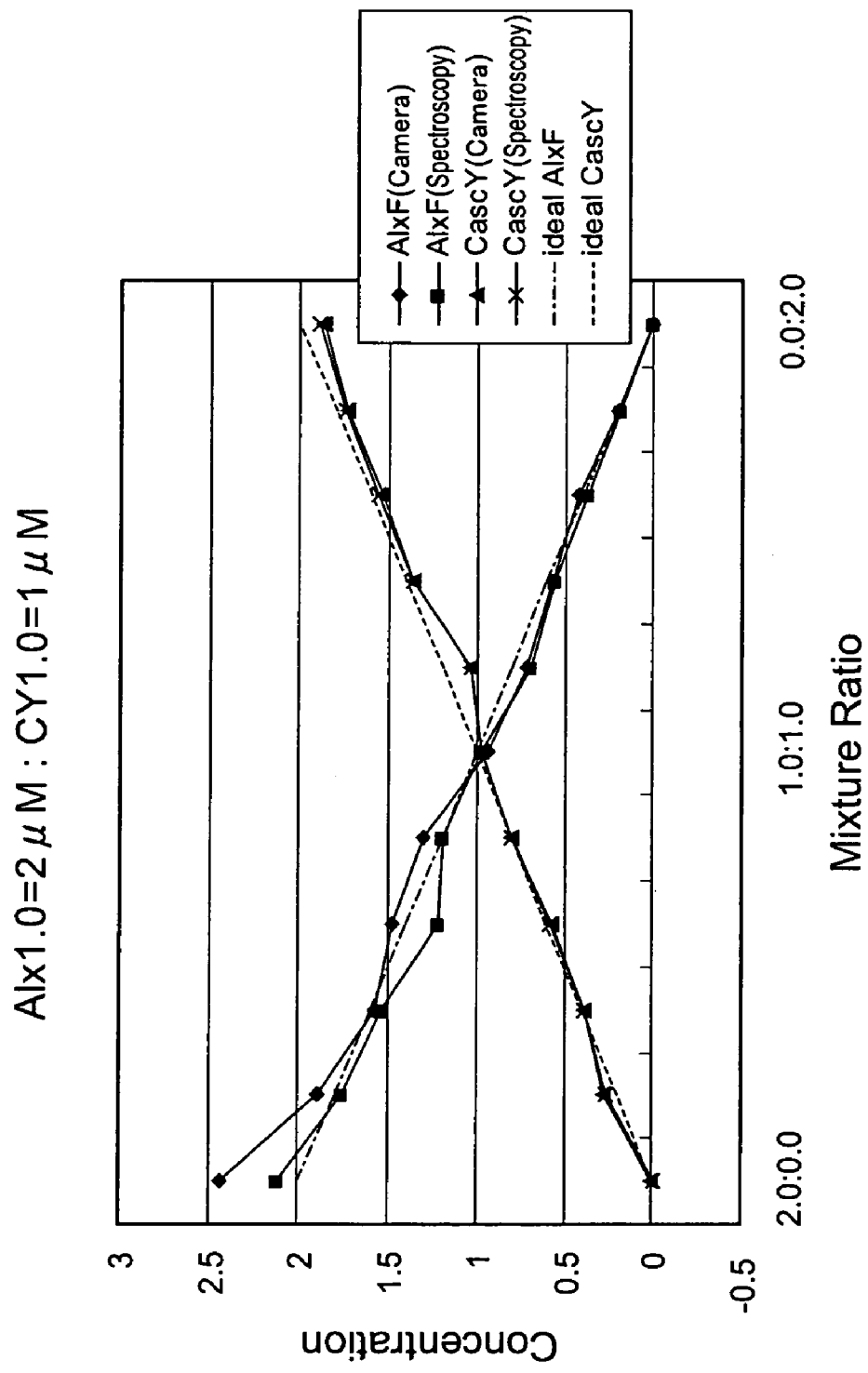
FIG. 14 is a diagram showing the concentrations of Alexa Fluor and Cascade Yellow calculated in first and second examples.
Figure 15:
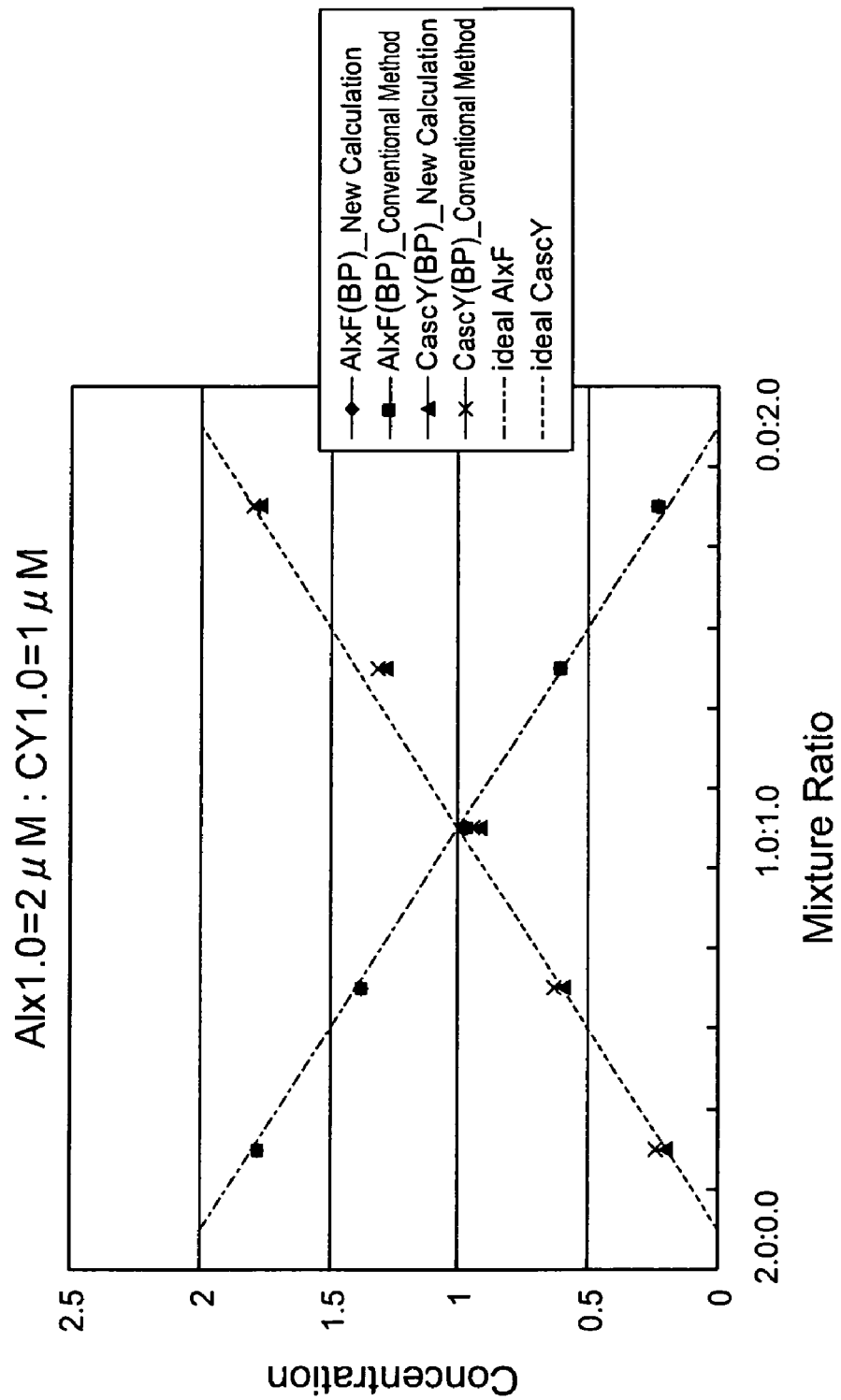
FIG. 15 is a diagram showing the concentrations of Alexa Fluor and Cascade Yellow calculated in a third example and a comparative example.

First the measurement results of Alexa Fluor and Cascade Yellow with a small overlap between their fluorescence spectra will be described with reference to FIGS. 14 and 15. FIG. 14 shows the concentrations of Alexa Fluor and Cascade Yellow calculated in the first and second examples. FIG. 15 shows the concentrations of Alexa Fluor and Cascade Yellow calculated in the third example and in the comparative example. In these figures, the horizontal axis indicates the mixture ratios of dyes, and the vertical axis the concentrations of the dyes. The concentrations are indicated with the unit concentration of each dye being 1. The unit concentration of Alexa Fluor is 2 μM (where micromole) and the unit concentration of Cascade Yellow 1 μM.

In FIG. 14 rhomboids indicate the concentrations of Alexa Fluor calculated in the first example, squares the concentrations of Alexa Fluor calculated in the second example, triangles the concentrations of Cascade Yellow calculated in the first example, and × the concentrations of Cascade Yellow calculated in the second example. In FIG. 15 rhomboids indicate the concentrations of Alexa Fluor calculated in the third example, squares the concentrations of Alexa Fluor calculated in the comparative example, triangles the concentrations of Cascade Yellow calculated in the third example, and × the concentrations of Cascade Yellow calculated in the comparative example. In these figures, a chain line indicates actual concentrations of Alexa Fluor in the target sample, and a dashed line actual concentrations of Cascade Yellow in the target sample.

It is seen from the comparison between FIG. 14 and FIG. 15 that there is little difference in the measurement accuracy of Alexa Fluor and Cascade Yellow with the spacing between their center wavelengths being relatively wide, between the examples and the comparative example. This is because the overlap is small between the fluorescence spectra of these dyes.

Figure 16:
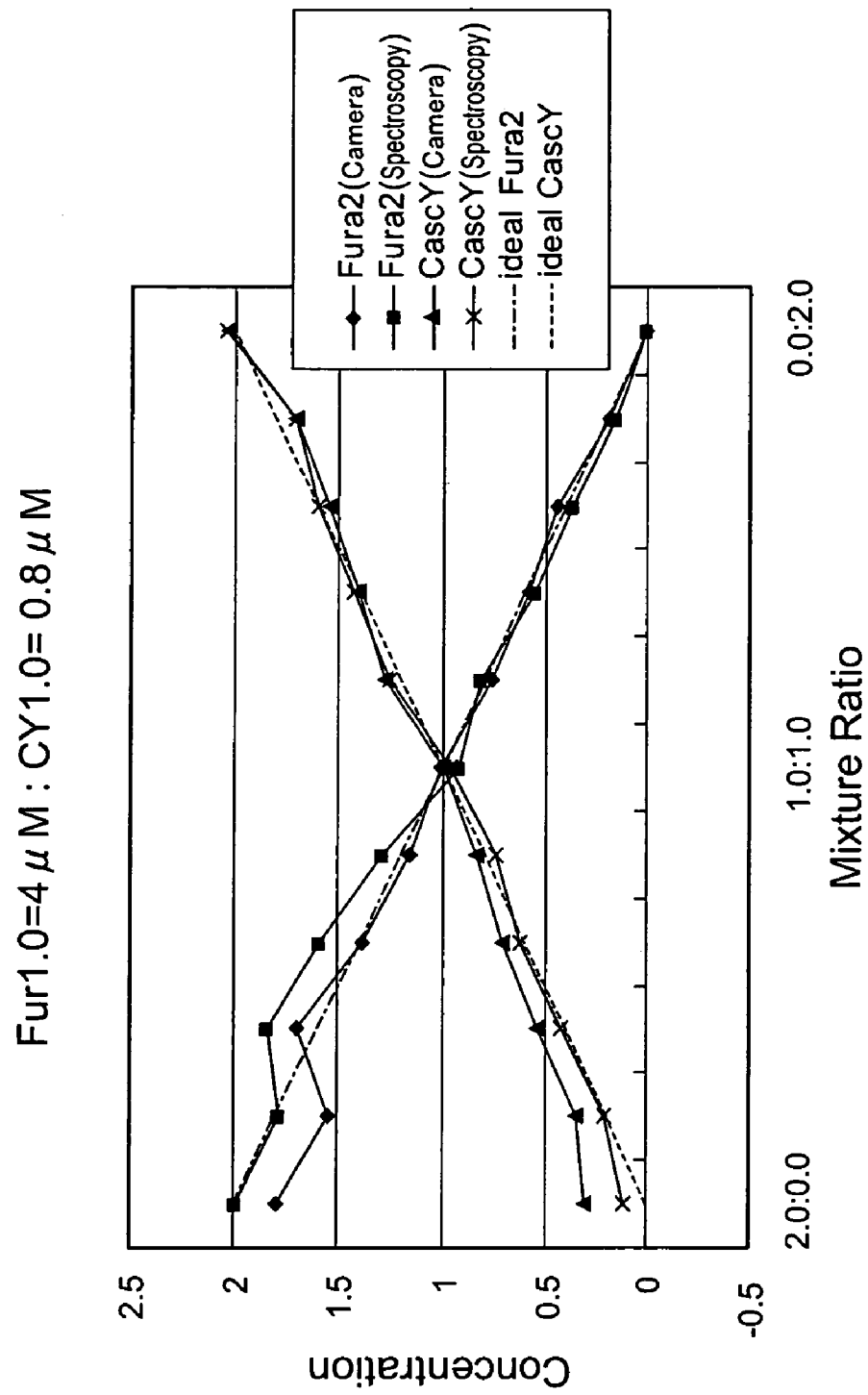
FIG. 16 is a diagram showing the concentrations of Fura2 and Cascade Yellow calculated in the first and second examples.
Figure 17:
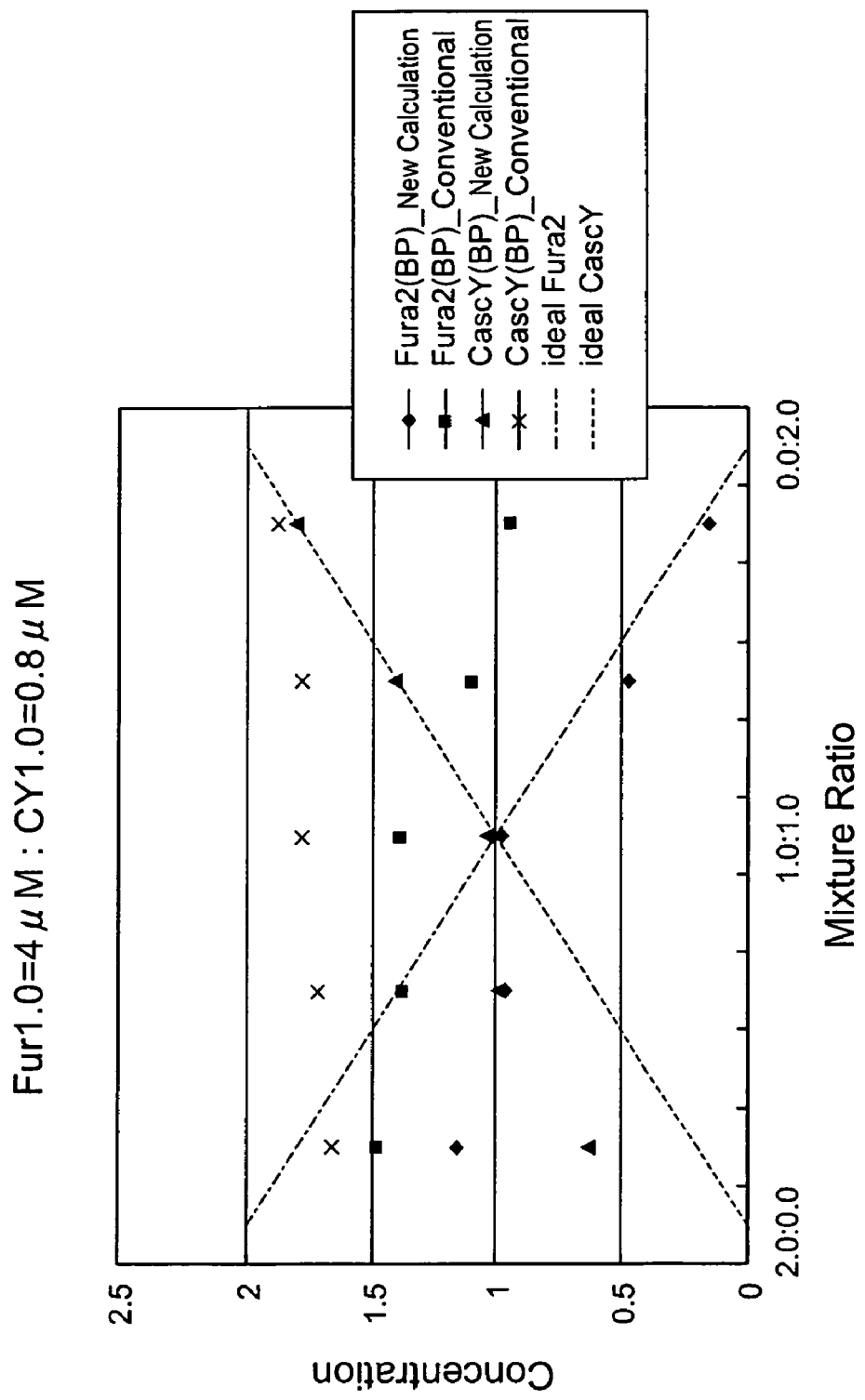
FIG. 17 is a diagram showing the concentrations of Fura2 and Cascade Yellow calculated in the third example and the comparative example.

Next, the measurement results with Fura2 and Cascade Yellow with the overlap between their fluorescence spectra being large will be described with reference to FIGS. 16 and 17. FIG. 16 shows the concentrations of Fura2 and Cascade Yellow calculated in the first and second examples. FIG. 17 shows the concentrations of Fura2 and Cascade Yellow calculated in the third example and in the comparative example. In these figures, the horizontal axis indicates the mixture ratios of the dyes, and the vertical axis the concentrations of the dyes. The concentrations are indicated with the unit concentration of each dye being 1. The unit concentration of Fura2 is 4 μM, and the unit concentration of Cascade Yellow 0.8 μM.

In FIG. 16 rhomboids indicate the concentrations of Fura2 calculated in the first example, squares the concentrations of Fura2 calculated in the second example, triangles the concentrations of Cascade Yellow calculated in the first example, and × the concentrations of Cascade Yellow calculated in the second example. In FIG. 17 rhomboids indicate the concentrations of Fura2 calculated in the third example, squares the concentrations of Fura2 calculated in the comparative example, triangles the concentrations of Cascade Yellow calculated in the third example, and × the concentrations of Cascade Yellow calculated in the comparative example. In these figures, a chain line indicates actual concentrations of Fura2 in the target sample, and a dashed line actual concentrations of Cascade Yellow in the target sample.

It is seen from the comparison between FIG. 16 and FIG. 17 that the difference is large in the measurement accuracy of Fura2 and Cascade Yellow to emit fluorescence with the spacing between their center wavelengths being relatively narrow, between the examples and the comparative example. This is because the overlap is large between the fluorescence spectra of these dyes. Since the method of the comparative example is arranged to detect each fluorescence in a state in which the fluorescence of one dye is mixed in the fluorescence of the other dye, the accuracy of the measurement is significantly lowered. In contrast to it, the methods of the examples are able to measure the concentrations of the dyes with high accuracy, without being affected by the overlap between the fluorescence spectra.

In the third example, as in the comparative example, the fluorescence from the sample are detected through the band-pass filter. It is seen from FIG. 17 that the measurement accuracy even in this case is superior to that in the comparative example. This arises from the difference between the calculation equations (22) and (23) used in the third example and the equations (26.1) and (26.2) used in the comparative example. As seen from the comparison between FIG. 16 and FIG. 17, however, the measurement accuracy in the first and second examples to detect the fluorescence without intervention of the band-pass filter is much superior to that in the third example. A conceivable reason for it is that in the first and second examples the adjacent detection wavelength bands overlap and cover the entire wavelength band for evaluation, whereas in the third example the adjacent detection wavelength bands do not overlap, and data of only a partial wavelength band like a spot is handled, so as to fail to cover the entire evaluated wavelength band of the target sample, possibly with some lack of data.

As apparent from FIGS. 14 and 16, the fluorescence intensities can be measured with the camera, while achieving the measurement accuracy comparable to that in the case where the fluorescence intensities are measured with the spectrometer and where the calculation is conducted using the spectral data. As apparent from this, the technique in the first example, i.e., the measurement using the multiband camera is to determine the fluorescence intensity by multiplying spectral data in a wavelength region with a certain width to be measured, by a characteristic equivalent to a sensitivity function of the camera. Therefore, the measurement with the camera fundamentally acquires the information equivalent to that where data is taken over the entire wavelength range as in the measurement with the spectrometer. For this reason, the measurement can be performed with the camera, with the accuracy equivalent to that in spectroscopy.

The experiment results showed the difference between the measurement results with the camera and the measurement results with the spectrometer. However, the Inventor and others clarified that the major factor for this difference was decrease in fluorescence intensity according to damage of the dyes due to light. Namely, the spectroscopic measurement took a too long measurement time and caused a too large reduction in light quantity of the dyes. After this was found, the time for spectral measurement was shortened, and this resulted in approximate agreement between the measurement results with the camera and the measurement results with the spectrometer.

Figure 18:
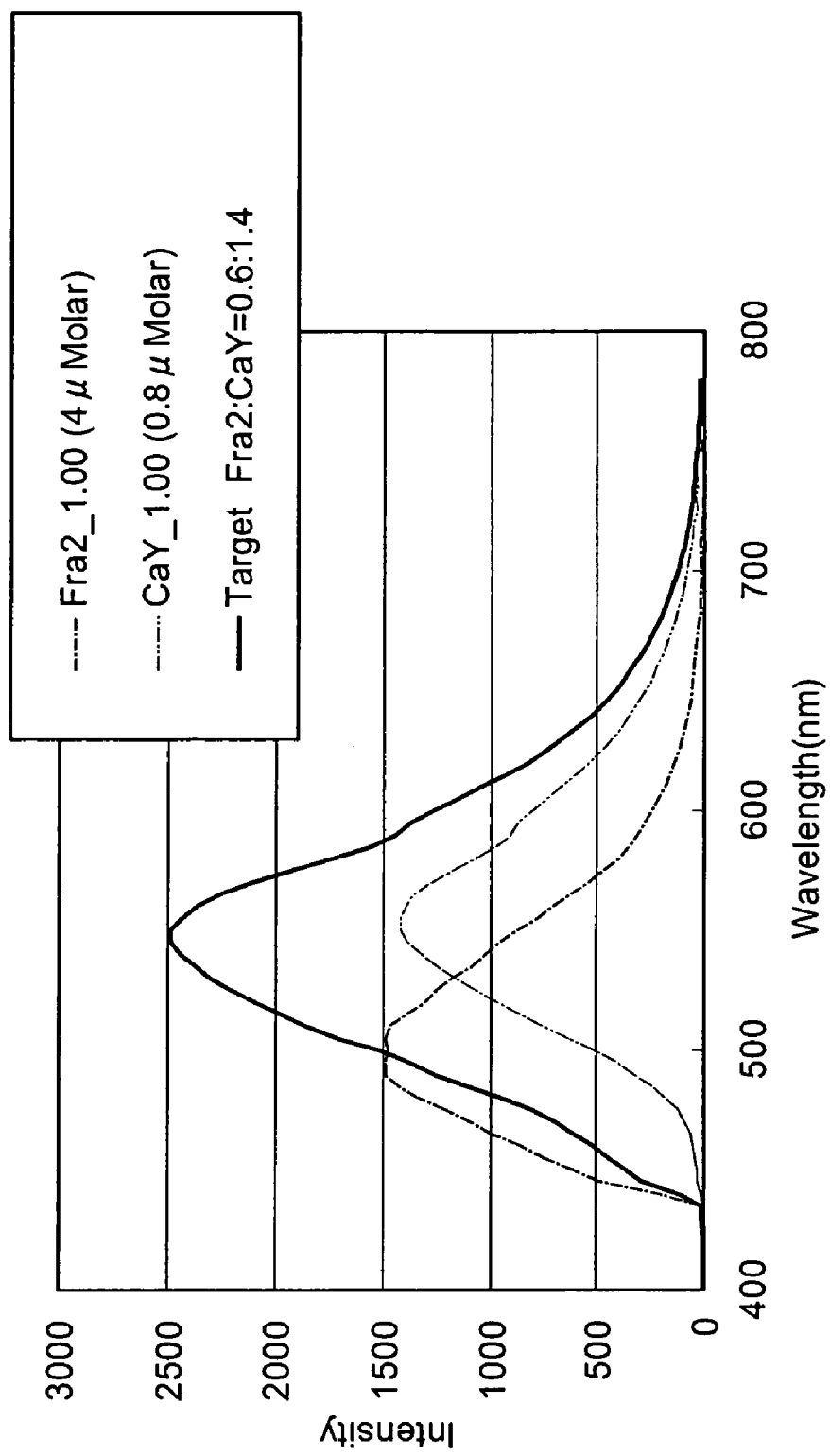
FIG. 18 is a diagram showing actually measured fluorescence spectra of reference samples and a target sample.

The accuracy of the measurement by the first and second examples will be confirmed below with reference to FIGS. 18 to 20. FIG. 18 shows fluorescence spectra of a reference sample containing Fura2, a reference sample containing Cascade Yellow, and a target sample containing Fura2 and Cascade Yellow. The unit concentration of Fura2 is 4 μM, and the unit concentration of Cascade Yellow 0.8 μM. In the target sample, Fura2 and Cascade Yellow are mixed at the ratio of 0.6:1.4. The result of actual measurement of the target sample with the spectrometer is shown as a target spectrum in FIG. 18.

The result of the measurement calculation in the camera method in the first example was Fura2:CaY=0.571:1.4005, and the result of the measurement calculation in the spectrometer method in the second example Fura2:CaY=0.528: 1.434. Spectral intensities can be simulated by multiplying the calculated concentrations by the fluorescence spectra of the corresponding reference samples (hereinafter referred to as "reference spectra") and summing up the products. FIG. 19 and FIG. 20 show simulation spectra calculated in this manner.

In the spectrometer method the reference spectra and the target spectrum are actually measured. For this reason, the accuracy of the calculation itself can be confirmed by performing the simulation calculation using the reference spectra and comparing the resultant fluorescence spectrum with the target spectrum. On the other hand, when the camera system is strictly considered, the reference spectra and target spectrum acquired in the camera method are delicately different from those acquired in the spectrometer method. For this reason, it stands to reason that there is the difference between the fluorescence spectrum acquired by the simulation calculation in the camera method and the fluorescence spectrum acquired by the simulation calculation in the spectrometer method. Therefore, it is not always the case that amounts of deviation between the target spectrum actually measured and the fluorescence spectra acquired by the simulation results directly reflect the accuracies of the camera method and the spectrometer method. However, approximate accuracies can be checked and thus this technique was adopted.

Figure 19:
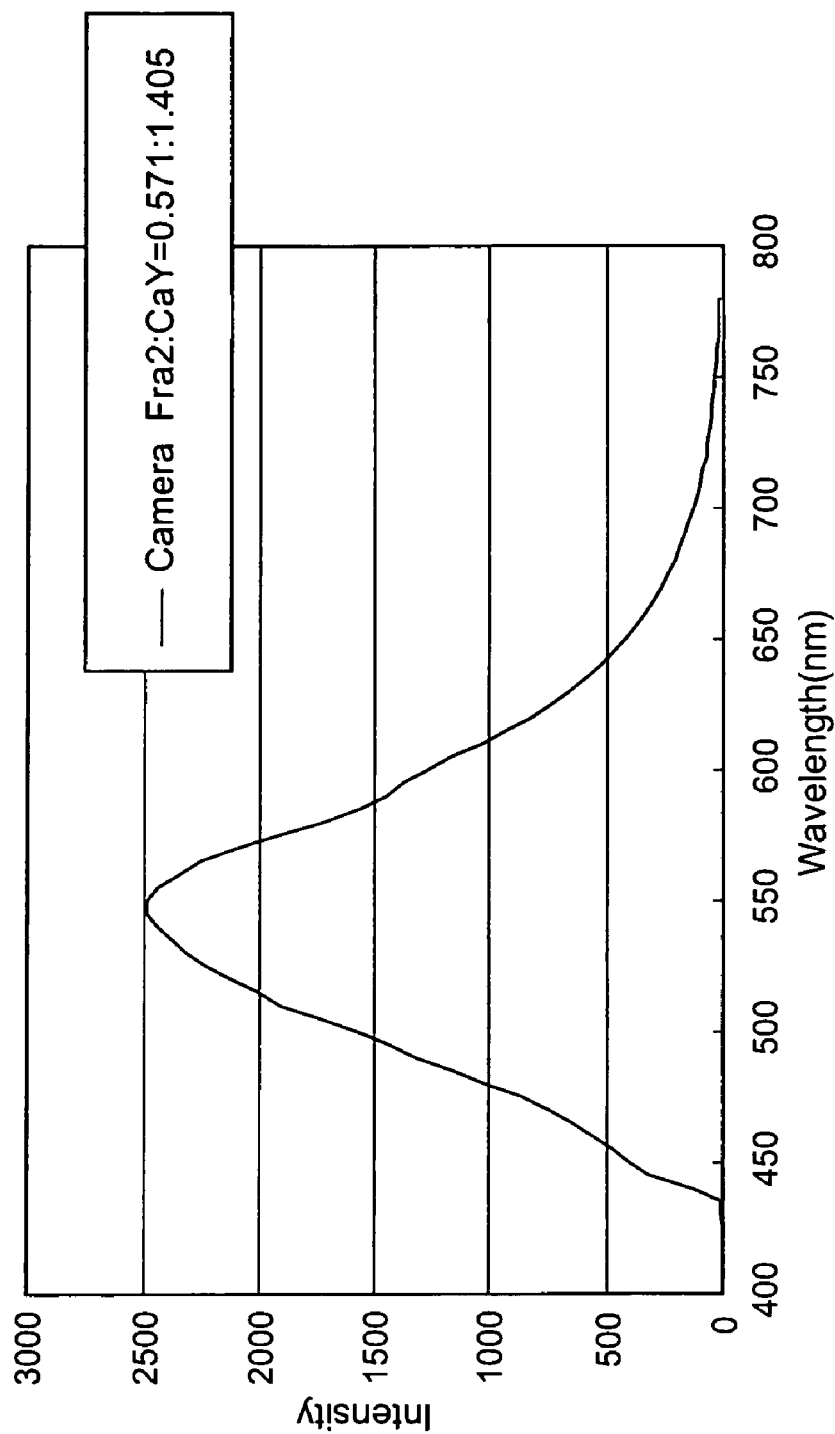
FIG. 19 is a diagram showing a fluorescence spectrum of a target sample calculated using the concentrations of fluorescent dyes obtained in the first example.
Figure 20:
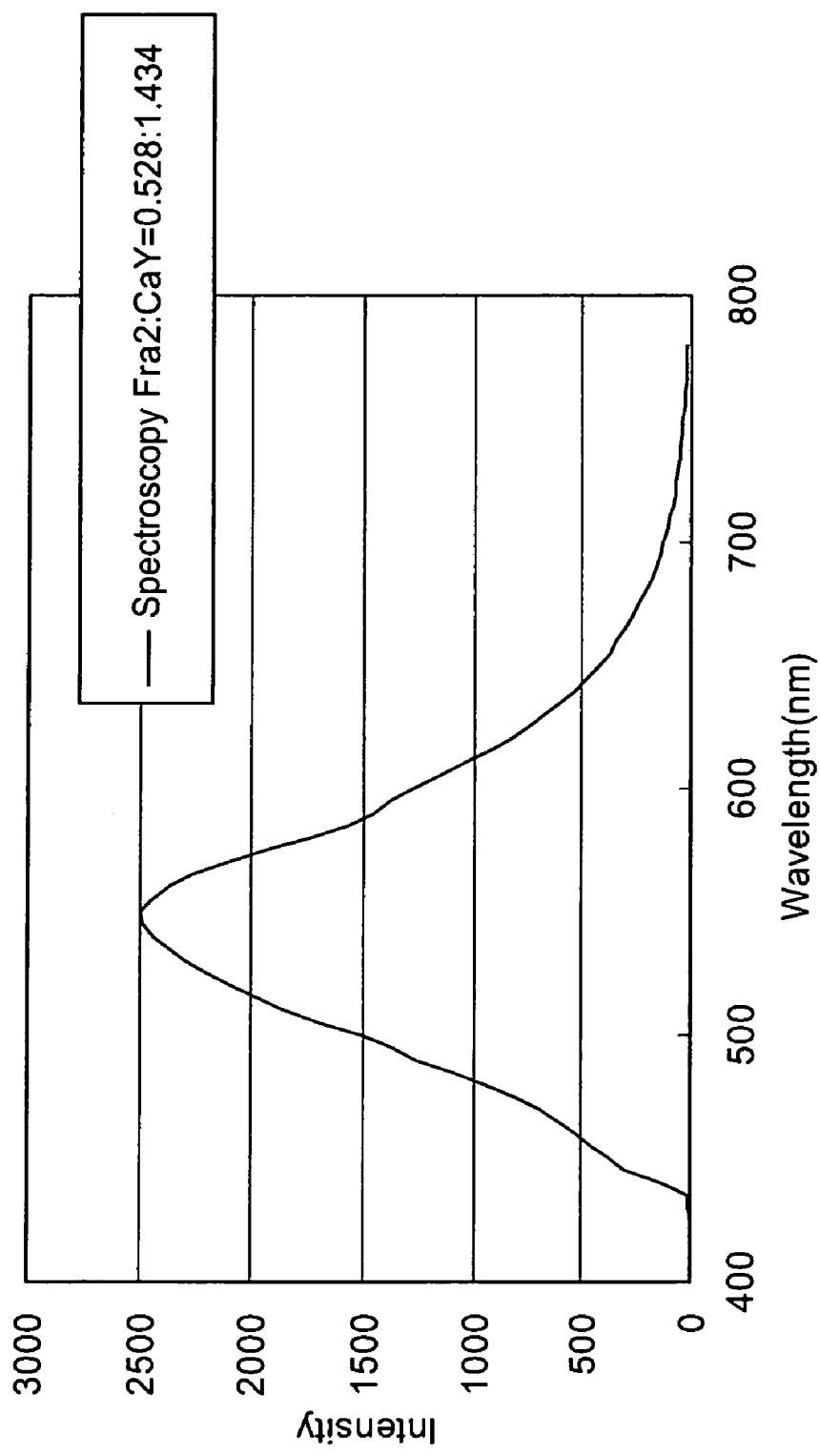
FIG. 20 is a diagram showing a fluorescence spectrum of a target sample calculated using the concentrations of fluorescent dyes obtained in the second example.

It is apparent from the comparison between FIG. 18 and FIGS. 19 and 20 that the fluorescence spectra calculated using the measurement results of the first and second examples are extremely close in shape to the actual fluorescence spectrum. It is therefore understood that the concentrations of the fluorescent dyes can be measured with excellent accuracy by the first and second examples.

Eighth Embodiment

Figure 21:
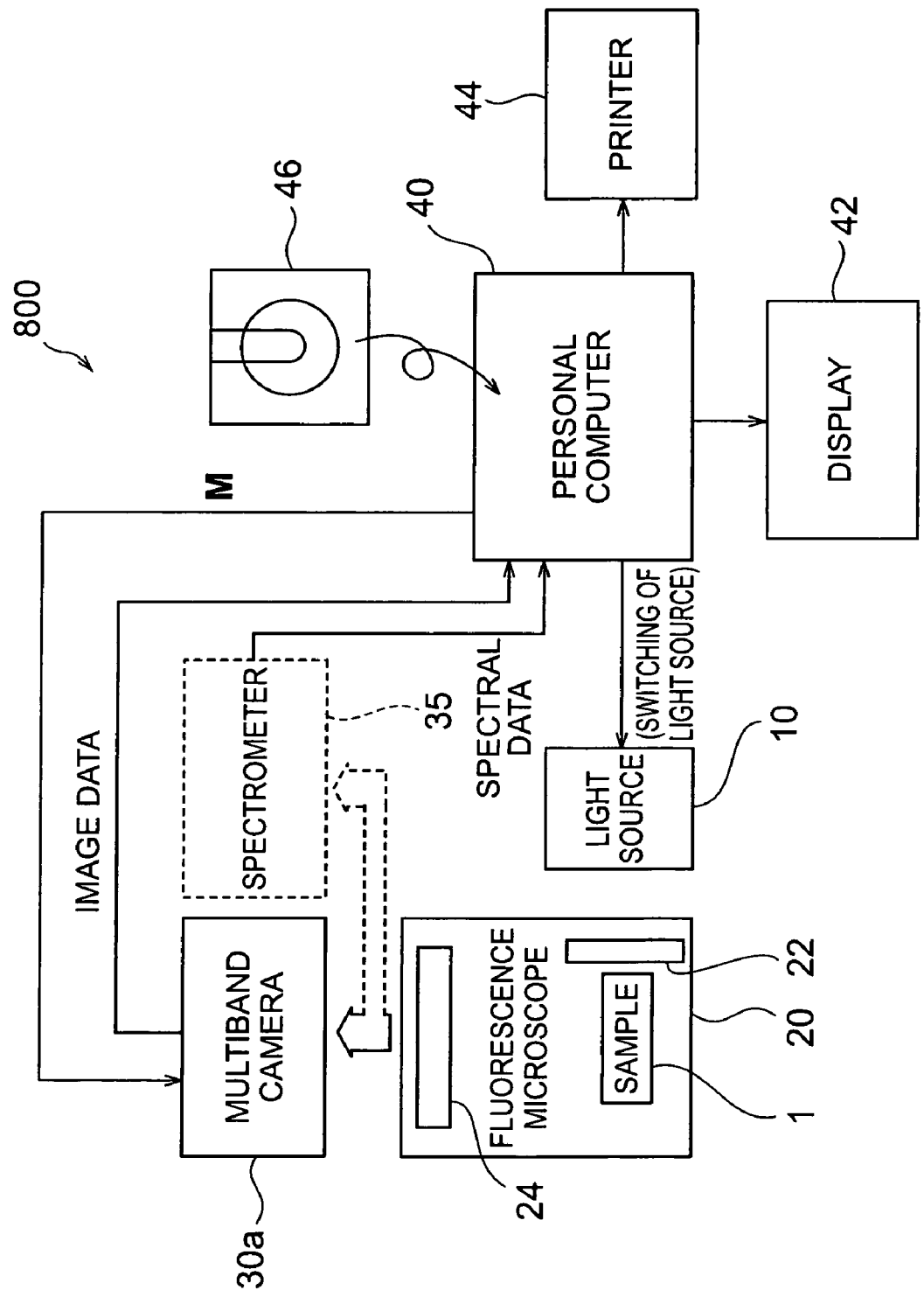
FIG. 21 is a block diagram showing a configuration of another example of a fluorescent dye measurement system.

Another embodiment of the present invention will be described below. FIG. 21 is a block diagram showing a configuration of a fluorescent dye measurement system of the present embodiment. This measurement system 800 has the configuration obtained by replacing the multiband camera 30 in the measurement system 100 of the first embodiment with multiband camera 30a. In the present embodiment a logic circuit in the multiband camera 30a executes the operation of the aforementioned Eq (7), instead of the personal computer 40.

Figure 22:
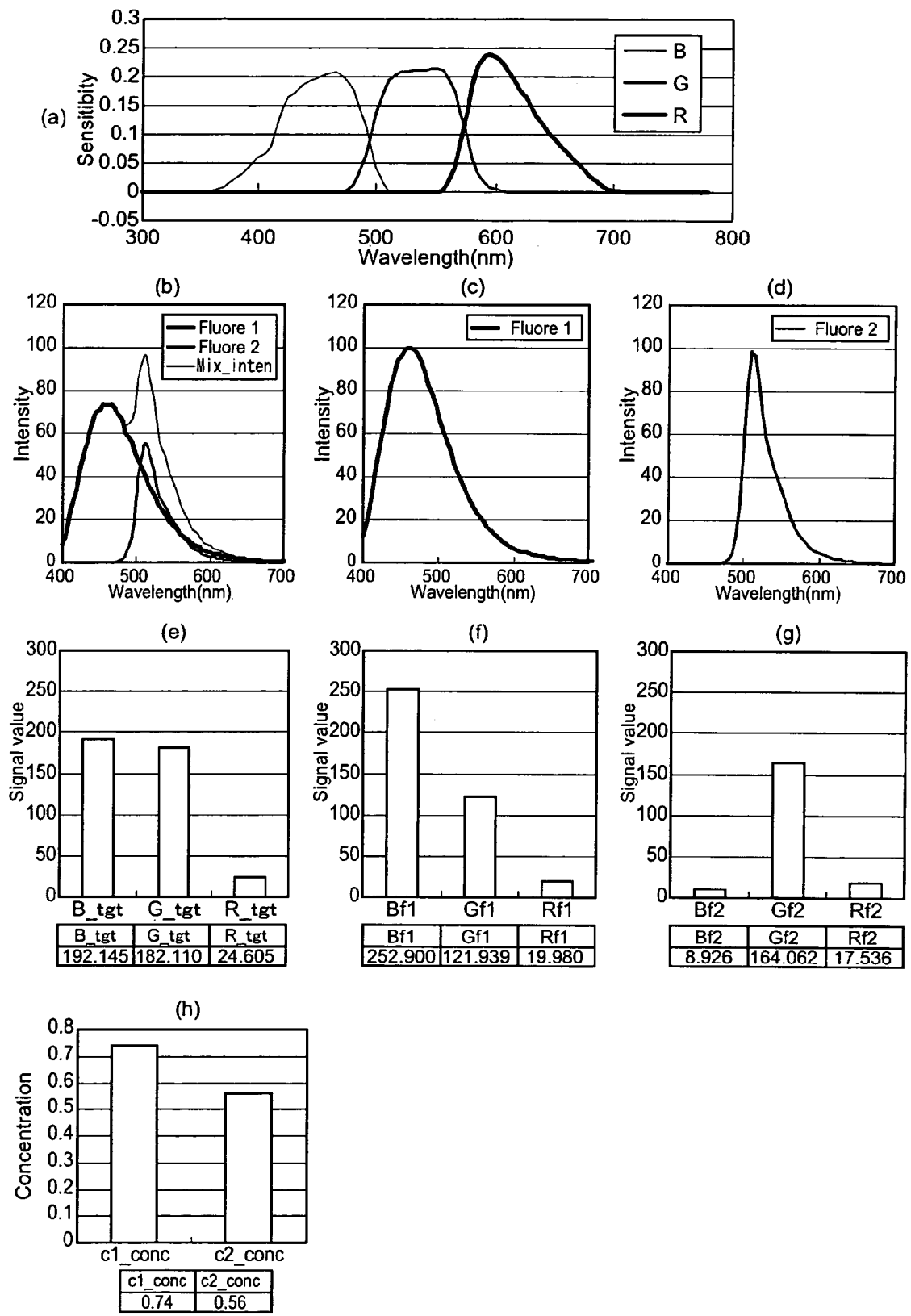
FIG. 22 is a diagram showing various data concerning measurement of fluorescent dyes.

FIG. 22 shows various data associated with the measurement of the present embodiment. Just as in the first embodiment, the multiband camera 30a has three detection wavelength bands, the R wavelength band, G wavelength band, and B wavelength band. FIG. 22(a) shows the sensitivity characteristics of the multiband camera 30a. As shown in this figure, portions of the detection wavelength bands overlap any adjacent bands. The multiband camera 30a includes three imaging devices corresponding to these detection wavelength bands, and a color separation prism for separating wavelength components of input light into the three detection wavelength bands and for feeding them to the corresponding imaging devices.

Figure 23:
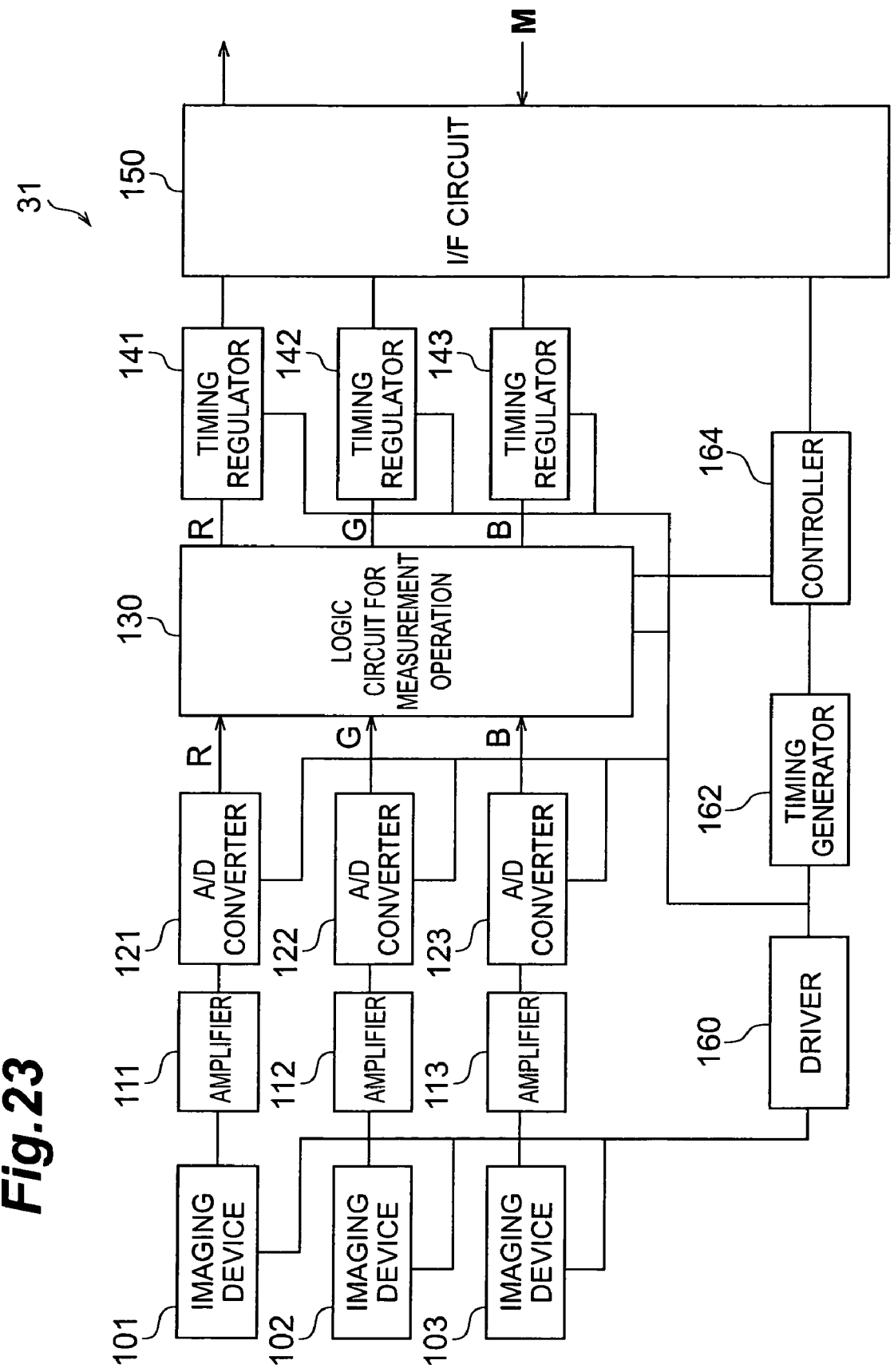
FIG. 23 is a block diagram showing an electronic circuit mounted on a multiband camera.

FIG. 23 is a block diagram showing a signal processing circuit mounted on the multiband camera 30a. In addition to the aforementioned three imaging devices 101-103, the signal processing circuit 31 includes amplifiers 111-113, A/D converters 121-123, a logic circuit 130 for measurement operation, timing regulator circuits 141-143, an interface circuit 150, a driving circuit 160, a timing generator circuit 162, and a control circuit 164.

The imaging devices 101-103 are driven by the driving circuit 160 to take fluorescence images of the target sample in the respective R, G, and B wavelength bands and to generate three image signals. These image signals are amplified by the corresponding amplifiers 111-113, the amplified signals are digitized by the A/D converters 121-123, and the digital signals are fed to the logic circuit 130 for measurement operation.

The logic circuit 130 executes the operation represented by the aforementioned Eq (7) using these image signals, to calculate the concentrations of the fluorescent dyes in the target sample pixel by pixel. The matrix $(J^T \cdot J)^{-1} \cdot J^T$ in Eq (7) will be referred to hereinafter as "reference data M." In the present embodiment this reference data M is fed from the computer 40 through the interface circuit 150 into the logic circuit 130. Instead thereof, however, the reference data M may be stored in a storage device provided in the multiband camera 30a. The logic circuit 130 assigns values according to the concentrations calculated for respective pixels, to the pixels to generate image signals indicating concentration distributions of the respective fluorescent dyes in the target sample. Each of these image signals is one of R, G, and B outputs from the multiband camera 30a.

The timing generator circuit 162 supplies a clock signal to the A/D converters 121-123, to the logic circuit 130, to the timing regulator circuits 141-143, to the driving circuit 160, and to the control circuit 164. The control circuit 164 receives a command from computer 40 through the external interface circuit 150 and controls the operation of the logic circuit 130 in accordance with the command. For example, the control circuit 164 can also prohibit the logic circuit 130 from executing the operation of Eq (7) and let the multiband camera 30a output the image data itself acquired in the R, G, and B wavelength bands. The R, G, and B outputs are synchronized by the timing regulator circuits 141-143 to be fed from the external interface circuit 150 to the computer 40.

The computer 40 displays an image for display of the measurement result using the R, G, and B outputs from the multiband camera 30a. on the display device 42. For example, as shown in FIG. 3, an image 63 with the R, G, and B outputs superimposed may be displayed along with the color bar 64, or, as shown in FIG. 4, the R, G, and B outputs may be displayed separately as independent images. The computer 40 can also make the printer 44 print these images.

How to measure the concentrations of the fluorescent dyes in the target sample with the measurement system 800 will be described below with a specific example. FIG. 22(b) shows fluorescence spectra of the target sample and the first and second fluorescent dyes. This target sample is one obtained by staining Hela cells with two types of fluorescent dyes, DAPI and Mito Tracker Green. DAPI stains the nuclei of the cells, and Mito Tracker Green stains the mitochondria. The fluorescence spectrum of DAPI has a peak near 460 nm, and the fluorescence spectrum of Mito Tracker Green a peak near 515 nm.

First, the reference samples are prepared to acquire the basic data, in the same manner as in the first embodiment. Specifically, the Hela cells are stained with DAPI only, and with Mito Tracker Green only to prepare the first and second reference samples. These reference samples are illuminated with the excitation light through the band-pass filter 22 having the transmitted wavelength band of 405±5 nm. FIG. 22(c) shows the fluorescence spectrum of the first reference sample and FIG. 22(d) the fluorescence spectrum of the second reference sample.

The optical images of fluorescence emitted from the reference samples are taken using the multiband camera 30a through the band-pass filter 24 having the transmitted wavelength band of not less than 420 nm. The imaging devices 101-103 in the multiband camera 30a generate data of three images acquired in the three detection wavelength band, for each reference sample. The computer 40 feeds a command to the control circuit 164 to prohibit the logic circuit 130 from executing the operation of Eq (7) and to make the multiband camera 30a output these image data. The image data is fed to the computer 40 to be stored in the storage device in the computer 40. Similar measurement is carried out for all the reference samples and image data thereof is stored.

In the reference samples of the present embodiment, the fluorescent dyes are scattered according to distributions of nuclei and mitochondria. For this reason, the value of an arbitrary pixel indicating a site emitting fluorescence in each reference sample is acquired from each fluorescence image of the reference sample to be used as basic data. FIG. 22(f) shows the R, G, and B values of a certain pixel, i.e., $Rf_1$, $Gf_1$, and $Bf_1$, acquired from the first reference sample. In this example, $Rf_1$=19.980, $Gf_1$=121.939, and $Bf_1$=252.900. FIG. 22(g) shows the R, G, and B values of a certain pixel i.e., $Rf_2$, $Gf_2$, and $Bf_2$, acquired from the second reference sample. In this example, $Rf_2$=17.536, $Gf_2$=164.062, and $Bf_2$=8.926. These values are the basic data acquired from the reference samples, and are equal to the components in the matrix J represented by Eq (2).

The computer 40 calculates the reference data M, i.e., the matrix $(J^T \cdot J)^{-1} \cdot J^T$, using the matrix J acquired as described above. The reference data thus calculated is stored into the storage device in the computer 40. As described hereinafter, this reference data M is used commonly in the operation of Eq (7) for all the pixels. The first stage of the measurement is completed in this manner.

Next, the target sample is illuminated with the excitation light through the band-pass filter 22 onto and an image of fluorescence emitted from the target sample is taken using the multiband camera 30a. This results in feeding three image signals indicating fluorescence images taken in the R, G, and B wavelength bands, to the logic circuit 130. FIG. 22(e) shows the R, G, and B values of a certain pixel, i.e., $R_{tgt}$, $G_{tgt}$, and $B_{tgt}$ in the fluorescence images of the target sample. In this example, $R_{tgt}$=24.605, $G_{tgt}$=182.110, and $B_{tgt}$=192.145.

The computer 40 feeds a command to the control circuit 164 to permit the logic circuit 130 to perform the operation of Eq (7) (practically, Eq (1)). The reference data M is also supplied from the computer 40 to the logic circuit 130. The logic circuit 130 executes the operation of Eq (1) for each pixel, using this reference data M, to calculate concentrations $c_1$ and $c_2$ of DAPI and Mito Tracker Green. FIG. 22(h) shows the concentrations $c_1$ and $c_2$ calculated for pixels having the R, G, and B values shown in FIG. 22(e). In this case, $c_1$=0.74, and $c_2$=0.56. Just as in the case of the above embodiments, the units of these concentration values are the concentrations of the fluorescent dyes in the corresponding reference samples.

The logic circuit 130 assigns the values according to the concentrations c1 and c2 calculated for each pixel, to the pixel to generate two image signals indicating the concentration distributions of DAPI and Mito Tracker Green in the target sample. These image signals are outputted as any of the R, G, and B signals from the logic circuit 130. Therefore, the concentration distribution of DAPI and Mito Tracker Green are fed as image data of different colors from the multiband camera 30a to the computer 40. These image signals may be transmitted to the computer 40 as separated from each other, or may be transmitted to the computer 40 after converted into a single composite signal. The computer 40 displays an image indicating the measurement results, using these image signals, on the display device 42.

FIG. 24 shows measurement result images in the present embodiment, in which (a) is an output image of the multiband camera 30a, (b) a concentration distribution image of DAPI separated from the output image, and (c) a concentration distribution image of Mito Tracker Green separated from the output image. Original images of these are color images, but the images herein are black-and-white images converted therefrom. Only nuclei are displayed in the image of DAPI, and only mitochondria in the image of Mito Tracker Green. As described above, the measurement system of the present embodiment is able to clearly separate and display two strictures in the cells in real time.

For comparison, the Inventor and others acquire a fluorescence image of a target sample with the 3-band camera not performing the operation of the aforementioned Eq (1). FIG. 25 shows measurement result images of this comparative example, in which (a) is an output image of the 3-band camera, and (b) and (c) fluorescence images in the B wavelength region and in the G wavelength region extracted from the output image. These are also originally color images, but they are shown as black-and-white images converted therefrom. According to distributions of the fluorescence spectra of the dyes used, the fluorescence of DAPI is detected in both of the R and G wavelength regions, and most of the fluorescence of Mito Tracker Green is detected in the G region. For this reason, only the image of nuclei stained with DAPI appears in the image of the B wavelength region, but the image in the G wavelength region includes overlapping images of mitochondria stained with Mito Tracker Green and nuclei stained with DAPI.

In the present embodiment, instead of the software operating on the personal computer 40, the hardware in the multiband camera 30a performs the measurement operation and generates the image signals indicating the concentration distributions, using the operation result. For this reason, the concentration distribution images can be displayed quicker than in the case where the concentration distribution images are generated by the software processing. As a result, a user can confirm the results of the measurement immediately after the image acquisition of the target sample.

The technique of the present embodiment can also be applied to any one of the aforementioned embodiments using the multiband camera. It is also possible to use the spectrometer 35 for acquiring the basic data from the reference samples, as in the second embodiment.

The present invention was described above in detail on the basis of the embodiments thereof. It is, however, noted that the present invention is by no means limited to the above embodiments. The present invention can be modified in various ways without departing from the scope thereof.

The above embodiments mainly used the imaging device having the R, G, and B wavelength bands as the detection wavelength bands. However, the imaging device to be used in the present invention may have any other detection wavelength bands.

The aforementioned Eq (1) is the equation where the matrix J is not regular. The reason why the matrix J is not regular is that the number of fluorescent dyes contained in the target sample is not coincident with the number of detection wavelength bands. Since the detection wavelength bands in the first embodiment are three, the matrix J will be regular if there are three types of fluorescent dyes in the target sample. In this case, Eq (1) is rewritten into a simple form as follows.

[Formula 23]

$$\begin{bmatrix} c_1 \\ c_2 \\ c_3 \end{bmatrix} = J^{-1} \cdot \begin{bmatrix} R_{tgt} \\ G_{tgt} \\ B_{tgt} \end{bmatrix} \quad (27)$$

Figure 26:
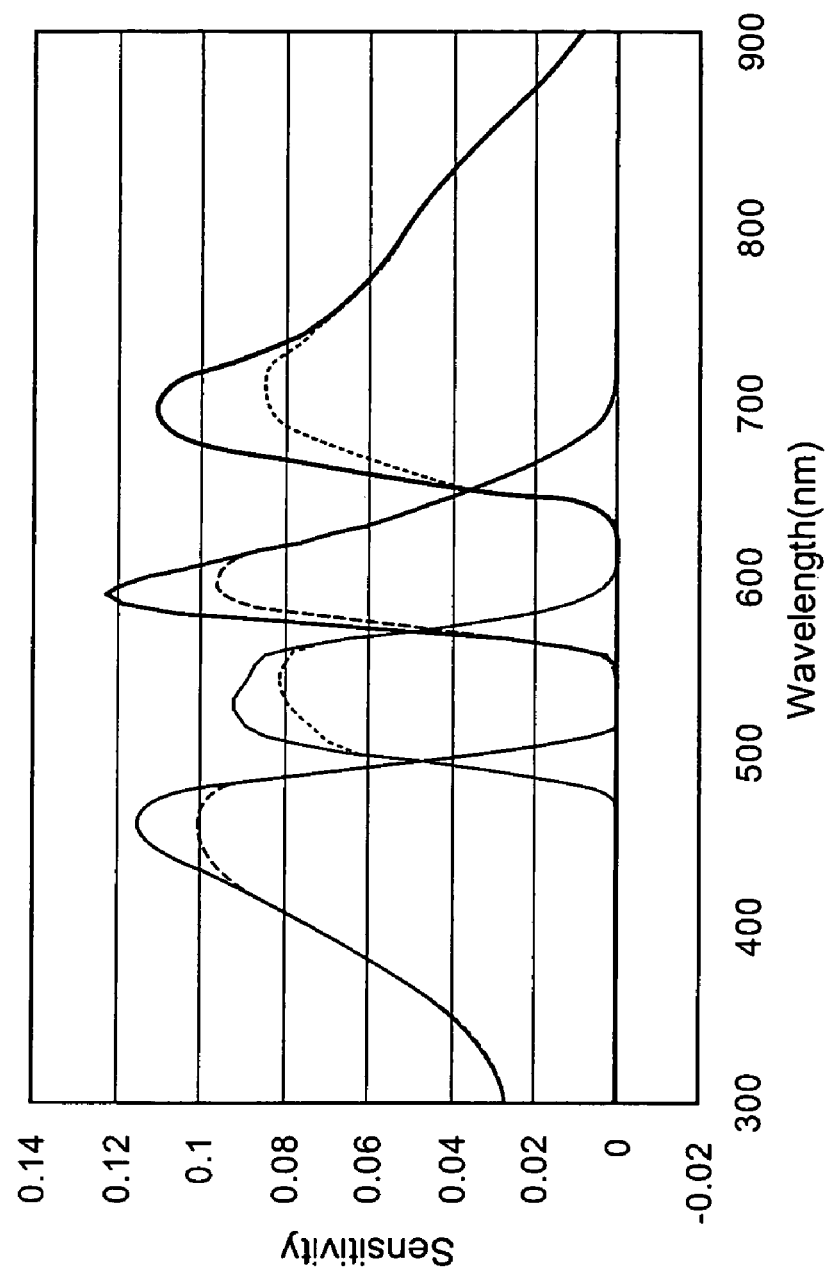
FIG. 26 is a diagram showing sensitivity characteristics of a 4-band camera.

A 4-band -camera having the sensitivity characteristics shown in FIG. 26 may be used instead of the 3-band camera used in the above embodiments. This 4-band camera also has the two sensitivity modes, the Low Light mode and the High Light mode. Therefore, as described in the third embodiment, the fluorescent dyes can be measured up to eight types. As shown in FIG. 26, this 4-band camera has the sensitivity in the near-infrared region. Therefore, this 4-band camera is useful in the measurement of the fluorescent dyes having the emission region in the near-infrared region.

The multiband camera 30a used in the eighth embodiment has the color separation prism and the plurality of imaging devices, but, instead thereof, the multiband camera may have one imaging device with a color mosaic filter or the like printed thereon.

INDUSTRIAL APPLICABILITY

The methods and measurement systems of the present invention are able to accurately measure the concentrations of a plurality of fluorescent dyes having overlapping fluorescence spectra.

The invention claimed is:

1. A method of measuring concentrations of first to mth (where m is an integer of 2 or more) fluorescent dyes contained in a target sample, using an imaging device having first to kth (where k is an integer of 2 or more) different detection wavelength bands, portions of the detection wavelength bands overlapping any adjacent bands, comprising:

preparing first to mth reference samples each containing only one of the first to mth fluorescent dyes respectively at predetermined unit concentrations, and acquiring a measured intensity of fluorescence emitted from each reference sample in each detection wavelength band;

taking a fluorescence image of the target sample in each detection wavelength band using the imaging device; and executing an operation represented by a formula below, to calculate concentrations $c_1$-$c_m$ of the first to mth fluorescent dyes at a site in the target sample,

[Formula 24]

$$\begin{bmatrix} c_1 \\ c_2 \\ \vdots \\ c_m \end{bmatrix} = (J^T \cdot J)^{-1} \cdot J^T \cdot \begin{bmatrix} O_1 \\ O_2 \\ \vdots \\ O_k \end{bmatrix},$$

$$J = \begin{bmatrix} J_{11} & J_{12} & \cdots & J_{1m} \\ J_{21} & J_{22} & \cdots & J_{2m} \\ \vdots & \vdots & & \vdots \\ J_{k1} & J_{k2} & \cdots & J_{km} \end{bmatrix}$$

where $O_1$-$O_k$ represent values of pixels in the fluorescence images of the target sample taken in the first to kth detection wavelength bands, the pixels corresponding to the site, J is a k×m matrix, and a component $J_{ij}$ in the ith row and jth column (where i is any integer from 1 to k, and j is any integer from 1 to m) in J is the measured intensity in the ith detection wavelength band of the fluorescence emitted from the jth reference sample.

2. A method according to claim 1, wherein the imaging device includes a multiband camera having the first to kth detection wavelength bands, wherein the acquiring a measured intensity of fluorescence emitted from each reference sample in each detection wavelength band includes taking the fluorescence image of each reference sample in each detection wavelength band using the multiband camera and acquiring a value of a pixel from each fluorescence image, the pixel representing a site emitting the fluorescence in each reference sample, and wherein the calculation of the concentrations $c_1$-$c_m$ of the first to mth fluorescent dyes includes using the value of the pixel acquired from the fluorescence image of the jth reference sample taken in the ith detection wavelength band as the component $J_{ij}$ in the matrix J.

3. A method according to claim 1, wherein the imaging device includes a multiband camera having the first to kth detection wavelength bands, and wherein the acquiring a measured intensity of fluorescence emitted from each reference sample in each detection wavelength band includes measuring spectral intensities of the fluorescence emitted from each reference sample using a spectrometer, and calculating the measured intensity in each detection wavelength band of the fluorescence emitted from each reference sample, using the spectral intensities and a sensitivity characteristic of the multiband camera for each detection wavelength band.

4. A method according to claim 1, wherein the imaging device includes one or more imaging devices for taking the fluorescence images of the target sample in the first to kth detection wavelength bands to generate first to kth image signals, and an arithmetic circuit to which the first to kth image signals are fed, wherein the calculation of the concentrations $c_1$-$c_m$ of the first to mth fluorescent dyes includes a process in which the arithmetic circuit executes the operation using the first to kth image signals, the method further comprising: causing the arithmetic circuit to calculate the concentrations $c_1$-$c_m$ at a plurality of sites in the target sample and to generate first to mth image signals indicating concentration distributions of the first to mth fluorescent dyes.

5. A method of measuring concentrations of first to mth (where m is an integer of 2 or more) fluorescent dyes contained in a target sample using an imaging device having first to kth (where k is an integer of 2 or more) different detection wavelength bands, portions of the detection wavelength bands overlapping any adjacent bands, and the imaging device having first to qth (where q is an integer of 2 or more) sensitivity modes for setting different sensitivity characteristics of the imaging device, comprising:

preparing first to mth reference samples each containing only one of the first to mth fluorescent dyes respectively at predetermined unit concentrations, and acquiring a measured intensity of fluorescence emitted from each reference sample in each detection wavelength band and in each sensitivity mode;

taking a fluorescence image of the target sample in each detection wavelength band and in each sensitivity mode using the imaging device; and executing an operation represented by a formula below, to calculate concentrations $c_1$-$c_m$ of the first to mth fluorescent dyes at a site in the target sample,

[Formula 25]

$$\begin{bmatrix} c_1 \\ c_2 \\ \vdots \\ c_m \end{bmatrix} = (J_1^T \cdot J_1)^{-1} \cdot J^T \cdot \begin{bmatrix} P_1 \\ P_2 \\ \vdots \\ P_q \end{bmatrix},$$

$$P_v = \begin{bmatrix} P_{1v} \\ P_{2v} \\ \vdots \\ P_{kv} \end{bmatrix}$$

$$J_1 = \begin{bmatrix} L_{11} & L_{12} & \cdots & L_{1m} \\ L_{21} & L_{22} & \cdots & L_{2m} \\ \vdots & \vdots & & \vdots \\ L_{q1} & L_{q2} & \cdots & L_{qm} \end{bmatrix},$$

$$L_{vj} = \begin{bmatrix} L_{1vj} \\ L_{2vj} \\ \vdots \\ L_{kvj} \end{bmatrix}$$

where $P_v$ (where v is any integer from 1 to q) is a k×1 matrix, a component $P_{iv}$ in the ith row (where i is any integer from 1 to k) in $P_v$ is a value of a pixel in the fluorescence image of the target sample taken in the ith detection wavelength band and in the vth sensitivity mode using the imaging device, the pixel corresponding to the site, $J_1$ a (k·q)×m matrix, and a component $L_{ivj}$ in the ith row in a component matrix $L_{vj}$ (where j is any integer from 1 to m) in $J_1$ the measured intensity in the ith detection wavelength band and in the vth sensitivity mode of the fluorescence emitted from the jth reference sample.

6. A method according to claim 5, wherein the imaging device includes one or more imaging devices for taking the fluorescence images of the target sample in the first to kth detection wavelength bands to generate first to kth image signals, and an arithmetic circuit to which the first to kth image signals are fed, wherein the calculation of the concentrations $c_1$-$c_m$ of the first to mth fluorescent dyes includes a process in which the arithmetic circuit executes the operation using the first to kth image signals, the method further comprising: causing the arithmetic circuit to calculate the concentrations $c_1$-$c_m$ at a plurality of sites in the target sample and to generate first to mth image signals indicating concentration distributions of the first to mth fluorescent dyes.

7. A method of measuring concentrations of first to mth (where m is an integer of 2 or more) fluorescent dyes contained in a target sample using an imaging device having first to kth (where k is an integer of 2 or more) different detection wavelength bands, portions of the detection wavelength bands overlapping any adjacent portions, comprising:

preparing first to mth reference samples, each reference sample containing only one of the first to mth fluorescent dyes respectively at predetermined unit concentrations, illuminating the first to mth reference samples with each of first to rth (where r is an integer of 2 or more) excitation beams having different wavelength spectra for exciting all the first to mth fluorescent dyes, and acquiring a measured intensity in each detection wavelength band of fluorescence emitted from each reference sample;

illuminating the target sample with each excitation beam and taking a fluorescence image of the target sample in each detection wavelength band using the imaging device; and executing an operation represented by a formula below, to calculate concentrations $c_1$-$c_m$ of the first to mth fluorescent dyes at a site in the target sample,

[Formula 26]

$$\begin{bmatrix} c_1 \\ c_2 \\ \vdots \\ c_m \end{bmatrix} = (J_2^T \cdot J_2)^{-1} \cdot J_2^T \cdot \begin{bmatrix} Q_1 \\ Q_2 \\ \vdots \\ Q_r \end{bmatrix},$$

$$Q_u = \begin{bmatrix} Q_{1u} \\ Q_{2u} \\ \vdots \\ Q_{ku} \end{bmatrix}$$

$$J_2 = \begin{bmatrix} T_{11} & T_{12} & \cdots & T_{1m} \\ T_{21} & T_{22} & \cdots & T_{2m} \\ \vdots & \vdots & & \vdots \\ T_{r1} & T_{r2} & \cdots & T_{rm} \end{bmatrix},$$

$$T_{uj} = \begin{bmatrix} T_{1uj} \\ T_{2uj} \\ \vdots \\ T_{kuj} \end{bmatrix}$$

where $Q_u$ (where u is any integer from 1 to r) is a k×1 matrix, a component $Q_{iu}$ in the ith row (where i is any integer from 1 to k) in $Q_u$ a value of a pixel in the fluorescence image of the target sample taken in the ith detection wavelength band upon illuminating the target sample with the uth excitation beam, the pixel corresponding to the site, $J_2$ a (k·r)×m matrix, and a component $T_{iuj}$ in the ith row of a component matrix $T_{uj}$ (where j is any integer from 1 to m) in $J_2$ the measured intensity in the ith detection wavelength band of the fluorescence emitted from the jth reference sample upon illuminating the jth reference sample with the uth excitation beam.

8. A method according to claim 7, wherein the imaging device includes one or more imaging devices for taking the fluorescence images of the target sample in the first to kth detection wavelength bands to generate first to kth image signals, and an arithmetic circuit to which the first to kth image signals are fed, wherein the calculation of the concentrations $c_1$-$c_m$ of the first to mth fluorescent dyes includes a process in which the arithmetic circuit executes the operation using the first to kth image signals, the method further comprising: causing the arithmetic circuit to calculate the concentrations $c_1$-$c_m$ at a plurality of sites in the target sample and to generate first to mth image signals indicating concentration distributions of the first to mth fluorescent dyes.

9. A system for measuring concentrations of first to mth (where m is an integer of 2 or more) fluorescent dyes contained in a target sample, comprising:
   a photodetector for detecting fluorescence emitted from each of first to mth reference samples each containing only one of the first to mth fluorescent dyes respectively at predetermined unit concentrations, and for measuring an intensity of the fluorescence;
   an imaging device having first to kth (where k is an integer of 2 or more) different detection wavelength bands and configured to take a fluorescence image of the target sample in each detection wavelength band, portions of the detection wavelength bands overlapping any adjacent bands; and
   an arithmetic device for executing an operation represented by a formula below, to calculate concentrations $c_1$-$c_m$ of the first to mth fluorescent dyes at a site in the target sample,

[Formula 27]

$$\begin{bmatrix} c_1 \\ c_2 \\ \vdots \\ c_m \end{bmatrix} = (J^T \cdot J)^{-1} \cdot J^T \cdot \begin{bmatrix} O_1 \\ O_2 \\ \vdots \\ O_k \end{bmatrix},$$

$$J = \begin{bmatrix} J_{11} & J_{12} & \cdots & J_{1m} \\ J_{21} & J_{22} & \cdots & J_{2m} \\ \vdots & \vdots & & \vdots \\ J_{k1} & J_{k2} & \cdots & J_{km} \end{bmatrix}$$

where $O_1$-$O_k$ are values of pixels in the fluorescence images of the target sample taken in the first to kth detection wavelength bands, the pixels corresponding to the site, J is a k×m matrix, and a component $J_{ij}$ in the ith row and jth column (where i is any integer from 1 to k, and j any integer from 1 to m) in J the intensity in the ith detection wavelength band of the fluorescence emitted from the jth reference sample, measured by the photodetector.

10. A system according to claim 9, including a multiband camera having the first to kth detection wavelength bands as the photodetector and the imaging device,
   wherein the photodetector takes the fluorescence image of each reference sample in each detection wavelength band, and acquires a value of a pixel representing a site emitting the fluorescence in each reference sample, from each fluorescence image, and
   wherein the arithmetic device uses a value of the pixel acquired from the fluorescence image of the jth reference sample taken in the ith detection wavelength band as the component $J_{ij}$ of the matrix J.

11. A system according to claim 9, wherein the photodetector includes a spectrometer for measuring spectral intensities of the fluorescence emitted from each reference sample,
   wherein the imaging device includes a multiband camera having the first to kth detection wavelength bands, and
   wherein the arithmetic device calculates an intensity in each detection wavelength band of the fluorescence emitted from each reference sample, using the spectral intensities and a sensitivity characteristic of the multiband camera for each detection wavelength band, and uses the calculated intensities as components of the matrix J.

12. A system according to claim 9, wherein the imaging device includes one or more imaging devices for taking the fluorescence images of the target sample in the first to kth detection wavelength bands to generate first to kth image signals, and an arithmetic circuit as the arithmetic device to which the first to kth image signals are fed, and
   wherein the arithmetic circuit executes the operation using the first to kth image signals to calculate the concentrations $c_1$-$c_m$ at a plurality of sites of the target sample, and generates first to mth image signals indicating concentration distributions of the first to mth fluorescent dyes.

13. A system for measuring concentrations of first to mth (where m is an integer of 2 or more) fluorescent dyes contained in a target sample, comprising:
   a photodetector for detecting fluorescence emitted from each of first to mth reference samples each containing only one of the first to mth fluorescent dyes respectively at predetermined unit concentrations;
   an imaging device having first to kth (where k is an integer of 2 or more) different detection wavelength bands and having first to qth (where q is an integer of 2 or more) sensitivity modes for setting different sensitivity characteristics of the imaging device, the imaging device taking a fluorescence image of the target sample in each detection wavelength band and in each sensitivity characteristic, portions of the detection wavelength bands overlapping any adjacent bands; and
   an arithmetic device for executing an operation represented by a formula below, to calculate concentrations $c_1$-$c_m$ of the first to mth fluorescent dyes at a site in the target sample,

[Formula 28]

$$\begin{bmatrix} c_1 \\ c_2 \\ \vdots \\ c_m \end{bmatrix} = (J_1^T \cdot J_1)^{-1} \cdot J_1^T \cdot \begin{bmatrix} P_1 \\ P_2 \\ \vdots \\ P_q \end{bmatrix},$$

$$P_v = \begin{bmatrix} P_{1v} \\ P_{2v} \\ \vdots \\ P_{kv} \end{bmatrix}$$

$$J_1 = \begin{bmatrix} L_{11} & L_{12} & \cdots & L_{1m} \\ L_{21} & L_{22} & \cdots & L_{2m} \\ \vdots & \vdots & & \vdots \\ L_{q1} & L_{q2} & \cdots & L_{qm} \end{bmatrix},$$

$$L_{vj} = \begin{bmatrix} L_{1vj} \\ L_{2vj} \\ \vdots \\ L_{kvj} \end{bmatrix}$$

where $P_v$ (where v is any integer from 1 to q) is a k×1 matrix, a component $P_{iv}$ in the ith row (where i is any integer from 1 to k) in $P_v$ a value of a pixel in the fluorescence image of the target sample taken in the ith detection wavelength band and in the vth sensitivity mode, the pixel corresponding to the site, $J_1$ a (k·q)×m matrix, and a component $L_{ivj}$ in the ith row of a component matrix $L_{vj}$ (where j is any integer from 1 to m) in $J_1$ the measured intensity in the ith detection wavelength band and in the vth sensitivity mode of the fluorescence emitted from the jth reference sample.

14. A system according to claim 13, wherein the imaging device includes one or more imaging devices for taking the fluorescence images of the target sample in the first to kth detection wavelength bands to generate first to kth image signals, and an arithmetic circuit as the arithmetic device to which the first to kth image signals are fed, and wherein the arithmetic circuit executes the operation using the first to kth image signals to calculate the concentrations $c_1$-$c_m$ at a plurality of sites of the target sample, and generates first to mth image signals indicating concentration distributions of the first to mth fluorescent dyes.

15. A system for measuring concentrations of first to mth (where m is an integer of 2 or more) fluorescent dyes contained in a target sample, comprising:

a light source for generating first to rth (where r is an integer of 2 or more) excitation beams having different wavelength spectra for exciting all the first to mth fluorescent dyes;

a photodetector for measuring an intensity of fluorescence emitted from each of first to mth reference samples upon illuminating each reference sample with each excitation beam, each reference sample containing only one of the first to mth fluorescent dyes respectively at predetermined unit concentrations;

an imaging device having first to kth (where k is an integer of 2 or more) different detection wavelength bands and configured to take a fluorescence image of the target sample in each detection wavelength band upon illuminating the target sample with each excitation beam, portions of the detection wavelength bands overlapping any adjacent bands; and an arithmetic device for executing an operation represented by a formula below, to calculate concentrations $c_1$-$c_m$ of the first to mth fluorescent dyes at a site in the target sample,

[Formula 29]

$$\begin{bmatrix} c_1 \\ c_2 \\ \vdots \\ c_m \end{bmatrix} = (J_2^T \cdot J_2)^{-1} \cdot J_2^T \cdot \begin{bmatrix} Q_1 \\ Q_2 \\ \vdots \\ Q_r \end{bmatrix},$$

-continued $$Q_u = \begin{bmatrix} Q_{1u} \\ Q_{2u} \\ \vdots \\ Q_{ku} \end{bmatrix}$$

$$J_2 = \begin{bmatrix} T_{11} & T_{12} & \cdots & T_{1m} \\ T_{21} & T_{22} & \cdots & T_{2m} \\ \vdots & \vdots & & \vdots \\ T_{r1} & T_{r2} & \cdots & T_{rm} \end{bmatrix},$$

$$T_{uj} = \begin{bmatrix} T_{1uj} \\ T_{2uj} \\ \vdots \\ T_{kuj} \end{bmatrix}$$

where $Q_u$ (where u is any integer from 1 to r) is a k×1 matrix, a component $Q_{iu}$ in the ith row (where i is any integer from 1 to k) in $Q_u$ a value of a pixel in the fluorescence image of the target sample taken in the ith detection wavelength band upon illuminating the target sample with the uth excitation beam, the pixel corresponding to the site, $J_2$ a (k·r)×m matrix, and a component $T_{iuj}$ in the ith row of a component matrix $T_{uj}$ (where j is any integer from 1 to m) in $J_2$ the measured intensity of the fluorescence in the ith detection wavelength band upon illuminating the jth reference sample with the uth excitation beam.

16. A system according to claim 15, wherein the imaging device includes one or more imaging devices for taking the fluorescence images of the target sample in the first to kth detection wavelength bands to generate first to kth image signals, and an arithmetic circuit as the arithmetic device to which the first to kth image signals are fed, and wherein the arithmetic circuit executes the operation using the first to kth image signals to calculate the concentrations $c_1$-$c_m$ at a plurality of sites of the target sample, and generates first to mth image signals indicating concentration distributions of the first to mth fluorescent dyes.

* * * * *